US010760094B2

(12) United States Patent
Stahl et al.

(10) Patent No.: US 10,760,094 B2
(45) Date of Patent: Sep. 1, 2020

(54) **TRANSGENIC PLANT OF THE SPECIES *SOLANUM TUBEROSUM* WITH RESISTANCE TO *PHYTOPHTHORA***

(71) Applicant: KWS SAAT SE & CO. KGAA, Einbeck (DE)

(72) Inventors: Jurgen Dietmar Stahl, Einbeck (DE); Nora Temme, Munster (DE)

(73) Assignee: KWS SAAT SE & CO. KGAA, Einbeck (DE)

( * ) Notice: Subject to any disclaimer, the term of this patent is extended or adjusted under 35 U.S.C. 154(b) by 0 days.

(21) Appl. No.: 16/027,855

(22) Filed: Jul. 5, 2018

(65) Prior Publication Data

US 2018/0305712 A1 Oct. 25, 2018

Related U.S. Application Data

(62) Division of application No. 14/420,106, filed as application No. PCT/DE2013/000446 on Aug. 6, 2013, now Pat. No. 10,030,251.

(30) Foreign Application Priority Data

Aug. 8, 2012 (DE) ........................ 10 2012 016 009

(51) Int. Cl.
*C12N 15/82* (2006.01)
*C12N 15/113* (2010.01)

(52) U.S. Cl.
CPC ........ *C12N 15/8282* (2013.01); *C12N 15/113* (2013.01); *C12N 2310/14* (2013.01); *C12N 2310/141* (2013.01)

(58) Field of Classification Search
CPC ................................................ C12N 115/8286
USPC .......................................................... 800/279
See application file for complete search history.

(56) References Cited

U.S. PATENT DOCUMENTS

| | | | |
|---|---|---|---|
| 8,299,318 | B2 | 10/2012 | Brover et al. |
| 2010/0257634 | A1 | 10/2010 | Bailey et al. |
| 2011/0167514 | A1 | 7/2011 | Brover et al. |
| 2015/0082495 | A1 | 3/2015 | Delebarre et al. |

FOREIGN PATENT DOCUMENTS

| | | | |
|---|---|---|---|
| CN | 101107362 | A | 1/2008 |
| DE | 102012016009 | A1 | 2/2014 |
| EP | 1716238 | A1 | 11/2006 |
| WO | 2006047495 | A2 | 5/2006 |
| WO | 2006070227 | A2 | 7/2006 |
| WO | 2009112270 | A2 | 9/2009 |
| WO | 2014023285 | A2 | 2/2014 |

OTHER PUBLICATIONS

Fourgoux-Nicol et al 1999, Plant Molecular Biology 40 :857-872.*
Thomas et al. 2001, The Plant Journal 25(4):417-425.*
Avrova AO, Boevink PC, Young V, Grenville-Briggs LJ, van West P, Birch PR, Whisson SC (2008) A novel Phytophthora infestans haustorium-specific membrane protein is required for infection of potato. Cell Microbial. 10(11):2271-84.
Benfey, P. N., Ren, L., and Chua, N.-H. (1990). Combinatorial and synergistic properties of CaMV 35S enhancer subdomains. EMBO J. (9), 1685-1696.
Birch RG, Shen B, Sawyer BJ, Huttner E, Tucker WQ, Betzner AS (2010) Evaluation and application of a luciferase fusion system for rapid in vivo analysis of RNAi targets and constructs in plants. Plant Biotechnol J. May 1 ;8(4):465-75. Epub Jan. 19, 2010.
Blackman LM, Arikawa M, Yamada S, Suzak.i T, Hard ham AR (2011) Identification of a mastigoneme protein from Phytophthora nicotianae. Protist. 162(1):100-14.
Catalanotto, C. et al., "Involvement of small RNAs and role of the qde genes in the gene silencing pathway in Neurospora", Research Communication, Genes & Development (2002), vol. 16, pp. 790-795.
Chomczynski P, Sacchi N. (1987) Single-step method of RNA isolation by acid guanidinium thiocyanate-phenol-chloroform extraction. Anal Biochem.162(1):156-9.
Eckes P., Rosahl S., Schell J., Willrnitzer L. (1986) Isolation and characterization of a light-inducible, organ-specific gene from potato and analysis of its expression after tagging and transfer into tobacco and potato shoots. Molecular and General Genetics 205 (1) 14-22, DOI: 10.1007/BF02428027.
Fire A, Xu S, Montgomery MK, Kostas SA, Driver SE, Mello CC. (1998) Potent and specific genetic interference by double-stranded RNA in Caenorhabditis elegans. Nature Feb. 19;391(6669):806-11.
Grenville-Briggs LJ, Avrova AO, Bruce CR, Williams A, Whisson SC, Birch PR, van West P (2005) Elevated amino acid biosynthesis in Phytophthora infestans during appressorium formation and potato infection. Fungal Genet Biol. 42(3):244-56.
Inoue SB, Takewaki N, Takasuka T, Mio T, Adachi M, Fujii Y, Miyamoto C, Arisawa M, Furuichi Y, Watanabe T (1995) Characterization and gene cloning of 1,3-beta-D-glucan synthase from *Saccharomyces cerevisiae*. Eur J Biochem 231(3):845-54.
International Search Report for PCT/DE2013/000446 dated Mar. 11, 2014.
International Preliminary Report on Patentability and Written Opinion for PCT/DE2013/000446 dated Feb. 10, 2015.

(Continued)

*Primary Examiner* — Li Zheng
(74) *Attorney, Agent, or Firm* — Troutman Pepper Hamilton Sanders LLP

(57) ABSTRACT

The present invention concerns a transgenic plant of the species *Solanum tuberosum* with a resistance to an oomycete of the genus *Phytophthora*, transgenic parts of such a plant, a method for its manufacture and to a composition for external application to plants. On the one hand, nucleotide sequences in accordance with SEQ ID NOS: 1-43 are provided from *Phytophthora* in a host plant-induced gene silencing strategy in potato plants; on the other hand, a fungicide for plant treatment is provided.

14 Claims, 33 Drawing Sheets

Specification includes a Sequence Listing.

(56) References Cited

OTHER PUBLICATIONS

Jan. 28, 2005 "PE006G1 mycelium, carbon starvation Phytophthora infestans cDNA, mRNA sequence.", XP002717637 retrieved from EBI accession No. EM_EST:CV909836, Database accession No. CV909836 sequence.
Judelson HS, Narayan RD, Ah-Fong AM, Kim KS (2009a) Gene expression changes during asexual sporulation by the late blight agent Phytophthora infestans occur in discrete temporal stages. Mol Genet Genomics. 281(2):193-206.
Judelson HS, Tani S, Narayan RD (2009b) Metabolic adaptation of Phytophthora infestans during growth on leaves, tubers and artificial media. Mol Plant Pathol. 10(6):843-55.
Kamoun S, van West P, Vleeshouwers VG, de Groot KE, Govers F. (1998) . Resistance of nicotiana benthamiana to phytophthora infestans is mediated by the recognition of the elicitor protein INF1. Plant Cell. Sep.; 10(9): 1413-26.
Koch, A. et al. "New wind in the sails: improving the agronomic value of crop plants through RNAi-mediated gene silencing", Plant Biotechnology Journal (2014), vol. 12, pp. 821-831.
Lesage G, Sdicu AM, Menard P, Shapiro J, Hussein S, Bussey H (2004) Analysis of beta-1,3-glucan assembly in *Saccharomyces cerevisiae* using a synthetic interaction network and altered sensitivity to caspofungin. Genetics. May;167(1):35-49.
Li A, Wang Y, Tao K, Dong S, Huang Q, Dai T, Zheng X, Wang Y (2010) PsSAK1, a Stress-Activated MAP Kinase of Phytophthora sojae, Is Required for Zoospore Viability and Infection of Soybean. Mol Plant Microbe Interact. 23(8):1022-31.
Loke, S. L., et al., "Characterization of oligonucleotide transport into living cells", Proc. Natl. Acad., Sci. (1989), vol. 86, pp. 3474-3478.
Mazur P, Morin N, Baginsky W, el-Sherbeini M, Clemas JA, Nielsen JB, Foor F (1995) Differential expression and function of two homologous subunits of yeast 1,3-beta-D-glucan synthase. Mol Cell Biol. 15(10):5671-81.
Meister, G. et al., "Mechanisms of gene silencing by double-stranded RNA", Nature (2004), vol. 431, pp. 343-349.
Nov. 15, 2012 "Sequence 12097 from U.S. Pat. No. 8,299,318.", retrieved from EBI accession No. EM_PAT: GZ562039, Database accession No. GZ562039 sequence.
Pel MA, Foster SJ, Park TH, Rietman H, van Arkel G, Jones JDG, Van Eck HJ, Jacobsen E, Visser RGF, Van der Vossen EAG (2009) Mapping and doning of late blight resistance genes from Solanum venturii using an interspecific candidate gene approach. MPMI 22:601-615.
Pieter van West, et al., "Internuclear Gene Silencing in Phytophthora Infestans", Molecular Cell 3(3): 339-348 (1999).
Randall, T.A. et al., "Large-Scale Gene Discovery in the Oomycete Phytophthora infestans Reveals Likely Components of Phytopathogenicity Shared with True Fungi", MPMI (2005), vol. 18, No. 3, pp. 229-243; EBI : Accession No. CV909836.
Roemer T, Paravicini G, Payton MA, Bussey H (1994) Characterization of the yeast (1->6)-beta-glucan biosynthetic components, Kre6p and Skn1 p, and genetic interactions between the PKC1 pathway and extracellular matrix assembly. J Cell Biol. 127(2):567-79.
Saito, K., Yamazaki, M., Kaneko, H., Murakoshi, I., Fukuda, Y., and van Montagu, M. (1991). Tissue-specific and stress-enhancing expression of the TR promoter for mannopine synthase in transgenic medicinal plants. Plants 184, 40-46.
Schmidt K., Heberle B., Kurrasch J., Nehls R., Stahl D.J. (2004) Suppression of phenylalanine ammonia lyase expression in sugar beet by the fungal pathogen *Cercospora beticola* is mediated at the core promoter of the gene. Plant Mol. Biol., 55: 835-852.
Stahl D. J., Kloos, D. U., and Hehl, R. (2004). A sugar beet chlorophyll a/b binding protein void of G-box like elements confer strong and leaf specific reporter gene expression in transgenic sugar beet. BMC Biotechnology 4;31: 12.
Van West P, Kamoun S, van 't Klooster JW, Govers F (1999) Internuclear gene silencing in Phytophthora infestans. Mol Cell. Mar.;3(3):339-48.
Vancanneyt G., Schmidt R., O'Connor-Sanchez A., Willmitzer L., Rocha-Sosa M. (1990) Construction of an intron-containing marker gene: splicing of the intron in transgenic plants and its use in monitoring early events in Agrobacterium-mediated plant transformation. Mol Gen Genet. 220(2):245-50.
Wang Y, Dou D, Wang X, Li A, Sheng Y, Hua C, Cheng B, Chen X, Zheng X, Wang Y (2009) The PsCZF1 gene encoding a C2H2 zinc finger protein is required for growth, development and pathogenesis in Phytophthora sojae. Microb Pathog. 47(2):78-86.
Wang Y, Li A, Wang X, Zhang X, Zhao W, Dou D, Zheng X, Wang Y (2010) GPR11, a putative seven-transmembrane G protein-coupled receptor, controls zoospore development and virulence of Phytophthora sojae. Eukaryot Cell 9(2):242-50.
Yin C, Jurgenson J E, Hulbert S H (2011) Development of a Host-Induced RNAi System in the Wheat Stripe Rust Fungus *Puccinia striiformis* f. sp. *tritici*. MPMI 24(5): 554-561. doi:10.1094/MPMI-10-10-0229. © 2011 The American Phytopathological Society.
Zang M, Wang Q, Xu K, Meng Y, Quan J, et al. (2011) Production of dsRNA Sequences in the Host Plant Is Not Sufficient to Initiate Gene Silencing in the Colonizing Oomyzete Pathogen *Phytophthora parasitica*. PLoS ONE 6(11 ):e28114.

* cited by examiner

SEQUENCE LISTING

```
<160> NUMBER OF SEQ ID NOS: 49

<210> SEQ ID NO 1
<211> LENGTH: 1042
<212> TYPE: DNA
<213> ORGANISM: Phytophthora infestans

<400> SEQUENCE: 1

cgtcaagatg ctgcggaggt ctgtgctgcc gttggcacgt cgtgccttcc cgcggtccgc      60

ggctagccta gcgccgtcct gtgctgctcc caagtacttt tcacgtgcct tcagcgttgc     120

ggagcagagt cagcggcatg tgatcgccgc gctggttgtc aaccagcctg gttgtctggc     180

cgagatcgcc aacctcttcg ccgctcgagg taactatcga tacgcaaaga cgctggccac     240

aggagatcct aaacatggtg tgatgcaggc tacaatattg acagtctggt tgtgggtcgc     300

acggaggtcg aggagctctc ccgtatgacg gttgtcgtca acggcactgc gcagagtgtt     360

gtcaacgtac gtatagtaat tacagagaca ggagcagtag gtgattgaca ctcaatgtgt     420

ctttgcagat gaagaagcag ctcgaggatg tcgtgtatgt tgctgtggtc aatatcctga     480

gcagtggcaa gaacgctgaa aagaactacg tcgagcgcga cctgatgctg gccaaggtgt     540

ccacggccgg tacgtcggac gctgatctga taccctacca ccaccggaat tcgtgaacat     600
```

-continued

```
ggacctgacg taaacatttg ctggtgtgtg tgctggctac agaggctgga tctcgcgctg    660

aggtggtgga gcttgccaac ctgttcgacg ccaaggtgat tgacgtgcga ccgcaccagg    720

ttatggtaca actggctggc acccctggtc gcattgaggc atttttggac ctgctaaagc    780

cgctgggtat cacagagatc caccgcagtg ggtcattgc gatggctcgc agcaccagtg    840

tgaccgacga cctgggcgat ctctcgacgt ttgagggcgc cacgcgaacg cttctggacg    900

aggccgatga cgaagagttc gatgtctctc gccttccgcc tggataatat gttggtagag    960

ttatgatcat gccatcacct ttttcttcga taggacttgt gcctgatgac aattgcagca   1020

aggaacgtgc tagcgaagat tg                                            1042
```

<210> SEQ ID NO 2
<211> LENGTH: 3072
<212> TYPE: DNA
<213> ORGANISM: Phytophthora infestans

<400> SEQUENCE: 2

```
atggtgctcc gagcggttcg gctgatcgtc caggcatctc tgctcctgca agtgctccag     60

tgtggcgcct ccgtaactgg tgctcaagta aatgaaaact ttgagaacac tgagcttacc    120

tcgaacgata aactgggaac agtggctccg gccgacatcc cgtcttcaca agacgagaat    180

ctcaagaaac aggaagagcg tggcttcttt gactggtttg gcaatggcga cgacacgcct    240

gccccggctg ctgacgacaa ctccggtaaa tatgcgacta cgacaccgat ccctggcacg    300

gctgcgcggc cgtctacgag tagtctgatg tcaaagtatg gtagtatgct cggtgacttt    360

actaaagaca cgacgccggc ctcggaagcc gatgagcgca caacgagcgc acgtagcgct    420

gccacccgtg ccacctcgga ctcctcttca ggtagtacct ctggcagcgc ggcagcagaa    480

gtcaagccga agagaaagaa gaccaagaag cctgtggttg ccgccgcgtc tgaaagcgga    540

gagagtgcaa gtgacgacga tgccagcgag gcgagcgctt cgggcagtga ggcaaagccc    600

aagaagagga caaccaagaa gacgaggaag ccggtcgtag ctgctgcgtc gacgtctgaa    660

tccgaggatg cctcgacgtc tgaatccgag gatgcttcgg gcagtgaggc aaagcctaag    720

aagaagacaa ccaagaagac tagaaggccg gtagcagctg ctgcatcgac gtctgaatcg    780

gaggatgctt cgggcagctc ggacgagtcg ggaagcgacg atctgtcgga tctgctcggc    840

agctcggcgg gttccggaag cgaagatgac atgtcggccc ttctcggtag cgcgggaggt    900

tccgggactg acgacgcctt atcagctctg ctggggtcgg gagtcggtgg ctcgggtagt    960

atgcttagtt tcgaagactt tatgaagaat tacggtagca tgttcggttc gggaagtagt   1020

gctgtcgacc tgttcggaga cccgagcacg ccccagaaca acacgattga cgacgaagat   1080

atcatcctcg gcgaactgta cggtggcaag gagcacggcg acgccttctc ggacatcagg   1140

aacatcaagt ttggtcagat gatcctgaac attacagttc gcggtcaaga gcgcgtggat   1200

tccattggta ttacagtgat gactcaagaa gctgttggta accttgtgca cggtggtgaa   1260

ggtggtaccg aaggattcat tgaaccggag atgggtgaca ctattgatac cgtcgaagta   1320

cactgggaca agaacaaggg caagacgtgc atcttctacc tcaagatggc gacttctggc   1380

ggtaagacga ttgcgacggg aacgaagacg gccaacagcg ccgtcatcaa gccgcccaag   1440

ggctaccagc ttgctggatt ccatggtcgt gccagtagtt ctggtatctt ttgtattggt   1500

ggaatcttca ccaagcaaga cgcgacggat ctcgcagtca cggacgtgat ggccatctcc   1560

agtaagggct ctcctgatat ctacaactac gacaccacca ttcgtaactg ggtgggacct   1620

ctagagacag cgagtgacaa cgcctgttac cagaagagag tcgacgtcag cagcaaggga   1680
```

atgtgtccgt cgggtttcaa caaggacgac gacaggtgca tcacccaatg tcctctcaac 1740
taccccattg actgcttgat ggagtgcatg cctcaaaaca gtgactgcac ccagttgatt 1800
gtcgctaagg tttccgccgt cgttgctgtc gctttaaatg ccgctacgat gggtatcttc 1860
ggtacgctgg tggctgccta cagaaccgct aactttgctc tcacctgcgc catcaacgtt 1920
gtgaacgctg tcaagtcgct gatttactac ctgcgttaca agcagacctt gatcccgact 1980
acggacacgg agaagttgat ggacaaggcg ttccagctgc agattgtcat tcttgacttg 2040
cctctggcta tctgttcttg cctgggcatc aagattcctc ctaagctcca gttctcggct 2100
accattctgg ctgtcgtgtc ggccattgtc atgatggctg tcatggtcgg tgaggccctc 2160
ttcgcgtcgt cgaacaacgt catgctcatg cttcgtgagt cgggcgcttt taacacttct 2220
gctctgaacg gagacaccat tgagcttgat acgttcctca acaccaagaa cggcacgtgt 2280
ggttacgaga tgagaactct cactaaccgc gtcatgggca aggtctacga aatccgtaac 2340
aacacgccga atgctgatgc cgatgatgta cgtgttgagg tgagcaagtc gtccatcatt 2400
acggatgaca tccccattgt gaccaaccac tgcatgggtg atatctggac caacaagacg 2460
ggcgcgtcgt cgtacaagac gcgcaacctg ctgcgtaaga ccctcagtgt aattgttgac 2520
cagctcgttg aggacggtac gaccgatatg ggtaagcatg tgaccaagaa ggagaaggct 2580
ctcgaatact cgaatatggg tcttttcgtg ctgtccatgt tcgatccgac gggtattgcc 2640
tggatggctt ccgagttcgt gcagcccatt tgtggaccca ctgagtacct gggtgagatc 2700
gatgatggta cgctgtacga cgctctgggt ctaaacacgg tcgaccaggc gttcctggga 2760
agctacggtg tgtggaagaa gaagggtgat ggctccgtca cggtttactt cgagagtgtt 2820
gacaagttcc ctgtgtctgt ggtgatcacg tccggtggtg acaagctcaa ggaggtcaag 2880
gtgcctgcta acggcaacgt cacgtggaca tctacggtgg aggagcttgg tgacaagact 2940
ctttaccttg accgctggcg tcctggtctc tttggcctgc ctggtacggg cggtggttcg 3000
ctactgatgt ggatcccgcg atcgtctgag ggtggccagc ttgttcttca tgctcgcttg 3060
aatgttagct aa 3072

<210> SEQ ID NO 3
<211> LENGTH: 2405
<212> TYPE: DNA
<213> ORGANISM: Phytophthora infestans
<220> FEATURE:
<221> NAME/KEY: modified_base
<222> LOCATION: (949)..(1048)
<223> OTHER INFORMATION: a, c, t or g

<400> SEQUENCE: 3
atgtcatccg tagacttgag tatcctgcgc aacggcatcc cggccgagct gccggcgcac 60
ccgggcaacc accccgaccc gacgctgccc aaggctccgc accgcaacat cgacggtctg 120
tccaaggacg atctcgtgct ggccgtgcag aacgcgttac ggtacttccc cgagaggttc 180
cacgccactc tggctcccga gttcgcgcag gaactcaagg acgagggcca catctacatg 240
caccgcttcc gtcccgtgca gtacgagatg aaggcgtacc ccattgacca atacccggcc 300
aaatgcaaac aggcagctag tatcatgctt atgatcatga acaacctcga ccgtcgcgtt 360
gcacagttcc ccaaccacct ggtcacttac ggtggcaacg gtagtgtctt ccagaactgg 420
gcacagtact tggtggccat gcgctacctg tccgaactca cggaacagca gacgctcgtc 480
atgtactctg gtcaccctat gggtttgttc cctagtcgtc ctgcagctcc acgtatggta 540

-continued

```
gtgaccaacg gtctaatgat ccccaactac tccacacgcg ctcagtacga caaggcctac    600

gctatgggta acacccagta cggtcagatg actgctggca gctactgcta cattggtccg    660

cagggtattg tacacggtac gaccattact gtactgaaaa cctactgacg aggtctatgg    720

cggttcagat gagagcaatc taccttcctt ctagaaaaat gctaaacaat tccagtggat    780

gttgtatagg tcttgacaat caatattgcc ccctacgatt ttgtcaatat taacaatcag    840

tttatttctt ccaatccctg attttacagt gaggatttcg agagtgggaa cgtggaaaca    900

aaatcattgt caaatttgag cgagcctttc tcgccgatgc cagactggnn nnnnnnnnnn    960

nnnnnnnnnn nnnnnnnnnn nnnnnnnnnn nnnnnnnnnn nnnnnnnnnn nnnnnnnnnn   1020

nnnnnnnnnn nnnnnnnnnn nnnnnnnngc gtcatctccg gtgtcatctc cgtcactgca   1080

gagatcgacg aatctgcagt gaagaagcgt cacgaacagg gctgggttga cgaggtcgtg   1140

agcgacctgg acgcctgtgt cgttcgtatc cgtgaggcaa aagccaaggg cgaggtggtg   1200

agcttggcgt accacggcaa cgtcgtcact ctttgggaac gtctcgccga cgaggctgaa   1260

gctacgggcg agctgctcgt ggagctcggc tcggaccaga cttccctaca caacccgttc   1320

aacggcggct actacccggt ccagttgtcg ttcgaggagt ctcagcgcgt catggctgaa   1380

gacccggagc gcttccagga actggtacag gagtctctgc gtcgtcacgc tgtcgctatc   1440

aaccgtctga cagccaaggg catgcggttc tgggactacg gtaactcgtt cctattggag   1500

gcacaacgtg ccggcgcgga cgtgttgcgt cccggtgtta agcccgagga ggctgctgtc   1560

tcgactactg cctttaagta ccctagttac gttcaggaca tcatgggcga cattttctcg   1620

cttggtttcg gtccgttccg ctgggtctgt acgtcgggtg accacgcgga cctgcagaag   1680

acagacgcca ttgctgcccg tgtgatgcgc gagctgctgg ccgaaccgga agtgccggac   1740

cgggtcgcgg ctcagctgcg tgacaacttg cgctggattg aggctgcaga ggagaacaaa   1800

ctggtcgtgg gatcggaggc gcgtatcctg tacgctgacc gtgtgggtcg cggcacgatc   1860

gccatggcgt tcaacgccgc tgtggctagc ggcgagctct cggcacccgt cgtgctcagc   1920

cgcgaccacc acgacgtcag cggcaccgac agtccgttcc gtgagacgtc gaatgtgacg   1980

gacggctcgg ctttctgtgc cgatatggcg gtgcagaacg cgctgggcga cgccgctcgc   2040

ggagctacgt ggatcgcact gcacaacggc ggcggtgtcg gctggggcga ggtcatgaac   2100

ggtggcttcg gaatggtact ggacggctcg gatgacgcgc gcgagaaggc ggcgtgcatg   2160

ctcggctggg acgtcaacaa cggcgtggca cgtcgtgcgt gggcgcgcaa cgccaacgcg   2220

cgcttcgcta ttgagcgcga gatgaaggcg gaccctttgg tacgtttgtt tggttacgag   2280

cttgagactt tggaagcgtt agattttaat gtgtgtgtat ctttgtggta ttgcagctga   2340

cggtgacgct ggctaacgag gccgacgacg cgagcgtgcg tgacgctgtg agcaagctct   2400

tctag                                                                2405
```

<210> SEQ ID NO 4
<211> LENGTH: 1735
<212> TYPE: DNA
<213> ORGANISM: Phytophthora infestans

<400> SEQUENCE: 4

```
atgctctcgc agcttaaacg cagattcacc ctgggacgac gttgtcagac cgaagaagaa     60

gaccactcga ggatcaccat gagcctttcc aacagcaaca gtaccagctc cttgcccccct   120

gtggacgagc accacggctg tgagtacctg gatacggcgc tgacgatctt tgtaatcggc    180

gcgtcgggcg atctggccaa gaagaagacg tatccgtcgc tctttgcgct ctacaccatg    240
```

-continued

```
ggctacctgc ctgaacacgc ggtcatcgtg ggctacgctc gcagcgccaa gaatgatgcc    300
gacttccgcg cgcaaattgc gccctggatc aagcctaaga cacccgaggc cgaggctcgc    360
aaggaggcct tcctcaacaa gtgcatctac cgcagcggca aatacgactc aactgaagat    420
gtgggcaagg taagcaagga gatggaggca ttggaagaag cccatggatc gcctgtggcc    480
aaccgcctct tctacttcgc catcccgccc acagtcttcg tgcccatcgg cacgagcatc    540
aagaaggcgg cactgaccac gcgtggttgg aaccgtctca tcgtcgagaa gccatttggc    600
cacgatctcg actcgttcga caagttgtct caggacatgg gcgcgctgta cagcgaagac    660
gagatctacc gtatcgatca ctacttgggc aaggaaatgg tgcagaactt gctcgtgttg    720
cgcttcggca atgcaatctt cgagcccatt tggaaccgca actacgtgtc cagtgtgacc    780
atcactttca aggaagacat cggcactcag ggccgcggtg gctacttcga ctcgttcggt    840
atcatccgtg acgtcatgca gaaccacctg cttcaggtgc tgtcacttgt ggccatggag    900
ccaccaatcc aagctgctgg tgacaactac tccaactata tccgtgatga gaaggtcaag    960
gtgcttaact gcattgagcc tatcaagatc gagaacaccg tcctgggcca gtatgaaggc   1020
agcaaggagc tcaacgagcc gggctacctc gaggacccga cggtgcccaa gggatcagtg   1080
acccccacct tcgccacagc tgttatgtat gtcaacaacc cgcgttggtc tggtgttccg   1140
ttcatcatga aggctggtaa ggccttgaac gaacgcaagg gtgagatccg tgtgcaattc   1200
cgcccgcctc ctggagcgca gcacttgttc ccaggtgtca agatcccagt acaagagttg   1260
gtgctgcgtc tacagccgga ggaagccgtc tacttgaaga tgaacgtcaa gagtcctggt   1320
ctgcagaccc aggcgatctc aagcgagctg gacttgtcgt acgccgagcg ttacgagggt   1380
gcagaggtgc cggacgccta cactcgcttg atcctggacg tgctgcgtgg taagcaggcc   1440
gcattcgtgc gtgatgacga gctccgtgct gcatggaaga tcttcacgcc attgctgaac   1500
gagattgaga cgcagaaggt gaagccgctg cagtatacgt tcggctcgcg tggccccaag   1560
gagagcgacg agctggtgaa cagagctggc ttccagtacc accagggcga ataccagtgg   1620
cagccgcgtg tgcgcactac cagtgcacta taggttgtct ctttggttga gcacaaagat   1680
gcccggaagt ctggcataaa tatgatggtt gagccagcta gtcttcaata aggga        1735
```

<210> SEQ ID NO 5
<211> LENGTH: 1245
<212> TYPE: DNA
<213> ORGANISM: Phytophthora infestans

<400> SEQUENCE: 5

```
gggagcttaa aagtgctaca ggaagtcgct atcatggcgt caagaagtct cgtccgccgc     60
tcggcgcgtc tcgccactgc catcgctact aagcgcagct tcgttcgcgc cgcttccgcg    120
tcggtgaacc tccagtgctt tcagacagca cccgccactc gccagacccg tcttcagagt    180
acgcagacaa gctccagcga tgagccgccc aaaacggagt ccccagtaga cccagagcag    240
ctcattctgg ccaaggctct ggaccatgtg atttcccacg ggtacgttat ggtttaagtg    300
ctataaaagc gaagatatcc taggttgtaa cgctctcgaa tgcaaggtgg gccattgagg    360
ctctagcagc tggcgccacg gatcttggct acccttcggt ggctcacggc atgttccagc    420
gcggagctat tgatttggtg gattatttta tggactcgtg tctcgccaag ctacgcgaga    480
cgctgattgt caacacggaa aagttgcagg ccatgacggt gactgaacgt ctcaagtttg    540
gcgtctgcac gcgtctgcag atgctggagc ctgtgttggc tacatggcca caggctatgg    600
```

-continued

```
ccattggcgc tctaccgcag aacgcacctg gtactgcaaa gagactggcc cagctctcgg     660

atgaaatctg gtacttcgct ggtgacaagt ccacggatct atcatggtac accaagcgcg     720

ctattctcac gggcatctac gctagcacgg agctgtttat gctgaatgac aagtcgccga     780

acttccagga cacgtgggat ttcttggacc gccgtgtgga cgaaacgatc caactcggag     840

aactgcctca gaacgtacgt gaagctgttt gagtctctta taaggcttag ctgttgacgt     900

gactaactac ttgtgtgctg gtctgtgtct gagcagctga acgatgtggc tgggatggcc     960

agtattgggc tgcagtcggt gttttcggct gtgacgtcgc ttgcgggtcc tctggccagt    1020

cagatcatct cgaactcgcc tttgagtcaa gttccgaacc cgatttcagc tgtgggcagt    1080

gtggttcctc cctcggttgt atcggctgtt gcctctggaa tgccatttag caatcctact    1140

tctgctggac atgacggtat ggcgttcaag tcgaaggatc tggacgaaat taaccaagag    1200

cttgagaagc tcggcggcct tgacgcgagt gaacgacgga actaa                    1245
```

```
<210> SEQ ID NO 6
<211> LENGTH: 1461
<212> TYPE: DNA
<213> ORGANISM: Phytophthora infestans

<400> SEQUENCE: 6

ccacgtccag ctcaagccaa ttgccatgct gtccgctact cgccgcctta cgcgatctct      60

gcgtcgccct tctgcactgg gatgccgcct cgagtcctca ttcgctcccc tcactcagct     120

atccgaggag gaaaccatgt tcaaggacac agtcgcccgg ttcgcggctg acgtggtagc     180

tccgaatgtc cgcgccatgg acacagcggg ggagatggac catgctatca cacgaggact     240

attcgagaat ggactgctgt cggtagagat cccagcagac tacggaggta gcgaggcctc     300

gttcatgaac ctctgcttga ctattgagga gctgtccaaa gtggatcccg tcgtgggact     360

gctcgtggat ctacagaaca cagttgtgaa caacgtcttc ctggtgagtg aagagtacga     420

ttggtattct aaattctgta gctgaccatt gtgttgcagg tgcacggcac ggacgagcag     480

aaagaaaagt acctgccgag actcagcgcg gacatggtgc gtgcatcaat atttggaaat     540

attgtgataa tactaatatt gtacggtgtt gtagatcggc agtttctgtt tgtcagaggc     600

tggatcaggt agtgacgcgt tcgcgctgaa gacacgggcg gaggcctcgc cggacgggag     660

ctactactcc atcactggtc agaagatgtg gatctccaac gccgagtact ctggcgtgta     720

cttggtgttc gccaatgtgg acccgtccaa gggctacaag ggtatcacgt gctttatcgt     780

ggaccgagac atggaaggac tggagatcgg taagcccgaa gagaagctcg gcatccgcgc     840

atcgtcgaca tgtcccgtca cactgacgga tgtgaaggtc ccgaaggaga acattctggg     900

agagctgggc aagggataca agatcgcaat cagcacgttg aatgaaggac gcattggcat     960

tgcgtcgcag atgctgggac tggctcaggg agtctacgac cagacgttgc cgtacttgtt    1020

cgagcgccaa cagttcggct ctcccatcgg agagttccag gcgatgcagc accaatatgc    1080

ggaggcagcg ctcgatatcg agacggcgcg tttgttggtg tataacgcag cgcgtctcaa    1140

ggatgctggc caaccgttcg tcaaacaggc tgctatggcg aagcttcatg cctcgcgtgt    1200

ggcagagaag acggcatcca agtgcatcga gctgcttgga ggcattggct ttaccaagta    1260

cttgcttgcg gagaaattct atcgtgacgc aaagatcgga gctatctacg aaggaaccag    1320

taacatgcag ctgacgacga ttgcgaagct tgtgtcggag gaatacaaga ggtaattgaa    1380

tgtcgtgatc ctgtactcag acttgatcct tgtagcaaac caaacaagta acatttccgg    1440

agaacgagcg ttagaaccag a                                              1461
```

<210> SEQ ID NO 7
<211> LENGTH: 1580
<212> TYPE: DNA
<213> ORGANISM: Phytophthora infestans

<400> SEQUENCE: 7

```
atgctgcgtc gtcttgccct ccgtaccgtg aagccttctg tgcgcaactt cgcctccgcc     60

tcggagctgt acaagaaccc gcgcagctcc aagttcagca tgaccaagat cgtggccact    120

atcggccccg tgtcggagca gctggacatg ctacagaaga tcacggacga aggtttgcgt    180

atcatgcgca ttaacttctc acacgccgag tacgacgagg ccttgctgcg cgtcactaac    240

cttcgtgcct gtcgcggcgt gcacgccgag ggtcaggcca aattcaacct acgtgccgtg    300

ctacacgaca ccaaaggacc cgagatccgt acgggtaaga tgcgtgacgg caagaaaatc    360

acgttagaga gtggcaagtc ggtggtgctc acgaccgacc cggctttcga gcttgagggt    420

accgccgaca agttctacgt tacgtatcag cagttagccg aaaccgttaa ggtgggcgat    480

acagtgttac tatctgacgg ccttatccgt ctcacctgta cgtcagtggg taaggatgag    540

attacgtgcc acatccacaa taccgaggaa atcggtaacc gtaagggtgt aaacctcccg    600

ggtttgatcg tcgagttgcc tgctctatct gataaggaca aacgcgacct ggattggggt    660

gtcgagcacg atatcgactt tatcgcggcc tcgttcatcc gtaaggccag cgacgtgaac    720

tcgatccgtt cgttcgtggg agagtgcgtt aagaaacact ggggtaacca acctggttac    780

attgccccta agatcatctc taagatcgag aacctcgaag gtatccagaa ctttgaggag    840

atcctcgagg cctcggatgg catcatgtgt gcccgtggcg atttgggtgt cgaagtgccg    900

gcacagaagg tcctgacata ccagaagatg atggtggacc gctgtaacgc cgtcggaaag    960

ccggttattg tggcgacgca gatgctcgaa tccatgcaga acaacccgcg ccccacgcgt   1020

gccgaagtgt cggatgtcgg caatgccgtg ctggacggcg cggactgcgt catgctcagt   1080

ggcgagtcgg ctcagggcaa gtacccgatc gagtctgtgg ccacgatgaa cacggtgatc   1140

aaggaggccg accagctcct actcaagcct aactaccagg ccaagttcca gttcgagccg   1200

cccacgtcgg acgtcgagtc agccgtgtcg tcggcagtca agacggccaa cgagatgcac   1260

gcgcagctcc tgattgtgct cacccgtacc ggttacacgg cccgaaaggt cgccaagtac   1320

aaaccgactg tgccggtcat gtgcttcacc accgacctta aggtcggccg tcagctccag   1380

atccaccgcg gtctgtaccc ggtggtgccg gactaccttg accgtgcccc gactaccgcg   1440

gaggccatcg ctcacgccaa gaagatggga tggttgtctg ccggcgaccg tgtcgtcgtg   1500

atcagcggcg acaagctgtc ggacgatctc ggccgggaaa tcctcatcgg cgtcgctgac   1560

gtccagtaag acggagacaa                                               1580
```

<210> SEQ ID NO 8
<211> LENGTH: 900
<212> TYPE: DNA
<213> ORGANISM: Phytophthora infestans

<400> SEQUENCE: 8

```
atgtggtcga cgatgatcat gcggttccct acgcaggcca agtccgtgtc gcgcagcgcg     60

cttgtggcgg caggtatggc tgcgttcgct gccttctcca gtgtttcctc tactcgctgc    120

gaagaggaga agtccaaggt ggcgttgagc cccaaggagt tccgttcttt cactgtgcgt    180

aaagttgaga ccgtgaacta caacacgaag cgcgtgacgt tcgctcttcc cacacccgag    240
```

-continued cacgagatgg gtctcacgac gcctagttgc cttatggctc gtgccaaggt agacggcaag 300
acagtggtgc gcccctacac gcctgtcaac gtgaacgacg agaagggttt cttggagctc 360
gtagtcaagg gttacccaca gggaaagctc agcaagcaca tcgtgcagct caaagaagga 420
gactctcttg acatgaaagg tccctttccc aagttcaatt actaccccaa caggtacaag 480
agcatcggca tgatcgctgg cggctccggt atcacccca tgctgcagct catcaaggcc 540
atttgccgca acccggagga ccgcaccgag atcacgctgc tgtactgcag tgtctcggaa 600
gaagatatca tcctgcgtga agaagtggag gccatgatgt acctgtaccc gcagatctcc 660
gtgatccacg tgctcagcaa cccgtccgcc gagtggaagg gtcttacagg cttcgtgtcc 720
aaggagatga tcgaaaagta catgccggag ccgtcagacg acaacctcgt gtgtgtgtgc 780
ggtcctccgc caatgatgta ccacgtctcg ggtgacaagg cgaaggacag gtctcagggc 840
gaactgcaag gtctgctgaa agacatgaac tacacctcca ctcaagtgtt caagttttaa 900

<210> SEQ ID NO 9
<211> LENGTH: 1245
<212> TYPE: DNA
<213> ORGANISM: Phytophthora infestans

<400> SEQUENCE: 9
gtcgagcaca agaccaacac tcctgcacca tgactaccct caagatcgtc gtttccggcg 60
ccgccggcca aattgcgtac tcgttgctgc ctctcagtac gtccgtctcc ttccctcttg 120
tgtcttctcc ataccctaac gtctcaccat gttgcagtct gcatcggcca cgtcttcggc 180
cccaaccagc gcgtggagct gcgcctgctg gacatcgaac ccgcccagga agcgcttgag 240
ggcgtcaaga tggagctcca ggactgtgcc ttcaacctag tggacgctat catccccaca 300
gccgatctgg agactgcttt caaggacgcg gacgtcgcaa tcctcgtggg cggcttcccg 360
cgcaagcaag gcatgcagcg caaggatctg attgagaaga atgtagccat ttttaaggct 420
cagggagctg ctatcgacca gttcgccagt cgcgacgtta aggtgcttgt tgtggccaat 480
ccagccaata cgaactgcct cattgccatg gagaacgcac ccagcatccc gcggcgcaat 540
ttctcggcac tgacgcgtct ggaccatgag cgtttgcgct cgttcctagt ggagaaggtc 600
aacgagaccc aaagcccgaa agttacgtcg aaggacgtca acaaggtcgt gatctggggc 660
aatcactcga gcacgcaagt gcccgacgtc acgaacgcag aagtgaaggg ccagccgctt 720
gataagatcg tctcggacaa ggattgggct gagaagaagc tcgtcaagga cgtgcaggag 780
cgcggtgcag ccatcattaa ggctcgcaag ctctcgagcg ccatgtcggc tgccgccgct 840
atcggcgccc acctgcgcga ctggttcaat ggctccaagg acggcgagct cgtgtctatg 900
gccatttgct cggacggcaa caagtacggt gtgcccgagg ggctcattta ctcgttccca 960
gtcaagtgcg cgggcaacgg cgcgtacgag gtggtgaacg gtcttcccat ctcgccgcgt 1020
atcgacgcaa tgatgaaagc cactgcgcag gagctgacag aggagaaggc cgacgctgtg 1080
gagatcctgt cgcgccagtg agcagtattc agctaatagc tggacgatgg caacgtcgtc 1140
tacaccccat tcgatttttt tctcccatta tgagctgctt caatcgttta tttgaccatc 1200
taaaccaatt aatttcttgt tattacgatt tcttattgaa aaaaa 1245

<210> SEQ ID NO 10
<211> LENGTH: 1280
<212> TYPE: DNA
<213> ORGANISM: Phytophthora infestans

<400> SEQUENCE: 10

-continued atgtcgtctt cattttgtca gctatccaag cgcgtgctgc agtatcttcg acatgagcat 60
ccacatcgtc tatttccctc catcggtcga agacgcaaac tcccaggcat aaacctcgac 120
ggaagatctc agcggtgatg gcgcgtggtt agccgcaagg tgttccgatg cacaccacac 180
actactcgcg aaaacgacca tacttctgtc ggccagggta acctctgggg agctgcacaa 240
cggccgtctt tttagcttat tttagcgagc caacaggttg tgcctcattg gccacgtgtt 300
cacgcacgta cgtcacgtgt gtgctcattt taatattaaa gatcccgttg aagacgaaaa 360
gcttctttgc tggcatcatg cgcttccaga cgttgttgct cgtccttgtc gcactagtca 420
tcgccccgtt tcaggccctg tctccaccca gcgagtccaa cgtgccgttc actcttcggt 480
acgtcccggg cttctttaaa caaggtaccc cgtccgtgga gattccacct tcaaattcaa 540
ggcatctcgg gctacttgac aacgtcacgt ggacggatgt agacgcctac attgctgcac 600
gagccgctca aggcgtggac gtcaagttgt tcctcttctt acgtcatgga gaaggcctcc 660
acaacgtcgc cgaagccact tacggcaccg aagcctggga cagattctac agcaaactag 720
cgaaatatac tgacgccaag ttgacgaaac ttgggatgca acaggctgtc aaagcgtcgg 780
aaaggatcga cgaggagctt aagagaggac tgagcctgga ggaagtcgtg gtttccccgt 840
tggagcgtac actacatacg gcaatgatcg cgtgccagaa tcaccacgag atcccgaagc 900
ggtcgatgga atggccccgc gagaccatcg gcgtctgcac gtgcgactta cgcggcacca 960
tctccgccaa ggccgagctg tacccaagta tcgacttcag tgatatctgg agtgatgcag 1020
acccgtggtg gacgcctgat catcgtgaga ccgagctgca catcaacgac cgcgctcgca 1080
tcttcctgaa ccgcgtcttc tacggtcaca agtcagtgcg tgttggtgtg gtgacgcaca 1140
gtggactaac caccgccgcg atgcgtgtca ttggccatcg taagtacagt gttgcgacgg 1200
cggaagtgat accgttcctg cttgaagaca ccacggtgca cacgatcctg tcgatcttct 1260
ctggtaaaga agacatgtag 1280

<210> SEQ ID NO 11
<211> LENGTH: 1016
<212> TYPE: DNA
<213> ORGANISM: Phytophthora infestans

<400> SEQUENCE: 11
atgtcgtcct atcgtgctgt ccaagttgta aagttgacta aggacttccg cgccgctacc 60
agaatcgtga gtgtccccga actacccacc gctgggcccg acagcatcgt tgttaagaac 120
cgcttcttgg gaattaactc gaccgacgtc aatcttacga atggcatgta tcatgacaag 180
ctgccgtttc tcgcgggcgt tgaaggtgca ggtctcgtca ctgaggtcgg gagtaacgtc 240
acgactgtga aagtgggcga cgctgtcatg taccagacgc tgggagccta tgcggactac 300
gtacaagtgc ccgtgtcggc cgccatcaag atcccagagc tgtcgaagaa cgctctaccg 360
gttgcagtgg gcggcgtctc tgcgtccatc tgccttgaat gtctcggtga gatgaagtcg 420
aatgagaccg ttcttgtgac tgctgctgct gggggaaccg gacagtttgt cgtacagctc 480
gccaaacttg ctggcaacca tgttatcggc actaccagct ctgacgagaa agtggaggct 540
ttgacgaaac tgggctgcga ccgtgtaata aattacaaca aggagaatgt cggcgatgtg 600
ctaaagaagg agtatccgaa tggagtagac atcgttttcg agtccattgg aggcgacatg 660
ttccgtgctg ctgtcgataa cattgcagtc cgtggtcgta tcatcaagat tggcttcatc 720
tcgcgagtat tggagaccaa agacaagacg actccccaag gccgcctccg ctgctatcgt 780

-continued gggaagcgaa caagaagatt ctgatgaagt ctgcttccat ccgagggctc ttcatgtatc 840
actttgagga acacattcga gagcacacgg agcgattgct gaagctcatt agcgagggca 900
cgttgaagcc tggcgttgac cccactacgt acaagaaatt cgagtccatt ccgaatgcaa 960
tcgaccgcat gttcgcccgt gaaaatgtag gcaaactcat cgtagagctc gagtag 1016

<210> SEQ ID NO 12
<211> LENGTH: 267
<212> TYPE: DNA
<213> ORGANISM: Phytophthora infestans

<400> SEQUENCE: 12
atgggcaagc acacggagcg agccaaggag agtccattca agcagcagtc gatgatcctc 60
gtgcctatgg acacaccagg cgtgcaggtc gtgaagccca tgcatgtctt tggctacgac 120
gacgcaccgc acggacacat ggatatgctg ttcaaggacg tgcgtgtgcc gttcagcaac 180
gtgttgctcg gtgaaggtcg cggctttgag atcgctcagg atcgtcttgg acctggccgt 240
atccaccact gtatgcgagc catctga 267

<210> SEQ ID NO 13
<211> LENGTH: 1147
<212> TYPE: DNA
<213> ORGANISM: Phytophthora infestans

<400> SEQUENCE: 13
atgcgcaaaa tattgaatat tgattggtta aaacctggtc ttggcatcct tatgaccaat 60
tacagttatt gagtgcttta agcggggcag acgtccacta cgtcacactc agaatctcca 120
cacaagcaac agaccgacac aatgagcagg tgcgagtggc atcccagcaa cttcgtgcaa 180
atttagcctt gttatattaa ttgtataacg tggcatgttg cagaccgacg atctcagagg 240
ttatcgccga gcggaaggcc aacaacactg cggctttcat caccttcgtg ccctgcggct 300
tcaagactaa ggctgacaca gtggacattc ttctgggact gcagcgcggc ggcgcgaaca 360
tcatagaggt gggcattccg tactcggacc cacaggccga tggcccgacc atccagcgcg 420
cacaccaggt gggcgtggac cagggcatca cgctgcatga cgtcctggcc acagtgagcg 480
aggcgcgaac taagggcctt actacgcctg tggtgcttat gggctactac aacaacattt 540
tgcagtacgg cgaagtcaaa atctgccccg acgcccagaa aggtacgcct gtaatcgacc 600
acaggagaga tttgtgggct caaaaactga caataaacgt atttgtagct ggggtggacg 660
gattcattat tgtggacctg ccgcctgagg aggcaaagac gctcagtgac gacgcagcta 720
agcacggact tgcgtacatc ccgttggtgt ccccaacgac gacggaggag cgtatgaagc 780
tcatcgactc ggtggcacat ggttttgtgt attgcgtgag tctcaccggt gtcacgggcg 840
ctcgtaacga gctgcctccg aacctcgacg cgttcatggc caagagtaag ttgcttttcg 900
cgctttagtt tattttaatt gtcgagctaa cgtggtccct tgattcgctg cagttcgtgc 960
caacgtgaag caccctctcg ctcttggctt cggtctgtcg acccgccagc acttcgttca 1020
agccagcgcg cttgcggacg gcgttgtgat cggctcgaag attgtcaaga tcatcgagga 1080
cgcgcctgac acagccacgc gtgctgccaa tgtggaggca tttgccaaga gcatcgtgaa 1140
cccttag 1147

<210> SEQ ID NO 14
<211> LENGTH: 1917
<212> TYPE: DNA
<213> ORGANISM: Phytophthora infestans -continued

<400> SEQUENCE: 14
atgggtaaca tcctggagga gatcgcagcg cagcgccgtc tggacgtggc ggccgccaag 60
caggtcatat ccgccgatga tctggccaag aagatcgagc acgcggaggt cgttttcggc 120
tcgaccctgc ccgtgcttga ccgccttaac gcacccacgg tgcgtccggc agtgcaggga 180
atctggagaa gaatctgcgt ctaacgcagc taccgctgta ctgtattttt tccttgtatt 240
tatggcagag agaggggtgg tccgacgtgg ctctggctgc cgagtttaag cgtgcgagcc 300
ccagcaaagg tgacatcgcc acggagctca atctgcgtga gcaagtgcag gcctacgcca 360
acgcaggtgc cagtatgatc tccgtactga cagagcccaa gtggtttaag ggatcgctag 420
acgacatgag ggcagcccgg gaggtggtcg agggcatgag tcagcgtcct gccatcctgc 480
gcaaggattt catcatcgac gtgtaccagt tgctggaggc ccgcgcttac ggagcggatt 540
gcgtgttgct catcgttgcg ctgctgtccc aggagcagct tatcgagctc attgacgtac 600
gtcgccccgc ttgcactaca tgtagtgggt ttactgtaca ctgacaagcc tcttgttggt 660
ttgtaggcca cccacaatct cggtatgtgc gctctggtcg aggtgaacag catccaggag 720
ctggacatcg ctctggctgc gagggctcga ctcattggcg tcaacaaccg cgatctccgc 780
acgtttaagg tagacatgaa cacgacggct cgcgttgcag acgctattcg tgagcgtggg 840
ctttcgctgg gacgtgacgg cgttacgctc tttgctctca gtggcattcg ctcgcacgca 900
gacgtggtca agtacgagaa gtgcggcgcc cggggcatct tggtgggcga gtacttgatg 960
aagagtggtg atattgccgc gacggtgaag gatctcttgc agaatgtgac gcgtcacacc 1020
gagtcgggcg aattcgcttt ggctcctccg cttgccaaag tgtgcggcgt cacgacagtg 1080
gagtacgcgc tggcggcctt gcgtaatggt gccaatatga ttggtatcat catggcggaa 1140
cactcacccc gctatgtcca agtggaggaa gccaaggcca ttgcccaggc tgtgtgggag 1200
tatggggagc gcacgggccc tattctctca gacattgtgg agactcactt ggacggcaag 1260
aacgactggt ttcatagaaa tgtccttgcg ttgcgtgaag cttgctcgcg tgcacctctc 1320
gtggtcggag tgtttgtcaa caagacagct gccgagatga acgcgactgc aaaggaaatc 1380
ggactggact tggtacagct acacggcgac gaggggtttc agatctgcag ggacattaag 1440
taccccacca ttcgcgcgtt gcatctgccc gacaccacgc tctgcgacgg cgtggacgca 1500
gaagccgttc tacagcaggt tcaggaaggc cttgccaact acattctgct tgatacgacc 1560
gtgaagggtc agcagggcgg cactggcgtc acattcgact ggaagattgc agccatcttt 1620
gcgcaggcac gacttccctg cctcatggct ggtggcctta cccctgagaa cgtggtgaag 1680
gctctatcgg tcggtcaccc cgttggggtg gatgttagca gtggagtgga agtgaaaggt 1740
tcacctggtg tgaaggatat ggacaaggtg actgcgttcc taaaggctgt gaaggattac 1800
ctctcgattg ctacgcttaa gatcgaggag gagacggaaa cctagagaga gaccctcgga 1860
gtgttctaat caatgagggc cactaatgaa gtgcttttac gttacgagct tggatgc 1917

<210> SEQ ID NO 15
<211> LENGTH: 1494
<212> TYPE: DNA
<213> ORGANISM: Phytophthora infestans

<400> SEQUENCE: 15
atggtgcact atcgtagtac tcgcggcggc gtccgcggcc ttagctttga gcaggcggtg 60
ctgacgggct tggcttccga ccgtggcctg ctgatacccg aagctgacga gttccctacg 120

-continued

```
cttccagctg atgcgctgga gaagtgggcg tctctttcgt accaggaatt ggccgtggag    180
gtcatgcgcc ttttcattga cgaaagcgag atctcgcgtg accagctgcg tgagcttgtg    240
accaagagtt acaacgcgac cacgttccgc tccgatgagg tggcgccggt ggtcaaggtg    300
acggatcaaa tgctggtgct tgagctcttc catggcccca cgtttgcctt taaggatatc    360
gctctccagt ttctaggcaa ccttttcgag tttttcttaa agcgcaagaa cgaggcgctg    420
ccttctgacg ctcctaaaca ccagatcaca gtcgtgggcg ccacctcagg cgacaccggt    480
agctcggcca tatacggtct ccgcggcaag gagaacgtcg aggtgttcat cctcttcccc    540
gagggtcgtg tgagcgccat tcagcagcga cagatgacta ctgtattgga ccagaacatc    600
cacaacgtgg ctgtgaaggg cacgttcgac gactgccagg ctatcgtcaa ggaccttttt    660
gccaacgctg acttcaaggc caagtacaac ctaggtgccg tcaactcgat taactttgcg    720
cgtatcttgg cgcagatcgt gtactacgtc tgggcctact tccgtgctca cgacgagggt    780
gttagcggcg aggttgcctt ctccgtccca acaggcaact tcggtgacat ccttgccggt    840
ttctacgcca agaagctcgg tgttcccatt ggcaagctga ttgtggctac caacgagaac    900
gatatcctgc accgcttttt ctccacagga aaataccacc gccgcgacat cgagcacacg    960
atttccccgt ccatggacat ttgcgtgtcg agtaactttg aacgttatct cttcgctctg   1020
tccggcgaga accacgacat tctacgcggc tggatgcagg ctttcgagca gactaatgag   1080
ctcacgatct cgggcgagct gctctccaag gcacaagacg agatggcatc gtatgcggtg   1140
cttcaggagc aggtgcgctc cactattgcg gagtacaaaa cgatgcatca gtacctcttc   1200
gacccgcaca gcgctattgg cgcagcagct gccatgcact ttgtccagga taaccttgca   1260
gacaagccaa actcggcggt agttgtagtc ggcactgccc actacggcaa gttcctcccc   1320
gtggtgtcga aggcactagg tgtcgctgag tcagagattg agcaacaccc gatcctcaag   1380
gcgctggaat cactgcccac ccggctttcc gttgccagca actcgagtga aactgtggct   1440
gagcatattc gcaagattat tgctgagaag aacgacgaag cctgtagtga ttga          1494
```

<210> SEQ ID NO 16
<211> LENGTH: 1299
<212> TYPE: DNA
<213> ORGANISM: Phytophthora infestans

<400> SEQUENCE: 16

```
atgagctcgt tccgtcttcg tattgccaac gcgcgccaga tcgttcaagt ttgtgcgaac     60
ggcgagccgt ttaagaccgg cgcggcccaa aaggatctgg ctgtgctcga gaatgcgtca    120
cttgtcgtgg acaaggcagg taagatcgcc ttcgttggtc ctgccgctga cgtagagaag    180
tggctgagca cgcagctgca gcccgtgagc tttgagaagg acgtggacgc tcgtgacatg    240
gtcgtactgc cgggttttgt ggatgcgcac acgcacccag tgtggagcgg caaccgtgtc    300
aacgagtttg ccatgaagct ggctggcgct acctacatgg aagttcacga gagcggcggc    360
ggcatcaaca acacggtgcg tcacaccaag aagagttcag aaactgagct gttggagctg    420
ctgcgtacgc gactagaccg catgttgcgt agcggtacga cgcttatcga agcgaagagc    480
ggatacggtc tcgagactga cactgagctc aagatgctgc gtgttttaca ctccgcatcg    540
acgggtgaca acgcacaccc tgtggagatc gtgtccaact acctgggtgg tcactcggtt    600
cctgacggca tgactgctgc tgaggccacg gaggatatca tcacgaagca gattcctgct    660
cttgtgcagg ccaagaagga cggcaccatc tcgcccgaat tcatcgacgt gttctgcgag    720
aagggtgtgt tcgagcacaa cgactctcac cgtattctag aggcaggcaa gaaggcggga    780
```

-continued

```
ttggacatta acttccacgg tgatgagatg tgtccgatgc agtccggtac cttggcggca    840
actctgggcg cccgtgcaat ctcgcactgt gagatgctga ctgctgagga tcttcaggct    900
atggcagcgc acaagccaga gcctgtattc gccgtgcttc tgcctactac caagtatatc    960
ctgaagctgc ccaatccgcc agcacgcgac atgatcgctg ccggtgttcc tgttgctctg   1020
ggcagtgact acaacccgaa cgctcattgc ctttccatgg cactgaccat gaacatggca   1080
tgtgtgctgt tcggtatgac catgaaggag gctcttgtag gcgccaccat caacgccgct   1140
gcctccatca accggtcggc tactcacggc agtctcgagg tcggcaagca gggcgacttg   1200
gtcctgatgc gtgctacgca gtgggagcag atcatctacg aaatgggcga ccctcctatt   1260
gaacacgtag tgaagaaggg agttgtctac acgaagtag                          1299
```

<210> SEQ ID NO 17
<211> LENGTH: 1846
<212> TYPE: DNA
<213> ORGANISM: Phytophthora infestans

<400> SEQUENCE: 17

```
gcaacgaaca agtctcttcg ttccacttcc gtttcacctc gtcgtcatgg ccatcgccaa     60
ttcgaacacg aagtctgagc tcgttctgga cggcgagtct ctctgtgctg aagacctggt    120
gcagctgtcc aagggagaca cgagaatctc gctaagtcaa gaagcctgga agcgcgtggc    180
ttgtggccgt gaggtcgtgg acaatatcct caaggacaag actcgtgtgg cgtacggtat    240
taacacgggc ttcggactct tctccaacgt cattatcggc cccgagaagc tcacagagtt    300
gcaggaaaac ctcatccgct cgcactcgtc tggcacaggc gagccgttga cattcgctca    360
gacgcgtatg ctgctcgcgc tgcgtatcaa tgtattggct aagggacact cggggatccg    420
tgtgcacact ctggagcagc taatagacgc ctttaacgcc gactgtctgt ccgtggtgcc    480
agccagaggc actgtgggcg cctcgggcga cttggctccg ctagcacacc ttgcactcgg    540
tatgatgggt gaaggaccca tgtgggataa ggtggatggt cagttcgtca tcagcgaggc    600
ctccaaggtc ctggccaagc acggactgaa gcctgttcag ctcggagcaa aggaaggtct    660
ggctatgatc aacggcacac aactcatcac gtcggtgggt gctgaggcgg ttgtccgtgc    720
tcagaacgtc gctaactgcg ctgatatcgc cgtcgcattg acactcgagg tgctctgcgg    780
tactgtcaac gccttccacc cgcgtattca tgcagcccgt ccgcacactg gccagatgct    840
cgttgcctcg cgtattcgca cactactacg tgctgacaac ccgtccgagc tgttccgtag    900
ccacaactac gaaggaaagg tgcaggacgc ctacactcta cgttgtgcgc ctcaggtgca    960
cggcattgtg cacgacacga tcaacttcgt acgtggtgtg ctggacgtcg agatgaacag   1020
tgccacagac aaccccatgg tcttcacggg tagtgccgag gtcacgacgg atctgtctcc   1080
ttcaattgac acgaatcaag tcaagcccaa catcgaacag gtagaacacg agatcacgga   1140
tctgaatgac gccaaggagg agatcaagcg tcttaaggct cttgttgcac agaagcagaa   1200
gcctgtggaa cacccggcgg cgggtatgaa gcgcacatcg gacacgttct accgtggcgg   1260
cggtggcttt gtcatctctg gcggcaactt ccacggcgag tatccggcta aggtgctgga   1320
ctacctggca attggtatcc acgagattgc tagcgttagt gagcgtcgta ttgagcgtct   1380
agtgaaccca acgctcagca acctgccggc tttcctcgtg ccagagggcg gtctgaactc   1440
gggttttatg attgctcact gtacggcagc cgctctggtt tcggagaaca aggtgctcac   1500
acacccgtcg tcggtggact cgatctctac gagtggagcc aaggaggacc acgtgtcgat   1560
```

-continued gggaggcttt gctgctcgta aggcgcttac ggttgtggag catgtcgaga ctgtagttgc 1620
tattgagatt ctggcagcgt gtcaagccct tgacttgctg cgtccgctgc gtacgacgga 1680
ggctcttgaa gctgtccacg gactggtacg cacccgcgtg gctaggtttg acaaggatcg 1740
cttcatgaag cccgacattg acgccgtgct ggacctcgtt cgtagtggag ctatctgcga 1800
cgttgtagct ccgttcttgt caaaactgca cgtgtcagga ctttaa 1846

<210> SEQ ID NO 18
<211> LENGTH: 1218
<212> TYPE: DNA
<213> ORGANISM: Phytophthora infestans

<400> SEQUENCE: 18
ccgcacagag caactgccac taggcatcat gctgcaccga cttggccgcc gctcgactgc 60
cacttccgcc cagcggtcac tgcgccgatc agccatgacg ccaccgcagc gccaatcctt 120
tcatttcagc tcgtcagcac gcaagccggc atctttggat gctcagaacc gcgtagctgg 180
tgctgcctcc tttttcctgg acgccaaggc cgtttgcaag ggcaagcgct gtgcattggg 240
caagaacaac agcggtattg gagctaaccc ggccacatgc ggggaggatt cgttcttcct 300
cacacctgac gtggtgggcg tggctgacgg cgtcggtggt tggaacgaga acggcgtgga 360
tccaggcaag atatcgcgct cgctaatgcg caacgcggca ttatttgtgc agcagcagac 420
ggccaatagc gagagtgcca ccacgcaaca ggttctggct cacggctaca agcaggcgct 480
gctggatgac gaggtggagg cgggtagcac gacagcctgt atcgtgagac tgaagcagtc 540
gtctgagggc aaacccgtgc ttgagtactc gaacctcgga gattctggct tcgtggtcat 600
ccgcaacggc gagataatct tccgcagtaa atttcaggtt cgaattgact gttgggagtg 660
acagtagaag agttactgac ggcgttgctt tagtattatg gacgtgctcc gtaccaactg 720
gcaaagatcc ctctgcggtt taagcagtat ggtgctattg agaatcaccc tgatgatgta 780
agtctgcttc gcatttggat actatttatg ctggagacag tacaatgcta acggttattg 840
ctccaggcgg actcgggtga gattgacgtg caagacggag acctcgttgt actagccact 900
gatggtgttt gggacaactt cgcccccgac ctccagaaag ctccttcgca gttcccggta 960
agattcttta ccgccgtgtt cgagctacct gtaattactg actttgtttc tcgttattgt 1020
ctgctatttc taccgtagcc gatgctctcc tggcgaagat attggtcagg tgaactcgca 1080
tcttttgtgg atgttattgc agagaacccc gacaaggctg ccgaaaatat cgtcctggcc 1140
tcgctccgcc acaaccttaa gcccgacgac atcactgtcg tcgtggcaaa ggtagtcgtg 1200
atggcatcaa agctgtag 1218

<210> SEQ ID NO 19
<211> LENGTH: 735
<212> TYPE: DNA
<213> ORGANISM: Phytophthora infestans

<400> SEQUENCE: 19
atgaagcagt tactgcagcc gatctcgttc tctggtgctg cgagtgtgtt cgtcgtggtg 60
gcaaagcaac gcaagaaacg ctgccgtgcc aatgacaagg aagatgacgc tgttaaggac 120
gacgaagaga ctgagacagc agaggacgaa ctggacgagg aagaccaacc cacgcgactg 180
tacgtggcca atgtgggcga ctgtcgagct gttttgtgca ctgcagacgc cttagcagtc 240
gacatgacga cggatcacaa ggcgtcgcta ccggctgaac aggagcgtat cgaggcgtca 300
ggtggcttcg tgcacaacgg ccgactggac ggcattctgc agatctcccg tggcttcggt 360
gacttggcgc acaaacagga tggccacttg gtggtcacgc cagatgtggt ggagcatctc 420
gtgaacccgt cggaccagtt cttgctgctt gcaagtgacg ggctcttcga cgtgttgacg 480
tcgcagcaag ctgtcaactt tgtgctgcgt aaacttcaga cccatggaga cgtccaactc 540
gcagctcagg agctggtgct caaggcgcaa gcttacttcg cacacgataa catcagtgtg 600
gtcattgtgg cgttgaacca gaaaggtgac gcgtgaaatg aacagcggct tctattgact 660
acggaagatc ggagaccgac gaagaagcag aaaacccgga gatcaagctc gagatccaag 720
aaattatgaa caaga 735

<210> SEQ ID NO 20
<211> LENGTH: 1845
<212> TYPE: DNA
<213> ORGANISM: Phytophthora infestans

<400> SEQUENCE: 20
atgcgacgca aggagaccaa ggtgttgttg acgctcgaag aggtgcgcga ggccttcgag 60
cagcagacgc cgctggccgt caaggacgcg ctgggtgtca ttcatgaggc gcagttcatc 120
atgaacctgg agccgaacct tgtggccgtg cggcaaagag cttcaacata tgtttttgga 180
gatatccatg gccagttcta cgacctgatg cagctgatgg acgccgttgg cgttgccgac 240
ttggccgagc gtgatgtcca gctggtgttt ctgggagact acgtggaccg cggggccttc 300
tcgtgcgaag tgatgctcta tctgctactg ctcaagatcc gattttccga caaagttgtt 360
ctcctccgtg gcaatcacga gtgcgaatcg atttcatcct tctacggatt tcgcaacgag 420
tgtaagggga agtacggcat ctcagcctac taccacttct tgtcctgttt ccaatcgatg 480
ccagtggctg cgctgctgtc cacgtcgcgt gggcaagttc tgtgtgtgca cggtggcctc 540
tcacccgagc tgaaaacaat cgaagacatt caaactatgg accgacggcg ggaaatccct 600
accacggggc tgttatgcga ccttttatgg tcggacccga agacttcgca cactcgcgat 660
gtggacgcag aggtggacac tcagccagga tgggagccca atcaggcccg tggatgctcc 720
tactacttca attcggcggc attgttcgag tttttaggca ccaacaagct gctgtcgatg 780
cttcgtgcac atgagttcga ggatgaaggc ttcacgtatc acttcaactc gcaggagtat 840
caagagctgg atactcgagt ggacaagtcc atgcctccac tcattaccgt tttttcggcg 900
ccgaactact gcgacagcta cggcaacacg gccgcctatt tgctcttccg gaatgaacct 960
ttctcgtggg aaatccagca aattaactcc gcgggacatc cagccccacc gattgcgagc 1020
gcagaacgag gatccgacat gtggcgacta ttcaatcaaa cgttgccatt cctcccagca 1080
agcaaggaat tctttgagga agttttgtgg ttagcagaag gacgacgacg tcttacaagt 1140
gaaatgcacc cacaagctat ccgaaagatg ttggatgacg aagtgaacaa atgggaattg 1200
gtagaagaaa cgccaacgcg cagctcgggg ccagcgtctc ctcctcgaat ccaccgcaga 1260
ccttctttga gtaatctgga cgagacccaa acggacgagc gtccaagtct gcttactccg 1320
caagagatgg acacaattaa gctgatgttt tcattaatgg acacggatgg cagcttggaa 1380
ctcagctcga ctaaagtgtc tcagttcatt ctcaatattc tgggtgaaaa aatcagcact 1440
gcggacgcgg aggcttattt ggatgctttg gactacgacc gcaacggagt ggtggatttc 1500
gcggatattc tgtcgtgggt tgccgtgatg aaggcgaatc gcaacaagca cgagtcgagc 1560
cgactcctga gttggccaac tgtacagagc ggtgtgcgca tgttgactcg tgggattttt 1620
tccagtaaag tcttgctatg gctcgcattc ggctgcttac tacgcgatat tatcgtccca 1680

-continued

```
aagcagcgaa aagtgatcaa gtcgtcgtcg atccgagtgc tgggctcagc gtcgctagtc   1740

ctgtacatgg tgggcgtatt gtcagggcga gagcgtggct ggctgcggct tttctctctg   1800

caacgcgctg tcggaattat gacgcagcga ttcgtatcaa agtag                    1845
```

<210> SEQ ID NO 21
<211> LENGTH: 1489
<212> TYPE: DNA
<213> ORGANISM: Phytophthora infestans

<400> SEQUENCE: 21

```
atgatgccgc ggggcttacc accacgaggc ccacctggca gtttcccacc tactagtgtt     60

gcggctgtac cccctgcagg cggtgccgct gcagctcgtt tcggcaagct ctctgtgaag    120

gtgttgcgtg cgtttgacct aaaaaagctg ggaatgctgg acactgcaga cccgtatgtg    180

aagctcacga tcggcacgca gaacgtacag actaaggtcc aagcaggcgg tggcaagacg    240

cctgagttta atgagacctt cgacttcaat attgcaaccg agaaggagct cgtggtcgaa    300

gtttgggacc aagaaaaagg aggacaagac cggttcatgg cgcaggcgaa ggtggagatc    360

gtgtcgtggc tatcaaaggg tggctttgaa ggtgacgtcg agctacggga tcgcgagaac    420

agccctgccg ggaagctggc gatcgttgcc aagttcacga agcccgaaat tggcgcgaca    480

ggacccgtca aggctccacc catggcccct ccgatactct caggtcctgc agtggctccg    540

ttgcccccag gagcgaatgc cgtatctgtt cctggtgcgc tgccattggc accgtccgaa    600

ccgcctcgag acccgaacgg caagttcacc gacaaggaga ttctcgaggc atttaaagcc    660

tttgatctgg atcacaataa ctatgtgggt gctgcggaaa tccgccatgt gctaataaat    720

attggcgagg cgcctacaga cgaagaagta gatgaaatga tcaagatggt tgacaaggat    780

ggcgatggcc aggtgagctt tgccgagttt tacgcgatgg ttacgaaagg gaagcagccc    840

ccacccggat tgggtgtcac tacagctctt ccggagaaag ctgcagctcc tggaggtgca    900

gtttcgggcg ctcaggccat tcagcttcgt aatcagcgca aaatggcgct ggaagagttt    960

gcacgcgata acggtatcaa acccgagagt gtgaagaagg cgtacaagcg attccaagcc   1020

acagataaag atggatcggg ccagatcgac tactcggagt tctgcgaggt gctgcaggtg   1080

gatccatcgc cgcagtgcga gaaggtgttc cagttgttcg acaatgacaa gacgggtcgg   1140

atcgacgtcc gggagttcat gattgcgttg tctaatttca cgggtgctga gaaggaggag   1200

aaactaaagt tcgcgttcct cgtgtttgat gaagatggta acggtgtgat cacgcgacaa   1260

gaactgatga agatcctgaa ggcgaaccac atggcctcta gcgaatcgga agttgcgcgc   1320

aaggcggaca ctattatgtc ccaaggggat aaggacggcg acggagttat ctcgttcgac   1380

gagttctcag ttgtgagcaa gaagtttcct aatattttgt tcccagccta cacgctaggt   1440

acggccaaag attagaatac ccgatgaata caatatcctt atctctcgt              1489
```

<210> SEQ ID NO 22
<211> LENGTH: 2862
<212> TYPE: DNA
<213> ORGANISM: Phytophthora infestans

<400> SEQUENCE: 22

```
atggctagca agctcaacgc gttcctggcc gcggtgcctg cgaacgccaa cgtgcccagc     60

ccgcccaaga cagcgccggc cgtgatggcg ttcccgcagc ttgagttcaa ggaagcgccc    120

gagaacgtgg gcgcattcgc ccccaccacg ccgcagccgc ccgtggtgcg tcgtcgccag    180

cgcaaaaata accccagcct caagctggag ctggactcga accaggaaca tgacagacct    240
```

-continued

```
gaggatgatc gagatatgtc gcgtccttcc cctctaaaga gcttcatggc cgcccaagca    300
gccgccgtta agctgaaggc acagacggag aagcacgata tcccaacacc agacttggcg    360
cgcacaagca gcgggtccga gctggacgcc aagtcggagg cgggacccat gcgcatggcc    420
agcgtacaag gctcgcacca ccgtcgcgtg tccaccgaca caacgctatt taaccggtat    480
ctgcgtcaac aagcagacct ggatattagt cacgacacgg tgcagtattt cgcaaatgtc    540
ccggtcatta ccgccactgc agctgccgtt gatgctctgg aatgcgaaat gagtgtggat    600
aataacgccg acgaggagca cgcgatcatc gtacaggaac ccgaggagat ccttgctgtc    660
ttccgactcg gaggcaccat ccctgtgtcc agtgcgctgg aaattgtacg acgagctacg    720
aacctcatgg cactagagca gaacgtcatc tcgattcgtg cgccgtacac tctagtgggg    780
gatctccacg gccagttcca ggacttgctc gaactcttcc gagtacacgg ctctcctgcc    840
gtggacaacc cgttcttgtt cctaggtgac tatgtggacc gtggcgtgtc ttcgtgcgag    900
ataatcttat tgctcttggc cttcaaagtg gctttcccgg acagtgtcca tttattgcga    960
ggcaatcacg agtgtcggag tttgagtaca ttttacggtt tccgtgccga atgcctcaag   1020
aagtacggac ctgtgctcta taaccgtatg atcaagtgtt tcgagagtat gccactggct   1080
gcacgactcg agacagcgca cggcacgttc ctggctgtac atggcggact gtcgcccgat   1140
attcagttcg tgggggacat taacggacaa gtgaaccgct ttatggagcc tgaaccaaac   1200
ggagctctgt gcgacttgtt gtggtcagat cctgcgaagg gcgaagctca ggagcaggag   1260
tgggcaccca atgggatgcg tggctgctcg ttcacattta atgaacgcgc ctgtcgcgaa   1320
tttctgaagc gcaacaacct cctggccatt gtacgtgctc atgaactgga agaaaatggt   1380
tataaggagc actttcgaca cgaaggagac cgcacagaag aagacgagga cgggaaactg   1440
gctctacctg cggttgtgac ggtgttttca gctccggagt actgcaacac gaaccacaat   1500
gtcggcgcga cgctgaaaat tccctgggaa agacaaaatg gtcgtctgct gcagtatcag   1560
cagcataaac gcagtcaatg ttccgagttt gagttcacgc gagccagcga ggagacggcg   1620
gccaaggcgt ttctggagga gaatttgccg ttcttgccga ttgactttta cgacttggtg   1680
aatgtgtgtc ggcagctgcg gctcactctt gagagagcag cgagtatcac cccagcacct   1740
gcttcagaac ctattcgcaa gctgtcgctt gtgtcgtcgc tgtgtgcgcc agcaactagt   1800
ctggaaacga ggatcgagga ggaagaccca gagcttcccg tgtcgccacc tgcttctgca   1860
ccagcaaatg aagtggagaa ggaagctaca gcaactctga aggcagtggg cgagtcgttg   1920
caggattggg aacttgttga gacgaagagt gtcgaggttg acactaggaa ggtgaagaaa   1980
gacaagaaga aggagaaaaa ggagaaaaaa ctgaaggaga agatcgaaaa gaagaagcaa   2040
aaggacaaga agaagtggga tacgagtcga attgctagcg gttggaagct ctgccctggg   2100
tttgtacgct tctacgaccg ctacttctca agagacagta tgaagaagag cgagccggag   2160
atcacctcag ctcctggcca tctaggcaag cggccgtcgt ggatctcaaa ctacaaaaca   2220
ccttttagac gctcgacttc gaccggcgag gcccccaccg acactgaaac tgtcgacacc   2280
gtcttggact ctaccggtcc tgctcgacgg aagagtatga cggattggat gcccatgccg   2340
tcgttcgagc aggtggcgca gctgacgaac acgcttcagg gtcacattcc cgtgcagtcg   2400
aacggcgtca atgtattcac gaaggcacag tggcaagctc tgaagttgta cttctcgatc   2460
ctggatctgg atggcaatgg cgttttgatg gaagagagct tcgttgttct cctcgcagag   2520
caagacagcg gtgggttgag ttaaagtgaa gtgaggatgt gaatttgttg ctaatttaaa   2580
```

-continued

```
ttgttgttgg tgttgtgtgc agatgcatac gcgactgaag acgaactgag tctgttgatg   2640

gaagtcatgg actgcaacgc cgacaatatg atcactgagc aagatttctt gctattcgca   2700

taccgagcct tactgcgatg gaaaaaagct ctacatggct ccgactagag tgtgcaggag   2760

cggaatcgaa ctgacgtagc gaagtatgaa caatgccaga ttagaatcca cagtagcgcg   2820

gcatatgccc ataatgaaga acgagaaatc tattagttga aa                      2862
```

<210> SEQ ID NO 23
<211> LENGTH: 984
<212> TYPE: DNA
<213> ORGANISM: Phytophthora infestans

<400> SEQUENCE: 23

```
atgtccgcgc cgaccttcca tcgatcattc cgcaatttgc agcttccaag tcaacagtcc     60

aagctccaaa ccgaaacaag agtgatgatc gcaatttcga cagctgagga tttccactct    120

gccgtggccg ctgcgactca gaagccgttg gttgcctgtt tctccgcgcc gtggtgcggc    180

ggttgcaagt tggtggcgcc caaggtggac aagctagccg aggagcttgc cgagaccgtc    240

tcgtttgcca gggtgagtgc tgaggagcac gagacgttat gcgaagaagt ggaagtggac    300

agcttcccgc acttccgcgt gtacagggac ggcaagattg tgggtgacta cacgagctcc    360

aagttcgaca aggtggagtc ctttatccgc ggccatgtgg ctcctaatac tgtgcaggag    420

accgaggaaa cacctgaagg cgaggttacg gaggaaacgg cggagaagga tgctgcgaaa    480

gaggaggaag tgtcagctga ggctgcgacg gaaggctcaa agaagcgcca ggagcgtgaa    540

gaggaggaga cgaatgacga gcaggtggct aagaaggcca agacggagga ggaggcgtcg    600

acggaggctg agaaggctgc aactacggag ccagctgaga aggttgagga agcggcaacg    660

gaggagaccg agacggctga aaaggattca tcagaagaga agatcgaagc tgctcccgtt    720

gagaagtctg aaacggccgg gaaagacact gctccagtcg atgctgctgc tgcttaaacg    780

acactgctct gctttgcatg atgtctaaat cgacggacat cttctgtggg ctagctgggg    840

gctgattgat ccagctgaaa tcaagatgaa acaataaaaa aagaagtatt ttatggcgat    900

tcttttgttt gtgcccgata tcctcgacat gttctgaata catgtacatg tgctctgcct    960

tcttgtcaga acaatgtgga atgc                                           984
```

<210> SEQ ID NO 24
<211> LENGTH: 501
<212> TYPE: DNA
<213> ORGANISM: Phytophthora infestans

<400> SEQUENCE: 24

```
caagcagtga agctaaggaa caacaagatc aaacaaacca tacacctatc tacgatgcct     60

gtcgagatca acacccccga agagttcaac gccgctatcg gcgagaagaa gctgacggtc    120

gtgcagttct ctgcgccgtg gtgcggcggc tgcaagatgg tggcccccaa ggtgaccaaa    180

ctgatggagt cggacttcgc tgacgtcaag ttcctcaagg tgagcgcgga ggagctagag    240

gatttctgcg aggagatcga cgtcgacagc ttcccaacgt tccgcgtgta caaggacggc    300

gaagtggcgg cgtcttacgt gagctccaag tttgagaagg tagagcagtt catccgtgag    360

aatgcgaagt aagcgtgacg gcgatttgcg accgtctatc aaagctcgcg catggtgatc    420

tacaggcttg atgacctacg ctaagatggt ggagagcgag tgagtttggt ccccggcatt    480

gcgtatcggc agtggactga a                                              501
```

-continued

<210> SEQ ID NO 25
<211> LENGTH: 734
<212> TYPE: DNA
<213> ORGANISM: Phytophthora infestans

<400> SEQUENCE: 25
gacaagcagt gaagctaagg aacaacaaga tcaaacaaac catacaccca tctaagatgc 60
ctgtcgagat caacaccccc gaagagttca acgccgctat cggcgagaag aagctgacgg 120
tcgtgcagtt ctctgcgccg tggtgcggcg gctgcaagat ggtggccccc aaggtgacca 180
aactgatgga gtcggacttc gctgacgtca agttcctcaa ggtgagcgcg gaggagctag 240
aggatttctg cgaggagatc gacgtcgaca gcttcccaac gttccgcgtg tacaaggacg 300
gcgaagtggc ggcgtcttac gtgagctcca agtttgagaa ggtagagcag ttcatccgtg 360
agaatgcgaa gtaagcgtga cggcgatttg cgaccgtcta tcaaagctcg cgcatggtga 420
tctacaagct tgatgaccta cgctaagatg gtggagagcg agtgagtttg gtccccggca 480
ttgcgtatcg gcagtggact gaaggatgct actaatatat tgaaatagga aaccatttta 540
acgaagaccc tgagcctcag gctcattctc aaccggaaat atagaccgca tgcggtccca 600
ggaggacaaa tagagtcttc taattggctt acggggtagg tggtcgcatg cgacgaagtt 660
cataaaaaga cgctcatgcg gcaatttgcc cgcatgcgct aaacttgccg cacagtagag 720
tgtaggggtc gagt 734

<210> SEQ ID NO 26
<211> LENGTH: 1448
<212> TYPE: DNA
<213> ORGANISM: Phytophthora infestans

<400> SEQUENCE: 26
ctcgagccca agcgacaatg gcggcggtga ctggcagtgt ggtaagcgtt cagagtgtgg 60
cgcagttcga cgaggcaacg gcgcgcgagt cgacgctatc cgtgagtttc ttctgggccg 120
aatttcacga ggcctgccgt cccaatggac agctggacgt ggtggtgcgc cagctcgcga 180
ctctgcaccc tcgcatccgc ttcctcaagg tggcggccga ggagattccg gagctctcgg 240
agcgttttca gatcgccgta gtgcccactt tcgtcgtcgc acagggtcgc gccgtgctgg 300
acaaactcga gggcgccaat gtggccgaac tggccaagcg cgtggatgtt ctgagcaaga 360
gcgtggccaa gagcagctcc acatccgcgt ccacagccga ggacgccccg aaaccgctgg 420
atgacgcgct cgaataccgt ctcaagaagc tcatcagcgc gtcacccgtc atgctcttca 480
tgaagggcaa tccgacggag cccaagtgcg gctttagtcg acagatggtg gcgctgttga 540
acgaagaaaa gatccaattc ggcacctttg acatcctcaa tgacgacgaa gtgcgtcaag 600
gactcaagca gttttccaac tggcccactt accctcagct ctatgtgaat ggctcgctca 660
ttggcggact ggacatcgtc aaggagatga agtccgaggg atccatcgtc gagcaactag 720
gactcacgaa gaacgtcgag gaggctgaag ctgccttcca agagagtctc cgtgcactcg 780
tcaactccgc tccagtgctg ctcttcatga aaggccatcc gtccgagccc aaatgcggct 840
ttagcaagaa gacagtcaag ctcctacgtg accaccagat tggcttcagt tcgttcgaca 900
tcttgagtga cgagcaggtg cgtcaaggtc ttaagaagtt ctccaactgg cctacgtacc 960
cgcagctgta cgtcaagggc aaactcgttg gtgggctgga tatcctgaac gagatggcgg 1020
aggacggcga cctcagtgaa cagcttggcg tggagaagaa ggccaagaag gagaacaaat 1080
acgaacagct aatcaaccgc gctcgcgtca tgatcttcat caagggaacg ccccagcagc 1140
cgcagtgtgg cttcagtcgc aagctcgtgg acatcctgga cgccgagggc ttcaagtacg 1200
actactttga catcctcacg gacgacagcg tgcgtcaggg actgaaggag cactcgaact 1260
ggcccacgtt cccgcagctt tacgtcaatg gcgagttgat cggcggactg gacatcgtgc 1320
agcagctgca ggaggacgga gaactcgccg agctcaagga gtagacgacc aggtcatcct 1380
tcgcgtaaaa cgaatacaga aaatcatttc tcttatcctg catgtgtatg ctgggtttga 1440
tggtttaa 1448

<210> SEQ ID NO 27
<211> LENGTH: 1106
<212> TYPE: DNA
<213> ORGANISM: Phytophthora infestans

<400> SEQUENCE: 27
gtcggaagag gtcgtcggtc gtccatgcag ctgcagacgt tggcgtacgc catctccggc 60
gccttcacgc tgctttccat tatcctttcg ggatggctca tctggacaca cttgctgtac 120
aatccgtcag ccggcatccg caagcacgtg atccgcatcc tcatgatggt ccccatttac 180
gcgctaacgt cctacatggc gctggtattc aacgagtcca aactgttgtt cgagactgtg 240
cgcgatctgt acgaagcctt cgcgctctat tcgtttcact gcttcctggt cgagtatctg 300
ggtggccaat ccgttctagc aagcaccatg cgctccaagc cgcagatgac acacgtcttc 360
cctttctgct gtgtacagcc gtggtccatg ggcggcaagt tcctgcgtca aaccaccatc 420
ggcatcttgc agtacattcc cattaagctg cttatgagca tcgtcatgct catcacgagc 480
ttggcaggtg tatacggaga aggagagctc atgaaccccc tagtgagcta cggctacgtg 540
tgctttatcc tcagtgcgtc gcagacgtgg gcactttact gtctgctgat attcttccac 600
ggagctcacg aggagttgca gcccatgcgg ccatggccca agttcctggc cattaaggca 660
attattttct ttacgtactg gcagtcgatc atgattagtg gacttgtaag tgtcggggtc 720
atctcggaga agtggcatat cggctgtccg gactgctggg acgctcagaa aatcgcctcc 780
gcactgaatg actttgtcat ctgcgtcgag atgctgggct ttgccattgc ccaccactac 840
gccttcgcga ttgaagactt tttgtcgccg tcaggtacgg caggtgttag tgtgccgtct 900
tcgaacgtca aggcaccact gctggccaat tttatggacg ctatcaacgt gacggacgtg 960
tcgacagacc tcaagaactc ccggaacgag attctcacca agaaacaggc gctggctgcc 1020
aagttcgagc gcatgaactc gacttcacct ggtggtggca tgttttaata gcgtcagtta 1080
aaagggagcg atacagtaag cacacg 1106

<210> SEQ ID NO 28
<211> LENGTH: 2007
<212> TYPE: DNA
<213> ORGANISM: Phytophthora infestans

<400> SEQUENCE: 28
atgagctcac aggacggcgc tggtcgcgca tctgaggaca agaatggaga cggcgtgtac 60
gtgacgaaga accgctcgct cttctccatg tggctgcacg gcaaggcgat tccaagccgt 120
tctggtccgg ccgtggtgtt ccgctcggcc gacgtgatac aggaagggta tttgctcaag 180
cagggcctgc gacttaaaat gtggtcccgc cgctacttta tactgcgact cgaggagcga 240
cacatgactc tagggtatta taccagcaag gactctctga ctttatgctc cgagacgccc 300
atcggaccag gacacttgtt gggacacgtc aacacgacca aatacccgcg tcgtctcgag 360
ttgcgctgcg gtacaaaggt catggtactc gaggcggagg accaaaagtc gtatgaagcc 420

-continued

```
tggaagaacg ccctccaaga agcgatacgc tggaaccacg ccatggtgcc ttcaaaagac    480
ggcagttttg tcacgtacgg gaagcaagcg accgaggata taaaacaaga ggaacgcagt    540
cgcgccgagg cggccaagaa gctgcgagag aagcagcgag cggacgaggc cgccgccgcc    600
gccaacgccg ccaataaacc caaatatctg cccgcgacac gccccgggac gcaatgcttt    660
atgacatcga atacaagatt tgagattccc tctcatttcg aatatgtcaa aaccatcggc    720
tcgggcgcct acggagtcgt catctccgct acgagctcgc aaacaggcac cacggtggca    780
attaagaaca tccagcgcgc gttcgacgac ctgacggacg ccaagcgcat tgtacgcgag    840
attaagctca tgcgccactt gaaccacaag tgcgtgcttg ggtggagga catttttcgag    900
cccgtggcgc tgtccaagtt cgaagacgtg tacattgtgt cccaattgat ggctacagat    960
ctccaccgcg tcatctactc gagacacgcg ctgtcggacg aacacatcgc cttcttcatg   1020
taccagatgc tgtgtgccat gaagtacgtg cactcggcca acgtgatcca ccgagacctg   1080
aagccgtcca acgtcctggt gaacgccaac tgcgagctca agatctgcga cttcggactg   1140
gcgagaggcg ttttccccga agaagagctg gaattgacag aatacgtagt cacaagatgg   1200
taccgagcgc cggagatcat gctggggtgt atgaagtaca ctcgggaggt ggacgtctgg   1260
tccatgggct gtatcttcgc cgagatgatg tcgcgcaagc ctcttttccc gggacaggac   1320
tacattgatc agctgcatct catcatgaac gcgctggggg ctccaaacga ccaggatctc   1380
tactttttga gcaacgcgcg tgctaggaag ttcatgaacg ccgagttcca gaagcgcgga   1440
cccaacccga cgaagcctct ggcgcacatg ttcgcagatt cgcctccaga cgctctggat   1500
ttactgcaga agatgctggt gattgacccg aataagcgga ttagtgtgga cgaggcgctg   1560
gcccatccgt acttggctgc gatccggaat gtggaggacg agacgaccgc cacttcgagc   1620
ttcgattttg actttgagaa cgagaaattg acgaaacccg tgctgcagag actgatctgg   1680
gacgagatga ggcatttcca ccctgaagtg ggcgacgaga cagcgacgga gggagatgac   1740
agcagtgtcg ctaccacgca ggcttctatc acacccgtga cacctgtgac cccccgctacg   1800
gtagagcaag acacaacaga gacgacaagt gacagctcgg acgcccctgt caaggtatcg   1860
acgccaacag cgtcagagga agccaagcca gaagacgaag acggggaaca acacagcacc   1920
aatagcgaca agatccatag gacagacaaa ctgacagacg cacagacgcg acaagaggcc   1980
ggcgaaccag ctcgggaagt cgcataa                                       2007
```

<210> SEQ ID NO 29
<211> LENGTH: 2053
<212> TYPE: DNA
<213> ORGANISM: Phytophthora infestans

<400> SEQUENCE: 29

```
gctcaagcca gagtccaaac gctcgttcaa cgcccattca acgctcgagc aacggctgat     60
accgacatga accgtaagct ggagctcatg gagctggaca gcggcggcgc cagccctaac    120
agcagcaaca gtggaagccc cagtccgact ctcgacctgc tgcatcgctc tgattcgagt    180
agcagtaacc aggggggtga gatgcctctt gtcggggttg cccacaaccc agacgtacgt    240
cgtctgcctt tctctatttg tagtgatagt attttcacgt agacgtttgt tacagctgag    300
ttatttgagg gcaactgcaa cacatggagg cagcagcacg accagcagca agtatggcag    360
ccccgaggag tcatttggtg aagaggacga ggacaacaac aagaagacgg cgcgtcgcaa    420
gaccgactcc aacagcaagc gtccgtggac acgcgaggag aatgacaagc tcatgcaact    480
```

-continued

```
cgtcaagcag tacggcgcca agcgctggtc tctcatcgcc atgcacctgc caggccgtgt    540
cggtaagcaa tgccgtgaga gatggcacaa ccacttgaat ccgtcggtcc gcaaggacgc    600
atggacggct gaagaggact atgtcatctt cgagtgccac aagaatgtgg gcaaccaatg    660
ggccgagatt tccaagatgt tgcctggcag gacggacaat gccatcaaaa accgctacta    720
ctcgaccatg cgtcgcatgc agaggcagtc aatccgcaaa aaaggtccca tgcgtgatgg    780
caagagcatc cgcgtggcgt cagtcacgtc gtctcccgtg caaaacaaca accaaatggg    840
tcctgctccc agccagcgat ctttgactgg catgcaacac cagttgccac cgcaacaaca    900
gcttccgcac cgaggggtga gtttccaatc cacatatcaa cggctcttct cggaggcctc    960
tggggacgcc gcacgcgtga gtcccgctgc ttcgaattaa ttggagagga tcgatactaa   1020
ctattatggt gttgatatat aatgcaggat ggcaactcga tagtggactt tgaacgttca   1080
aacatgatgt ccgcatcact acgacaaccc acgatggtct acccgctaaa cggaggtagc   1140
ttttcaaacg ggatgaaccc ggactatagt cgtcccatgt ccatgacgtc gtctccctgc   1200
tcggtgtccc ccgccgatga tctgaatcat aacagccaga acgagacctt tgactacgtt   1260
ccgatgcaat cttcgatcca gcgtgtacgg tcatctagtc cggttgtgat gggcactcct   1320
ccttcgacgt caataggcat gatgaactca ccttacggct cgcctgcaag tcacatccaa   1380
cagcaacagc ctggcaacta catgatggca ggaaacccat attctaacaa caacgtgcgt   1440
gggatgtact ttgggacgtc tgggcttgct cagcaatacc gtcctgatgc ccctgtaaac   1500
gtcccacaca agcgcctcct cgacgtccag ggttcacaac gtgatatgtg gaagaatgat   1560
agccctgtat cggtagcagc accgatattc cgcggtatgc cggcgacgca catgcagcaa   1620
ggtcaagtca gcgaaccgat ggcattgcag cagtccaagc cagcttccat gccactgtat   1680
aggcaagcgc cgaatatggg tcacttcaac agcatggagc aggtatggac ggatgatgca   1740
tatctgtgat tggaccgcca ttgtggcatg ctcctgatag actgcatgaa acaaatttaa   1800
agttattact taccaaagac agtggcttct cttactcttt acttggttaa ctttttttcgc   1860
ttgatctaca gcggtttcac gttaggtagc tgtagctcct gatcgagttg cttattaaat   1920
agcaccactt gttgacaggg attgatatta aaatgaattt ttttcagact aatatattag   1980
ctgatattac atgtaccaaa atgtcaaact aatagctgac tattagtttg aaaaaggcgc   2040
caaaacaagc taa                                                      2053
```

<210> SEQ ID NO 30
<211> LENGTH: 1173
<212> TYPE: DNA
<213> ORGANISM: Phytophthora infestans

<400> SEQUENCE: 30

```
atgcttggcg acgtagacag tttcggcggt ctgggtccca ttccgtccat gaacgcggtg     60
ttggagaagc gcacgtcaag tcagttttcc attagctcgc tgctgccccc gtccgtgagt    120
gtctcgagta ctggtgtgtt aaacacaact gttacacgga gcgagagcgc agtgacagat    180
agtgttgaag caactaccga taatgaaggc caaggatctg caccaagggt gtctaccaca    240
actgcagagg ggtctggtgg caacaccaag tacatggacc ccactacggg cgactacatg    300
tacccggaca acgtcaagcc catgagcttc tacgacaaac aacgtcttgt gcagaagatt    360
acgatgcttc ccagtcaata tctgcgtggc ctcatggacg tcatcagcaa gtaccagcca    420
gatactgtac gtcagatcga cgacgatggc tacgcgttcg atctgggtca gatgaacgag    480
aatactgtgt gggctatcag tgactacgta aaggactcga tgattgagct ggatggatac    540
```

-continued

```
attaaatcac tcaaccaaac tgctattgac cttgctgccg gtgaggatcg acatggagaa    600

actgttctga cggccgcaag tgcggctaca cccaccagca gtgcggttcg ccacttgacc    660

gacactctgg cgatgaacac gtccaagatg tctgtcatca ctaataacga gaatcagaat    720

aaattcctgg aacaggtgga gatgtattcc aaacccaaag tgaccaagtc gcgtgtaaag    780

cccagcaaga agcaccagtg tccgacgtgt aacaagcaat tccgcggacg ctccgagctg    840

cagaaccata tcagaactca cacaggcgag aagccactca aatgctcgta cgcgggatgc    900

acgaagcgat atgcacacag ctcgaatctg cgtgcacacg agcgaacaca cgccggaata    960

aagccgtata catgtcacta cgacggctgc gggaagagct tcgcccactc tgtatcactt   1020

aaggaacata tttggatgca tgcaggattc cagccctacg tgtgtccgta cgagggatgc   1080

cagaagaagt ttacgcaggt ctcaaatttt gcccgacaca agaagacgca cgagaaggaa   1140

gacaacgaac actcgattga gagcgataat tag                                 1173
```

<210> SEQ ID NO 31
<211> LENGTH: 754
<212> TYPE: DNA
<213> ORGANISM: Phytophthora infestans

<400> SEQUENCE: 31

```
atgattaagc tcgcggccgg tgtgtccaag aaatccgtcg tcgatgtgta tgtcactctc     60

agtgtgcccg acagccccgt acttagcacg gcacagaaga acgtggagct gaacgtcgag    120

aagttcttcg tggtcagcaa gactctgcct gaattgcctt ccaggtagaa gacgctgccc    180

gccccgacgc cttcgtcaag gcaacggatc ctcctacgtg aacgtcggtc tggaggatcg    240

tctcaactcc cgtccgcttg acctgcatac acctgccaac cagtgtatca agcgcatcca    300

ggccgctgtg ggccagctgt tccgtgcatt cctcatccag cgcgacttcg tggagaccca    360

cacacccaag ctggtcgctg gcgcctcggg gagcggagcc aactgcttca cactcaagta    420

cttcgattag gacgtcatct tggctcagag tccgcagaag tacaagcaga tggcgtgtgc    480

tgctgctggt ctcgagcgcg tgttcgagat cggcccggtc ttctgtgctg agaactcgag    540

cacgcaccgt cacatgtgcg agttcgtggg tctggatctg gagatgacta ttaaggagca    600

ctaccacgag gtcctggagg tgttctcgga cctgtacatc tacattttcg atggcttgaa    660

ggaacgttac gccaacgaat tggctactat caacaatcag tacccgttcg agccgctcaa    720

gtacattaag ccgtcgctta tcatcaactt ctag                                754
```

<210> SEQ ID NO 32
<211> LENGTH: 659
<212> TYPE: DNA
<213> ORGANISM: Phytophthora infestans

<400> SEQUENCE: 32

```
gggctccatg tcatctgcga ctttggacgg agctctctat tgtagaattc aactgactct     60

agacaagtaa ccatgcagaa cgaggccggc cagtcgatcg acatctacat cccgcgcaag    120

tggtgcgtat tgcgctggtg actttaatac gctcagagct actggagcta actggtgctt    180

gctattgtct gtcatcgtta tatagctcgt ggaccaaccg catcctggcg gccaaggacc    240

acgcctcggt gcagatcaac gtcggccgcg tgaacgccaa cggcgtcttc acgggtgagt    300

cggacacctt cgctcttgct ggctacattc gccaccacgg tgagggcgac atggccatca    360

ccgagctggc tcgccaggcg gacgccaaga actaagcaga ccaagttgtc gtgatcgcgc    420
```

gctgctgctg cgaagtggag tgtgcgttca tctacgtcta gctggcagtt caggaggctg 480
gtgattacga tatgtatcaa cagatacgtc tgtgatcgct ggcaggaatt gcggtaccgt 540
cgcttatgga gtcggttgtt tgcgggttcg acctcgcctt ttgatttgat cgggtgtagg 600
cttagtattt aactctggcc aacggacgag caagaataaa gtagttcaaa cccgtcaga 659

<210> SEQ ID NO 33
<211> LENGTH: 1049
<212> TYPE: DNA
<213> ORGANISM: Phytophthora infestans

<400> SEQUENCE: 33
ctcgagcgca agacgatctc cgctatcgcc ccaccatgtt cgccagcttc gccactgccc 60
tcatcgcttc cactctccgg ccctcgagcg cagccgccac caactatgcc ggtggctggc 120
ttccgtcgga ccccaccaac cagtgtgtgg atatttgctc cgctccgtcc aagacgtgcc 180
tcacttcgga cgctgcctgc ctcgccaagt cgatggtccc gggcgacttc gactatatgg 240
tcctggagca gctcttcgtg ccgcagttct gccgtgacct gctaaagggt gtcgactcca 300
ctatttcgca ccaaaacatc gatatgtacc cgaacggcac agcctgcgtg gagagtgtgg 360
tcaagagtga gctcacgatt cacggtctgt ggcccaatta caacgatggc tacgtgagct 420
gctgcaatcc gagctcagcg gtggccaacg acccttataa cgccgctgac ttcgctgccg 480
cccaaagcag cctactcacc accatgggtg agaagtgggt ggacgctacg caagccacta 540
cgtacgaatc gctatgcgag atctacaacc acgagttcca gaagcacggt ctctgctatg 600
ccgctgacga cgctgattac atctcggctg ctgtcacgta cttcactgct acgctgagca 660
cggcggaccg catcagttca gccaccgagc agatcaacaa gtgggcagct cagtcgacgc 720
ctcagacgac tctggccgag attgaggctc tctacggcca cagtgtcatg gtgttgtgct 780
cggctgtgga tggcaacaac caactgtcgg ctatccgtac gtgctacgag aagccgacaa 840
acatcacgag cgagggagcg tccgcgcaga ttgactgcgc agccgcgacg gccacctcct 900
cgttctccgt atgctccggt gactcgccga tcactctgac tgcatacaca gcccccacct 960
cggcttcgat gcaataagct ccgacgatag agcgacggtg cagtctgcta gtataaagtt 1020
caatgcacca gttacttaaa aatgtacca 1049

<210> SEQ ID NO 34
<211> LENGTH: 1203
<212> TYPE: DNA
<213> ORGANISM: Phytophthora infestans

<400> SEQUENCE: 34
atgaccaagt ggggggttgt agtggcacta acactgctgt tagcgacgcc tagtttagtg 60
ctaggcgcct gccccaacaa gtgttccgga cacggcaaat gcggtctcaa tgacgtctgc 120
caatgcatgc agaactgggt cggcggtgat tgctcgggtc ggcaatgtgc gttcactcgc 180
gcgtggcaag atacagcaca gcgcgacgac gacgcacact accacgcaga atgtggcagc 240
cgcggaacgt gtgatcgagc tactggagaa tgcacatgtg acgcaggatt catcggcagc 300
ggctgtcgac gaatgcagtg tcccaatgac tgcagtggcc acggcacgtg tgagtttatt 360
gaggaattgg cgacggatac ggcccacaag cggattgggg gagtggcagg tcgtaaatac 420
acgctttggg accaagagaa gatcatgggc tgcgtatgtg acgccaacta cgaaggtcac 480
gattgctcga tgcgctcgtg tcctagaggc gacgatcctc tgaccccgaa tcaatacgac 540
atggtgcaag ctattattct tgataaggct ggcggtgagg ggtacttgac gtactatgat 600

```
ccgtacggca atgcgtatac tacggagaaa atcacgcttg gtggaacgct gagtgtcgct    660

tttcaaccaa cagacgatga taccacatgt gcaaacattc agaaggcgct ccgccgttta    720

ccgaacaacg tgctcaacac agtcactgtg gtagctgttg acaggtttta tgccttcaag    780

cgctctgacc caacggactc gttggggtat ggaacgttaa acaaaattgt aaatgacgac    840

gctgcagcgt acgcaggaac cggaactcaa attaaagcga tgtgcgaggt gatttttacg    900

tcggagccgg gcactacggg gtatcagaat ttgctggatt gcaatgttgc cgcgcatggc    960

gatactaagg gccagcaccc gcttactact ggtgtaacgt ctggcacttg cgtcgttaaa   1020

gaagtctatc cggtgacgct tggcacgagc aacatgcttg ccgaagatac tccagcgtat   1080

cgtccattga ccgagctcac cgagtgtgct ggtcgcggca cctgcgacta cgacacagga   1140

acatgcgagt gcttcgcggg ccacatgggc ttggcatgcc agaagcagga agcgctcgtc   1200

tag                                                                 1203
```

<210> SEQ ID NO 35
<211> LENGTH: 7947
<212> TYPE: DNA
<213> ORGANISM: Phytophthora infestans

<400> SEQUENCE: 35

```
atggcgcgcg ctccggcaca attggcgcag cttttactag cggcgctgct gctgtcagcg     60

atgtgtgagg cgttattgcc tatcacgaac gcgctgcagc gtgcccgcca aaacctcacg    120

gccttgcagc ggcaatggat cgatccggac acggacccca agttctacaa catatcagtc    180

cccaagggtg ccttcaactt cggtggcaac tcgagctaca acaacgagta caagctcatc    240

ttctcggacg agtttaatag ctccaagcgc acgttcgagt cgggtttcga ctccaaatgg    300

acggcagtca acctccgcga taccaccaac atggggcagc actacttttt gccccaggct    360

gtgcagatcg acaagggcaa cctcatcatc acgacctcca agcccaaaca gcgctaccgt    420

ggcactaagt acgtcagcgg tgctgtgcag acatggaaca agttctgtta caccggcggc    480

tacgtcgagg taagggccat tctgcccggc aagtggggta tccccggcac gtggcctgct    540

atctggatca tgggcaatat cggccgtgcg ccattcctcg gatcccagga cggtacgtgg    600

ccgtggagct tcgactattg cgccccctac gtggagaagg ccgagaaggt caagcagaag    660

atcaatgcct gtggcaatct gaccaacaaa cacgacaagg aatcgtatcc agagatgtac    720

ggcttgaacc cctttcaggg tcgtggagcc acggaaatcg atgtgattga agcgcagatt    780

cgtgctcgtg atgagcctgc attcatctcc acgtccctgc agatccgtcc cagtctgtac    840

gatgatatgc gcccggcttc agagtcgctc cctgctcctg gacaatggta ccagggtctc    900

aagtttggtg agttcacgaa aatcaatagc gactactacg gtgagatggg cctcgactcc    960

atttcggctc tgacacagct cgagtccaat gcgttcaagt cgttccactt gttccgcctg   1020

gactggtctc ctggtcccga aggttacatt cgatggtgga tggacaacag cttcgtgttc   1080

gaaatccctg gatccgcgct gaataagtgg gtaggtgctg tccccccctcg ccagatcccc   1140

gtggagccta gttatctcat tctgagtacg gctgtttcgg agaagttctc tccaccgtgc   1200

gatgggcaga tttgtaactc gctatggccc tccaacttta cgatcgacta cgtacgcgtc   1260

tatcaaggca acccgaaccg gtatacttcg gtgggatgca atccggaagc ctacccgacg   1320

aaagattgga tctacgccca cccagtggaa tacggtctcc cgtggtatgt ttcactacgt   1380

gtggacatcg gtctgctgca tcttttcgct gtggttaatg cgctgctggg tctcttcatg   1440
```

-continued

```
gcgttccgtg gcacgtccca accgaagatg ttgtcagcgt acgccagctc gttgtggctg   1500
actgcagcct tttatggagc tcttagttca agcgcccccg tagaccttgc ttggattcag   1560
actgcgcttg cgtgtctgtg cgggctggta cttggcggtc tttgttgctt ggtgtacccg   1620
gtttcgcttg gtgcaatgct tggactgtat ggcggggtga tagctagcca attcgtgcct   1680
ttgctgtcta cgcgcgtgat cactgcatta ctggttggtg tgggaatcgc gctaggatct   1740
gctccacaga tcgacacgaa gcacgttgtg attctgtcga cctctttgct tggtagtttg   1800
gcgtttctgc tctctgtatc gctgtgggtg agtgaaggcg atattgctga gaatgcgtgg   1860
aatctcgctg gcttcatttt caatggtaac aacgatgacc acgtgggttt ctgcacgaaa   1920
tattgcctgg cgatgtatat tctgcttgtc gtactcagtg cggtgagcac tacgtatgga   1980
tacctccgta tgcgtggcgt gacgctgcgc accaacccgc gtgaggccaa gttccccgcg   2040
gtgtcagcaa gttctgacgc gcgggcttgg agacctgatg atgatgcggg cgtggagaag   2100
actacggtga attttttctc gccatccaag ctgccgtaca acatgcagca gttcagtacc   2160
atcttccgta tcgctgtgaa cgtgcagcgc tcgtttggct tccaacttga caacttccgc   2220
aaccagacgg aacacgttgt ggtgcttctc accaacaact cgcgaaagag cggaaatcct   2280
taccgcaagc tgcacgattt ggtgttttcc aactacaaca actggtgctg caagcttaag   2340
atccagcctc tgaactgggg cgagcagcga ccaccgcagg gtggtctcac aatggtggac   2400
gagatgtcgg tggacttgtg tctgttcttc tttatctggg gtgaggccag caacctgcgt   2460
cactcgcctg agttcctgtg tttcctgttt cacaagatga aagaagagtt cccgtccgtc   2520
cgtcactcag agcgcgaggc tggatacttt ttggatacgg tggtgacacc tgtctacggc   2580
ttgctgaagg ctgagatgac ttcaaagtac gaccatgagg accgtcacaa ctacgacgac   2640
ttcaacgagt tcttctggac gaagagatgt ctgaagtatg actacaaaca cgaagaggtc   2700
attgatttgg cgtcacccaa tccggctatg atctacaaac agaagcagca gcaacgtcaa   2760
ggtctgactg gccttggagc ccaaaaggct cgaggtggac tcaacggtgg ctcgaacggc   2820
tccaacttgt tcaacaagcg tcaaagtatt gccgagggat tcaccgagtc tgccaagacg   2880
ttcgttgaga agcgtacgtg gctgctaccg ctgcgcgctt tcaaccgtat cttcaacttc   2940
cacgtcatcg cgttccactt cttggcaatg ctcgcgttcg cgaatgagca agagatggac   3000
ttccaggacg cctgcaagat tatctcgagc actttgatat ctcacttctt gctggacatt   3060
ttacgtgatg gactcgacat tttcgctgtt tacgacgagc accggaaagt attctcaatg   3120
gcgcgttccg tgatgcgtgt gtttctgcat ctggctcttg tggtggtcac gtcgatgtta   3180
tactggtatg cgtgggcgta cggtggtgcc tggtggcagt cgtactacgt gaccgcggtg   3240
ctattccacg tgccaggcct gattaactgc gtcatgcaag tgatgcctgg tcttaccaac   3300
tggacacggc gcacggcgtt tgctcctgtt gcatttatcc gtgacattgt gagtccgatg   3360
aaccgcttat acgtgggtga caacgtgctg gatccggagt cgatgagcgt aggctaccag   3420
ttcttctgga tgtcgctatt ggcttggaag ttatacttcg gctacgagtt tgagatctac   3480
ccgcttgtgg tgccgagctt tctgctgtat gctgaccacg tggagaacaa cgtgagcatg   3540
attacgacag tgttcctcat cttcctaaac tggatgccgt tcttcttggt gttctgcgtt   3600
gacattacga tttggaactc gatctggatg gcattcacgg gtacgttcgt tggcttttcg   3660
tcgcgcattg gtgagattcg caacttcacc cgcgttcgat ctgcgttcag tcgtgctgtg   3720
gatgcattta acgcaaaggt gattgcgcga agctccaaga cgggacttca actctcggac   3780
agcaatggca cgtcgtatgg atcgacatca gtaggtcacg aggtgcttga tcgtgttgcc   3840
```

-continued ggtggtgcgg atccgacgtc ccgcctcctg ttgcagcgcc ggacatcagc ccatgacgac 3900
gagactccgt tactgtcttt ctcgcgtcgc aaacagacgc ctacggagcg ccaagctgct 3960
cgtcgccgca agtggttctc gttctctgtg gcctgggaca ctatcatcga tagcatgcgc 4020
gcggatgatt tgatctcaaa caaggagaaa tctctgcttc atttccaccg tcttgacggc 4080
taccagcgcg aaatttacct gccgcagttc caacttgctg gttgcttcga gaactttacg 4140
tcgcacattc ttgatattta ctcgtcgaac aacggcaagg tctcggagcg tgtgctgcaa 4200
gacaaactac tggaaattct cagtgataac ccaatggtgg aggagtcact tgaagagata 4260
tgggagcttg cgaactgggt gctggttaat gtgcttggtc cctgtcacgc gaatgatgtg 4320
aagtacatca catgtgtgct caactcgtgg gccgctcgtg gtgtgttccg tgcgctgaac 4380
ttgcaaaagg tggctccatg tggccgcgct ttggcgggtt tgatctcgct cttgaaggcc 4440
aacgtccgag gatggaagag caacgccaag gttatccctg ttcgcaaaga cccatccgac 4500
tacgcttcgt acgagtttcc gcaacagtct agctcctacc gtccttcgtc ggggcttact 4560
aagtctgcaa gtacgacagg tctgtcgtcg ttgggtctcg aaccacctcg tcgtagtcgt 4620
ggctctggtg ttgcgcgtat tgcacgtatg cagcagcaga cgcacaaacc agctgtcaac 4680
aatggcaagc ttactcattc tatctccagc tctcacatca tgcagattcg cgagcgcgtg 4740
cgtacgttcc tgaatcttgg aaaggagatt ctggcccacg tccacgagca agaccccgtg 4800
ttcgctgaaa gcaagggaat ttcggatcgg ttgacgtgga ttcttacaca ggagcgtggt 4860
tttatgtggg acgataatta tacgggtgaa caaatcactc tcacagcgtt tgagagccac 4920
accgatgtgg tgttatcgca tctgcacgga cttttgacct tgcagaagat tgatgcggag 4980
ccccagtcgt acgatgctcg tcgccgcttg ctgttcttcg tgaattcgct gttcatggac 5040
atgccgcttg ctccgctgct cgaggaaatg aagtcgtgga gcgtcatcac tccgttctat 5100
gccgaagacg ttctgtactc cagaaaggat ttggaaagca aacaggacgg tctggacgtg 5160
cacacgctgt tgttcttgca gacgctgtac aagcgagact gggagaactt cttggagcgt 5220
gtgaagccta agaagaacat ctggaaagac ccggagactg cgatcgagtt gcgtatgtgg 5280
gcttctctgc gtggccagac actgtcacgt acggtgcagg gtatgatgta cggtgaagct 5340
gccattcgtt tgctggctga gatcgaacaa gttccccaac agaaacttga ggagttgatc 5400
aacacaaagt tcacgtacgt ggtggcctgc caaatttatg gacgtcagaa gaagaacaac 5460
gacccgaagg cgagtgacat tgagtttttg ctgcaccgat tccctaactt gcgcgtggca 5520
tacatcgatg aggtccgtgt gaactaccaa aaggaacagt catacttctc ggtgctcatc 5580
aagggcggcg aggaactcgg ctcagttcac gagatctacc gcgtgcgtct gcctggcaat 5640
cctatcttgg gcgagggcaa acctgagaac cagaacgcag ccattgtttt cactcgcggt 5700
gaaaatctgc aggctatcga tatgaaccag gatggatatc ttgaagagaa cttgaagatg 5760
cgaaacctac tcgaagagtt tgacaagggt acggcagacc ggccgtacac gatcgtgggt 5820
atcccggagc acatattcac gggtagtgtg agctcgctgg caaactacat ggcgctgcag 5880
gagacgtcgt ttgtgacgct aagtcaacgt acgttggcgc gtccgctgcg tagccgtctg 5940
cactacggtc atcccgatgt gttcaacaaa cttttcttca taacgcgtgg cggtattagc 6000
aaggccagta agggtatcaa cctcagtgaa gatatctttg ctggctacaa caattgtatg 6060
cgtggcggtt ccgtgacttt cccggagtac accaagtgcg gcaagggacg tgatgtggga 6120
atgcagcaga tctacaagtt cgaggcaaag ttagcgcagg gtgcagctga gcaatcgcta 6180
tcgcgtgacg tgtaccgtat tagccagcgt ctcgactttt tcaagttgtt gtcgttctac 6240
tacaaccatg tgggcttcta cctggcgatg tcaatcatca tctggactgt gtactttctg 6300
ctgtactgca acttattgcg tgcactgctg tcggttgagg gtgttggcgg tcgtgaaccg 6360
gtattgctaa gtaagctgca gttgatgctt ggatcggtgg cattcttcac tactgcgcca 6420
ctgctggcga cgatttcagt cgagcgtggc tttaaggcgg cgttgaacga gatcattgtc 6480
ctgttcgtga ctggaggccc gctgtacttc cttttccaca ttggcacgaa atggttctac 6540
ttcggacaga cgattcttgc tggtggcgcc aagtatcgtg cgaccggccg tggattcgtg 6600
acaaagcact cttcttttga tgagctttat cgtttctacg ctagcagcca cctctatgct 6660
gcagtggaga ttgccattgg gctttccgtt tactacaagt tcacggtcgg caatcagtac 6720
ttcgcgctga catggtcgct atggcttgtg ttcgtgtcat ggtactggtc gccgttctgg 6780
ttcaacccac tggcgttcga atggtctgac gttatggagg acttccgtct atggttcaaa 6840
tggatgcgtg gtgacggtgg taaccctgat caatcgtggg aggcgtggtt caaagaggag 6900
aacgcgtact tttcgacgct tcgaccgtgg tccaaggcgt gcattacgat caagggcgtg 6960
ctgttcgcgt tgatcgccgt ctctatctct tcgacgagtg acaaatatca ctcgatcttg 7020
acggaaacca cgtggcttcc gctgcttatc tgcttatcga tggccgcggt gtatcttagt 7080
gcagaggctg tcttcttcac ctcgtcgcgt tcgggcgaga ccgggcttgt tcgcttcctg 7140
aagctccttc tggtgattgt gctgggcgct ggtctgattc tcgctttcat ctacgcggac 7200
ggtatgtggc agatgctgct gagtatggga tatctcgctg cagctatggg ctgttgggcg 7260
cttgtgatcc ttggtagcaa ctcgcgcttt gttggaacgc tttacttcgt tcatgacgcc 7320
gtgctgggtt tggtttcgct gagtctcatt ctgttgctct cggcgctcta cgttccgggc 7380
aagatccaga catggctact gtacaataat gctttgagtc gtggcgtggt gattgaagat 7440
attctgcgag ccaactcgag caatgatgaa cgcgatgatg atctgtcagt gcagcagatg 7500
cgctccatca tccttgagca gcagcgtttc atcaacgctc tgactgctag cggcagcgag 7560
actgacatcc gcggtgctgg tcctgggaag aaagaagatc taatgcacgc tatgagcgac 7620
aacacgctga acgcggtact gaggaatatg tcggagtcgg aactcagtgc gctgcaggac 7680
tcgtcgattc gtctgcaggc catcatgtcg gaggaggagc gcaaggccgc acaacgcaag 7740
cagcaacaag aagagcagag actcaccgag gcaggaatga actcgtcgtt gtcgcgcacg 7800
cgtcgtgcct tctccacgag cgatttctcc gccatcccgc tgaatgctag cccctacagt 7860
cttgctccta ctcaggatgg ttccgctgca cccgtcaacc gccccactaa cggttctgct 7920
gctcacggag cttatcctga tgtgtag 7947

<210> SEQ ID NO 36
<211> LENGTH: 6744
<212> TYPE: DNA
<213> ORGANISM: Phytophthora infestans

<400> SEQUENCE: 36
atggccacga cgcccggcgg caagatggac cggcgccgcg ccggctccaa ctacttccag 60
ctcgatgcgg accgcaagcg caacacgtcc aacaaccgca gcaactacgg cgacggccgt 120
ggcaccttcg gagaccgctt gagcttgatg gaggtgcttc ctcccaacac acagggcggc 180
aaccagatgc gcggcggtgg cttacagggc gactttgcgg acgaagtgtc gatcgatttt 240
tgctgcgagg tactgtacaa caagttcggc ttccagtcag gcagtgtgga caaccagcgc 300
gagcacgtgc tgctgctatt ggccaattcc aaggcgcgtg ccaagcccca ggaccctccg 360

-continued

```
ggacaccacg tcgtcacgct gcacaaaaag ctcatgagca actacacgga atggtgccag    420
ttcatcggcg ttcccagcat ctcgtactcg ggacagccac agggagacct caagaaccct    480
ctgcacatgg acattatgct cttcctgttg ctatggggag aggctggtaa cttgaggcat    540
atgcctgagt gcctctgcta cttgtaccac cagtcgctaa acttgctgaa ccaggacttc    600
ctcggtcagc agaaagtacc tgaaggttgg tacttaaggc aggtggtgcg ccccatctgg    660
aaggaggcgt ctaacatgca gaggaagaac agcttgggca agaacttgga gcacacccaa    720
gtgcgcaact acgacgatat caacgagtat ttctggaaaa aatactgtct taacgtggat    780
gtcacgcaga tcggcgagga gctgaccaag aagcacacca agacatacta cgagcaccgc    840
agtatcttca cgctcgtact gaactactac cgtatttttc agttcaacat gatgttcatg    900
atggtcctga tggcgatcgg ctttatctcg gccatctcgc ctagcggagg acagcagtgg    960
ttcgctcagt tcgggtctat gggagaagtg gttgagcctt accagaaaca ggacgttaag   1020
ctgacctacg tggggattgt gttcgccctc tcctcgatgg gattctgcaa gaccgtcctc   1080
gaagcgtgtc acggatggca cttactcact gccagtgagt cgtcacagac gtcgtctcgt   1140
tcgttcaact acggtggtgc ccttgtggtt cgaatgctct ggaatggcgc gttcgctggc   1200
attttcggct tgatgatcta caccccgttg atcacgagca agaacacaga actgctcgat   1260
aaggctgcac cggcgtctgt tgcctacatc ctgcctggcg cacttattat cgtcgtgcag   1320
gcctttgctc catcggttgt aaccaaatcg tttgcggcca agtttatccg tgagggagaa   1380
acgtgctacg ttggccgcaa catggcgcct ccactgagct accagctcaa gtacatcact   1440
ttctggatca ttctgtgggc gctgaaggcg ttcgtctcat acttcattct agttcgccca   1500
ttggttctcc cgtcgctggc catttacgag atggagctcg agtacggtag caatgttgtt   1560
tcgttccaca acttcggagt catcgctgcg ctgtggctgc ctgtgatctt catcttcaac   1620
tacgataccc agatttactt taccgtgttc caggctacac ttggtggcgt tcagggtctc   1680
atcatgaaga ctggcgagat tcacggcatc aaggagatta ccaaggcttt ccgtgtggct   1740
ccacaactct ttgaccagaa ggttgtgacc aatctggctc gctcgaacga cgctgcggct   1800
gacggatctg ctgctgcata ccagtcgcaa atgatgctgc gcttcgtggt cgtctggaac   1860
gagattgtca actcgttccg cgaaggtgac ctggtggacg acaaggaggc tgccatcctg   1920
cagtatgaca tccagagctc gggcgacgtg ttcgaacctg tgttcctttc ggcgggtaaa   1980
ctgatggaag ctctggacta cacggttaag attgccaagg aaggtaaggg cgactcgcag   2040
cttcaagtgt acatggtgca gaaggattgt ctatcggctg tgcgcagctt cttcacagcc   2100
agcatgtacg tgatggaggc tctgctgggc agtgacgatg cagacattct tgatgcgctg   2160
cgtcaaatgg aggcgattgc tgcgaacagc agtttcatga gcacgtttga cgccaagagt   2220
ctagtgcagc tgcgcacagt ctcgatggag ttcctggaag ctgtgatgga tctgcccgac   2280
ccggatgcgc agtcctcgca catgacatcg tctcgagtgc acaccatggg agttgtgcgt   2340
aacttcgtga ccaagatgga aaacctgctc aacgctattc gcattttcgc caaccgcccg   2400
gagctcgctg ccaagttcag caactctaag ttctgctcga gcgccaacgg ctacgtgttt   2460
gctgctcgtg gcctcgtgaa cctgttccac aacgacactg cgatgggtgc tgctacccgt   2520
gcgtacctct tgatgtcgct cgagaaggcc gatgctatgc cccgtgtgcc tgaggctcaa   2580
cgtcgtcttg gtttttcat gaagtctctt ttgatggaca tcccgcagtt gacgtctgtg   2640
aaggagatgc actcgttctc cgtcgtgacg ccgttctaca gtgaaagtgt gttgatctca   2700
```

-continued ttgtcggagc tgaacgatcc gctggccaac cacccggtct tccagaaggt ggaggagaag 2760
ggcaagaaca ttactattct gaagtatctg attaccatcc accccgagga gtgggagaac 2820
tttttggaac gtattgatgt gagcactgca gaggaagcac aagccaacta cccgctggaa 2880
atccgtctgt gggcgtcgta ccgtggtcaa accctggcac gtactgttca aggtatgatg 2940
ctgtacgagg atgctatcaa gattcttcac tggcttgaga ttggttcaag tcccggcaag 3000
tcggcggagc agaagcaggc tcaacttgag gacatggtgc gtctgaagtt ctcgtacatt 3060
tgtgcgtgtc aggtgtacgg taagcatcgc gcagagggca aggcccaggc cgatgatatc 3120
gactatctgc tcaagacgta cccgaacctg cgtgttgcct acgtcgacac catcgtgatg 3180
gacggtggca agcagttcga cacggtgttg atcaagagtg aaggcaatga aattgccgaa 3240
gtttaccgct acgagctgcc tggagacccg attcttggtg aaggtaagcc cgagaaccag 3300
aacaacgcgc ttccattcac gcgtggcgaa tacctccaga cgattgatat gaaccagcag 3360
cactacttcg aggagtgtct gaagatgccg cagcttctgg tgactgctga cctgcaccct 3420
tccaagaaac ctgtgtccat tattggtatg cgtgagcaca ttttcacggg taacgcttca 3480
tcgctgtcaa agtttaagtc gtggcaggag ctggtgttcg tgacgctgtc tcagcgtgtg 3540
ctggccgacc cgctgtatgt tcgtatgcac tacggtcacc ccgatatttt cgacaagatc 3600
attgctatgc ctcgtggtgg agtgtccaag gcttccaagg gcattaactt gtctgaggat 3660
gtgttcgctg gttttaactc gacgcttcgt ggtggtgtgg tgacgcacgt ggagttcatg 3720
cagtgtggta agggtcgtga tgtggctctg tcgcagattt ccatgttcga gggtaagctg 3780
gctaacggtg ctggcgagac gtctctcgct cgtgaggctc atcgtatggg ccagttcatg 3840
gacttcttcc gtctgaactc catgtactac tcgcacacgg gtttctactt cgccacgtgg 3900
atgacaattg tcacgacctt cgtgtacatg tactgcaagg tgtacttggc tctagcgggt 3960
gtgcagcagc agattgtgta cgatatgaac acgaccgctg tgatcaccga gaacatcgca 4020
aacaacttcg acgggcgtgt gttcaccgat ctgaaggctg tgctgaacac gcagttctac 4080
atccaagccg gtactttcct catgcttccg ctcatgtgtg tgtacttcgg tgaaggaggc 4140
ttcgtgcgcg gtatgactcg attcatcgac atgatcatca cgctgggccc tgccttcttc 4200
gtgttccagg tcggtacgac gatgcactac ttcgacaaca acatcgtgca cggtggcgcc 4260
aagtatcagg ctacaggtcg tggcttcaag atttcccgtg agacgctggt gctgctgtac 4320
aaggcgtatg caagctccca ctatcgaaag gcctgggagc tcatcgggtt gtgtcttgtg 4380
tacatggcgt tcggtaattt ttacatctgt cggaccgatg cggctgccaa cgacaacact 4440
tttgcgtccg actactgtga gactgctcag gcttacgggg tgcagacgtt ctcggtgtgg 4500
ttcatctcca tcttgtgggt ggtgggtccg ttcctcttca acagtgacgg tctggactac 4560
aggaaaacca aggtggatat ccagcagtgg tgcatgtgga tgtttgcccc cgaagactac 4620
aaggacgacg acccggccaa caagggaggc tgggtaggct ggtggaaggg cgatctggag 4680
cagctgcacg gctccaacat gatctcgcgc gtcacggtca tcctccgcga gtgtcgccac 4740
ttcctgctca tgttctacgt ggctacactc gagacgtccg acgtcatgta cgtggcgtac 4800
tcgttcggtg ctgcggtcgc gacgattgtt ctgcttggcg tgttccatgg ctttggtatg 4860
ggcatgcgct ccatgagccc ggtgacgcgc gctgtgatct acatggggac cgtcgcagcc 4920
atcgtgacgg cctacttctt ggccacttgg atcgtgctgg actggaaatt caagtacgcc 4980
atgtcgctct ggttcgccta cgtggctgcg ctctacggta tcaacgagtg cttccgcatg 5040
tggagtttcc caagctcgtc gatcgctggc attgctgtgt tccagcagct acagttcctc 5100

```
ttcgacttta tcttctgcat tggtatgatc atcccgcttg tggtcatgtc gtgcatcccg   5160
ttcctgaaca tcatccagac gcgtatgatg tacaacgaag gcttctccaa ggtcatgtct   5220
gcttcttcgc agtatgcctt ctctctggca gccttcatgg gaatcctggg cggtatcggt   5280
gtcggctggc tgttcaactt gctgtcaacg ctggagcagt ctgcgagttt cgcaagttac   5340
gtcgtcacgt acgatggcgt cctaagtgga aacgtgggcg atggcaccac gacgtacatg   5400
ctctacggtg cctgtgtggt gggtacgatc atcgctggct tcctcaactt cttcctgggt   5460
cgtcgtctgg ctattgttgc gggtggtctc ttcagtacgc tcggtatggt ggctgtcagt   5520
gccaacgacg atctccgttc gacgctgctg atgcctggta tcggtctgct tggagcctcg   5580
tgcggtattc tgctaccgtc gttggccatc tacatcttcg agatctcgac caaggagatg   5640
cgaggcaaag ccatgttgtt gctgggaatc ggcttcatca tcggcagttt gctgggcggc   5700
attttcgcga ccgtgaacca gctgggatgg atctggcaga cgtttgctgc ctgcatcgtg   5760
atcgccctgg tcacgccagt cgtcaatgtg ttcccagaga gtccgtactg ggtgctggat   5820
cgcaagggct gggacgcctg tgaagcctgt ctcgttatcc tgcgtcgtaa acctgatgtc   5880
caagaggagc tcaaggtcat gcgagaagag gaaacggcag atgaaggcgg cgccggcgcc   5940
tacaagttcc tcatcggtct cttcctcatg ctcgtgtcct ctctgactac tggtttcctc   6000
aacgccttca tcagctacaa gggagcgagc gagtacacgg accaagacca gctgttcgtg   6060
aacgcgatgg cgctgcagat ctccggtgct gcgatcgcca tcttctacat cgacaagctg   6120
gaccacaagt cgattctctt cggaacgttg atccctatcg ctatctgtgc tggcattctg   6180
ggcttcaacg agaactcaga gatgctggga gacaaagagg gctcgggtct gtacctcagt   6240
cttgtagtca tgctcatgta cttcttcatg ggctgggca cgagctctgc tctgtggtcc    6300
gcatgcgtcg gcatgttcaa tactcgcggc cgcgcctcgt ccaccaccat gctgttcgct   6360
atcttcttcc tggcggatat gggctacgtc tacttgcaca cggacgactc gatgatgcag   6420
aacgaatatt cctatctcta cgccatcgca ggcttcagtg tcgtcgccct ggtgctgtta   6480
atgggcgcag gcaccaagaa gaacggcgtc atctgtacca agtcagaagc tcagcgcgat   6540
cgcgaccgta tcgctcgtat gcgtgccgaa cgtgcaagtc gcaacacgcg gacgcctgga   6600
actgcgcgcc agcggaatct cagtcgcgtg cggtccaagt cgaacgctgg cggccagcgg   6660
ggcaacgcgg cgcatggcgg tggctaccaa atgtacgaaa cacccgccaa cgctgcgccg   6720
ccgctcatgc acgcgcgccc gtag                                          6744
```

<210> SEQ ID NO 37
<211> LENGTH: 2462
<212> TYPE: DNA
<213> ORGANISM: Phytophthora infestans

<400> SEQUENCE: 37

```
attcgagaga tttttcgaac tctgacatcg ttgcaaccat aacttgcctg cattaaggtg     60
ctcctcaact gtacccatgc cgagcaccca tcgactctgc cagtacgatg cttcaccaaa    120
gttttagtcc acaagaaaag ccgaaacgta catgtcgtaa cggaagccgt gcgacctttt    180
accgttcgtg cgctggtctc acgtagcttc attctccttc ttccctagcc agcaaaggcg    240
tctcccaaga tatcccagca attgtctatc ggttaagatc aaggagtaaa atgcactcgg    300
cgctgttctc gtgctcaact ttggctttga tcacgagttt ggtctcctca gagcgtgccg    360
actcgatgat caaatctcgg tctggattga gcccctgggt ggacgttgac acccccgaga    420
```

```
gtgcactcaa cgtcacgtcg tcgcgtggag atacgtggac gttggtcatg agcgacgaat    480
ttaacgttcc tgggcgtaat tttacgcccg gttcggatca catgtggacg gcgttagaaa    540
tgcccgacgg tgtcaatgca gctctcgaat actacagctt caatatgacc gataccgtaa    600
cggaatcgga cggtcgtggt gtcttccgga taaagattat ggaagaggac aacatcacct    660
acacggtgtg gaacacgtac gctaagcctg cgggtttcga gacccatcac atgtactacc    720
gagccggtat ggtgcaatcc tggaacaaat tctgtttcca aggaggaagg atggaagtgg    780
tggctcaatt accagcaaca accagctcta gtaaccccga tatgggtgac atcaaaggtc    840
gcgtcaagac gaacagcttc tatcccacgt ggcctggtat ttggcttcta ggaaatctag    900
gacgagctct attctcccaa tcgaccagtc ggatgtggcc ttggagttac gacgaatgtg    960
acgaaaaatt cgaatccagt caaagaatca gtgcgtgtga cggtaatcca ggaagtggat   1020
tgaatgctca tcaaggacga ggagcgccgg aaatagatct actggaagga ggaggtgtag   1080
ccatctccac aagtatccag gtcgctcctg gaatgcccga taaattccgt atcattgctc   1140
ccacggatga taaaagtccc ttctgcgtct tcacggccga gtgtactact attggtgcta   1200
actttcctgg gatcccagcc aaagcgtacg aagctcgaga ttatgaaagc tggtatcaag   1260
gactacggta cgctccaaat actctttgta gcccagttgg cagcttgatg caagatccca   1320
aaacggtgct tgcaaatgcc gagaaaggct tcacttctaa tacgtgtaaa ggagtcaatg   1380
cgtgtccagc ttcgggtgac ggatactccg atttaggctt gatcgacggg aaagggcctg   1440
attactgggg ggttaacaaa gaaggcggct gtatgccggt tattaacgga tacacgggag   1500
ctttcctatg tgaccctgac agttccaaca aaaaatgttc ctctccgtta ggtgcggaag   1560
aacccaagag taaagttatg gaaccattcg agtatcagat ggacgccctg tccgctaatt   1620
ggccagttca gctcgcagca tatacaagtt atgtgaaata ccaagtcgaa tgggtcatgg   1680
gctcacaagg ttacattcgc tggatggtcg aggatattgt gatttttgaa attccagccg   1740
agtcggtcga gaatgttcca caagatgctg ccaagtccaa ccctaagaaa ctcatgttgg   1800
aagaacccat gtacgtgatt ttcaacgtcg ctctgtcaac tagttggggt accacgccac   1860
cgaatccagg gtcgccatgt cgtggagatg ggagcaatgc gcaacataac gctatttgtg   1920
acggtttccc catgttcatg aagatcgact acattcgtat ctatcaggat ctctcttcca   1980
actccacgat ggctatcggg tgtgacccgt ctactcatcc gactaaacaa tggatcgagg   2040
atcacattga tgagtatgag acgacggaga ataaatggat tgaggttcac ggtggagcca   2100
attgcaagac tgataacgac tgtacggtca gtacttctca cattttgacg gggaaatgta   2160
gcaagaaaca tcgctgtaga tgcggatctt ccggtgcttg gggtggtcca cgttgcacaa   2220
ctccactagc tgatacagcg aatggagaag gcttcggacc accaacagtt attacgagct   2280
tggttggtgc attcgtcatt gtgcttttgg tctttgtggt gtacaagata atggaccaac   2340
gcagcaagaa ggcgatggtg ggagctggga ttactcaacc agcaattctc tccaagatcg   2400
agatggacga catcccacgt tcaaataaaa gccagagcgg ctcggaggat aaggtggtgt   2460
ag                                                                  2462
```

<210> SEQ ID NO 38
<211> LENGTH: 942
<212> TYPE: DNA
<213> ORGANISM: Phytophthora infestans

<400> SEQUENCE: 38

```
atggctccac tgccatccgc aaccttgacc acacccgacg tggctcctgt cacagctacc     60
```

```
accgcctcgc agcccttcga cgacctagtt gacaaggtcg agagtggcta tgcggctatg    120

cctaccaccc caaaggcggt ggctcccttc ccaacctcca aaccgcaagg tctccagcgt    180

ttcgccgttc agagcgtgca cctgcgcgag tgcttcgccg agttcctcgg caccttcgtc    240

atgatcgtct tcggtatggg cgtcaacaac caagtgacca actcacacga cgccaacggc    300

acgtggctca gcatcaatat gtgctggggg attggtgtac tcatcggcgt ctactgctcc    360

gagggcatca gtggtgctaa cctcaacaca gccgtgacgt tggcacattg cgtgtacggc    420

cgtctaccat ggtggaaagc acccggttac atgatctcac agctattggg cgccttctgt    480

ggagctttca ttatctacgt catgcagtac cagaacctca acgtcattga cccgtatcgc    540

gagaccacac agagcagctt ctcgacgtat ccgagcgaca acatctccaa ctacacagcc    600

ttctacaccg agttcatcgg tactgctatg cttgtgctca gtatctacgc catcacggac    660

aagcgcaaca gatctgccgg tctcgtgggt tctcccttcg ccttctgtct aatgatcatg    720

gcgttgggca tggcctttgg catgaacacg ggctacgctg tgaaccctgc acgtgacttc    780

ggcccccgca tcttcacggc catcgcgggc tggggctcca aggtctttac cactcggaac    840

tactacttct ggatcccgat cgtggccgat tctatgggcg gaattgctgg tgctggactc    900

tatcggctgc ttgtggagat ccaccaccca cccctctcgt ag                       942
```

<210> SEQ ID NO 39
<211> LENGTH: 1636
<212> TYPE: DNA
<213> ORGANISM: Phytophthora infestans

<400> SEQUENCE: 39

```
atgtccgacg accaagtgcc accgttttcg ctcggtacga aacaccttac acgcatgacg     60

tgcagcgcac agttcagaga tgactaactg gccatgctgc cgctacgtgt atttaccaga    120

taagccgcgc cacgatactt cgacgtacgt cggtcggtgg cgtaagtttg cggagctcgt    180

gtcgccaaag tacgtcaaac aaggtagacg atggaaaaag tgtggctcta aacatcatgc    240

tggggcttta ggtggctctt tctaagctcg gagcagattc agcacgcgac gcagactctg    300

gaggacttcc gcaacggtaa aatcgcccct ggtcagttca aggatgcgga actttggaat    360

cttcgccagg gtacgaaaca atgcgacagg atggtaccaa cttgtggttt ttgctgacgt    420

tttggtgata attgaatcga tatgtagcgt acgaggctgc cgtgcaccct cagactggcg    480

agacagttcc ggctgtgttt cggctgtcgg ctttcgtgcc tgtgaacatt cccatttgcg    540

ttggcatgct gctcgctcct gccacggtat gtaaagtctt gctgcacttg taacaatagc    600

tttattttaa tttaaatgct cacttaaata tgcttacagt tgggaaacac gatcttctgg    660

caatgggtta accagagcta cagcgccggt ttcaactacg ctaaccgcaa cgccagcagt    720

gaacaggaca actccaccat cttcagtacg aagttctcga tgctaatggc cttctttcag    780

cgttctaaca cggctctttg catcgtatca cagagtcgta cgctaccgcg acgctcgtgt    840

cttgctcgac tgccgttggt ctgggtaaga tggtggagaa agccaagaga ctttctccca    900

gcacgcgttc cttcctcgga aaggttaaaa ctgctaaatg ccgaatgctg tgctccttat    960

gtgactgaat ttttgggctg caacttgatc agatggttcc tttcgttgct gtcgcgagcg   1020

caggtgcttt caacgccgtg tcgatgcgct tcaacgagtt ccagtacgtg tagagtgtct   1080

tgcactggaa atatgatgct gttgtgctca ttggagtgtg gtgatgcgtt acagagaggg   1140

aattgatatc atggacgagc acggagatgt tcacgggcgt tcagttgccg ctggacgtca   1200
```

-continued

```
gtcgcttggc caagtggcac tcacgcgtat tgcgctaccc atgcccagta cgtcctcgca   1260

ttgacaagct cttcttgggt gaattatgtc taatattggt ggacttggac agttttgctg   1320

ctcccgccgt acctgtatga gatcatgaag aaaaccaaca tcatgcccaa ggccaagtac   1380

ccgaagcttg ctgcggagct cggtacgtgc attatttctg ccatagtccg cggtaatgag   1440

ctaacttatt gcgtctctgc ctgcatctat gatagtcgtg ttaacgatgt gtctgtgggg   1500

tgccatgccc agcgctgtgg cgctcttccc gcagttggga acgatttcgg ctgacagcgt   1560

tgaggaggaa ttccgatctc gggtggatcg caacggccag cccattcgtc acttcatcta   1620

caacaaggga atctga                                                   1636
```

<210> SEQ ID NO 40
<211> LENGTH: 960
<212> TYPE: DNA
<213> ORGANISM: Phytophthora infestans

<400> SEQUENCE: 40

```
atgagcaccg ccaataaaga agcatctccc tttgtggagc ttcgccgtct taactttgcg     60

ttcgccaaag ttactatcgg tggccaactc atcaatcgct tgcagcatga ccccgctact    120

gctgacgcca tggaagacga cgatcgagtc ctgcgtgacg tgaatctaac gctgcagtct    180

ggtcagcgcc tgttggtcgt gggtggtaat ggagctggca aaagcacgct actcagtatc    240

ttggctggca agcacctgac ggctgacgac acggcgctga tcttcggtcg agacagcttc    300

cgtgacacga cactcaacgc tttaaggact ttcgttagtg ccgactgggg gcagcgctcg    360

gtggcgttcg caacgcacgc aatggcttac tcggctgaca tggcggtgga agaaatgatg    420

acgaaactgc agagtgaaca cccggagcga cgccaaaagt tactgaaggt gttgcgtatt    480

gacccaaagt ggcgtttaca tcgcctgtcg gacggtcaac gtcgccgcgt tcagctcttt    540

ctggcgctac tgagaccttc gcagctcatc gtactggacg aagtgctggg aatgctcgac    600

atcatctcgc gcgaaaacgt actggcattc ctaaaggagg aaacagagac tcgacaagcc    660

acggtgttgc tagccacgca catcttcgat gggacggacg tctgggcatc tcatgtgctg    720

tatattcgtc gcggtactgt tgggttctat ggtccgattc agcagtgtac tgatggaggg    780

aagatcccga tgtataaggt ggtggaacac tggctacgtg aggaattggc cgacgacgac    840

cgtgtggaat gcgaggcggt gggcccaagt ggtgagttcg acctgggcaa cgcgcagaac    900

cgcgcaggag ggtatgccga cggtcgactg ggtggtgtcg atgtcaccac atcgttttaa    960
```

<210> SEQ ID NO 41
<211> LENGTH: 510
<212> TYPE: DNA
<213> ORGANISM: Phytophthora infestans

<400> SEQUENCE: 41

```
atgagcgacg gtactaagct cattgccgtg atcggagacg aagacaccgt cacgggcttt     60

atcctcgcgg gtgtcggcca tcgaacggcc gagggaacca actttctcgt cgtcaaaccc    120

tgtgcgtcgg cattcccgaa aggatttttt taaagcttag attaactact aacacgcgtc    180

acatacgacg gtgctgcagc tactccaatc tccgctattg aggccagttt ccggacgctc    240

tcgagccgtg acgatatcgc aattatcctc atcaaccagc acgtacggca tcctagttag    300

aacccactct gaggtataag cctttatgtt tttctcactc gcttgatatt attgtttggg    360

caggttgctg aggagatccg tcaccttctc aacacgtacg acaagaccat tcccacggtg    420

ctagagatcc cgagcaaaga ctcgccttac gacccagcta aggactatat catgaagcgc    480
```

-continued

```
gtgaatctca tgcttggagg agagtcgtga                                   510


<210> SEQ ID NO 42
<211> LENGTH: 1491
<212> TYPE: DNA
<213> ORGANISM: Phytophthora infestans

<400> SEQUENCE: 42

atggtcgctg aagacgcggt gttcacggaa gcgaagacgc ccaaggccgg cgatgtccag     60

gccggcagat ccgtcccgct ctcgccgacc ttctggttca gcctcgcggt gctgctcctg    120

ctccccttcc agttcggctg gtcggtcggc cagctcaacc tcacgacctt caacgacgaa    180

gacgagtgca acgcgcgacc tctagtcgac ggaacgtgcc tcatgtttcc cggtcatagc    240

agcacggaat ggaccttgat cgtgaacgcg tggattgtag gcggtatgat cgggagtctc    300

ggttgtggcg ttatctccga acgtttcggt cgcaagaagg tattgctggc gaacgccgtc    360

gtcatgttgg ccggcgctgt cattcaagcg agtacgtcga gtatctcggt ttttatggtc    420

gggcgtatcg tcgccggtat cgcgtcgggt tgtgcgacgg gtatggtggg tggctacatc    480

agtgagatta cacccccgag tctccgtaac tcgtacggca cgttcatgca ggtatctctc    540

tctgccggta tcttagtagt gaccatcagt tttttcttcg cggataccag tagcggctgg    600

aggtacatcg ccgcatttcc cgttcttaac gccggtttct tcttggcgtt cgcaccgttc    660

gttcttgtag agagtcccgc gtggcttttg gaaaagggcg accgggagca tgcggagcgg    720

gagatcgcca gactttacgg cttcgatttc gtcccagtag cactgacgtg gatggaacca    780

ggtatcaata ctgacctgga gtcagaggaa ctgtgcggcg aacagcacga aggcggcaca    840

ttgtcgctgc tgttttcgcc gctctttatc aagcaactgc ttgtggctct tggtgtatca    900

gctgcgcaac aacttacggg tatcaacgcg gtgtgctatt actcgtccga tatcttctcg    960

gatgcaggga tgtcggatgg tcgtgtgggt ggcgtcatcg tgtacgtgct gatgttacta   1020

ccgacgatgg ctgttgcgcg attgtcggag cgattcggca accgacggct tctgcttact   1080

ggactggccg ggatgtttat tagtgctacg ggtataactt tggcgcttgc gttgtcggtc   1140

gaggtactct ctatcgtctt catgggtaca ttcgttgcgt tcttctctgc gagcgtgggg   1200

ccgcttatct agcctatcac ggccgcgctg ttcacggact cggtacgcgc cactgccgtc   1260

tctatgtgca tctttatcaa ttgggtatgc aacttgatca ttggcgtctg cttcccgtac   1320

gtctcggatg cgctagacga gtacaagttt gtccccttta tggtgaccac cgctgcgttt   1380

ttcttcttca ctcagttttg gatcccggag actgcaggta agagcaccga ggagatccaa   1440

gccacgttcc gatctaggaa agctcagaag ccggtggtgg tgttaagctg a            1491


<210> SEQ ID NO 43
<211> LENGTH: 2462
<212> TYPE: DNA
<213> ORGANISM: Phytophthora infestans

<400> SEQUENCE: 43

ttgtgctact cgagtgcctt cttctccatg acgcagcaag acgttcgcca ggcgctggac     60

gcccccgcat tagcagccta catccactcg cgactgggtg catcgcacgg cgccatcgcg    120

tccatccgtc agttccagca tggccagtcc aacccgacgt acctcttgac aatggccggc    180

tcgaaagcca agtgggtgtt gcgtaagaag ccgcacggtc agatcctgcc gtcagctcac    240

gccgtagagc gcgaatatcg tgttctagag gctctggagc actcggaggt gcccgttccc    300
```

-continued

```
cgcgctgtgt tgctatgtga agaccccaaa gtcattggca cacctttcta cctcatggaa    360
tacatacatg gtcgtatctt ccaagaccca tcgctgcctg gcattaaacc tatgtatcgc    420
tacgccatgt acagctcggc agtagacgcg ttggttaagt tgcacgagct ggactacaag    480
aagatcggac tggccgactt cggtcgcccc gagaagtact gccaccgtgt cgtgacgcgc    540
tggagtcgac aagtccaaag tggccagaag gtctttagtg aagctggagt gaaggagaac    600
ccgaagatga cgcagctgca acgttggctg gagcagaacg ccgacgacgc cgagaaggcc    660
acgaccagtg ccgagggagc gagtatcgtc cacggagact tccgcattga caacatgatc    720
ttccacccga cggagcctcg tgtgttggcc attctggact gggagctgtg tactatcggc    780
aatccgttct cggatgtagc cacattggcg tcggcctaca gactgccact ggacaactcg    840
aacacaatca tgacgcctgg tctctcggat gctccgttga agacactcgg catcccatcg    900
gagagtgaat tgttgctagg ctactgtcgt cgtgccagac ggttccctct acccactcag    960
acgtggcatt ttttcatggg gatgatcgta taccgcttcg cagccatctg ccacggtgta   1020
tacgcccgcg cactgctcgg caacgcgtcg tcggccaacg cagcatgtgc caagacgacg   1080
atggaccgac tcttggccat gagcgacgac atcatggacg catcggctga tatttacccg   1140
gagccggagc tgacgcacat tctgccgttc ccgatccgtc ctcatgctct gcagatgtac   1200
aagaagctgc taaagttttg ccagaaccga gtgtaccccg ctgagtccgt ccacattgct   1260
cagatcgcca aggcgagaga agaaggacgg gagtggcaga gtgtgcctcc tgttattgaa   1320
gagctcaaga cggaagccaa ggcgctggga ctctggaacc tcttcctgcc tcagtgtgtg   1380
gtgccagctc tggatggcaa tggaccagac gtcaactacg gtggagacct gacgaatctc   1440
gagtacggac tcatgtgtga ggtcatggga cgctccattg tgttggctcc ggaggttttc   1500
aactgctcag cacccgatac cggcaacatg gagatcttga cgcggttctg cactgtggag   1560
cagaagcatc agtggcttgt tcctcttctt caaggtgaga tccgatcgtg tttcgcgatg   1620
acggagaagc gtgtggcttc gtcggatgcg acgaacatcg agacgcgcat tgtacgcgac   1680
gaacagcgtc aagaatacgt catcaatggc cacaagttct acatctctgg agctggagac   1740
ccacgatgca agatcattgt gctcatgggc aagcacacgg aacgagccaa ggagagtcca   1800
ttcaagcagc agtcgatgat cctcgtgcct atggacacac ccggcgtgca ggtcgtgaag   1860
cccatgcatg tctttggcta cgacgacgca ccgcacggac acatggagat gctgttcaag   1920
gacgtgcgtg tgccgttcag caacgtgttg ctcggtgaag gtcgcggctt tgagatcgct   1980
caggctcgtc ttggacctgg ccgtatccac cactgtatgc gagccatcgg agctgctgag   2040
cgttgtcttg agctgatggt gcagcgagcc aagacacgca cagcgttcaa gcagctcctg   2100
gccgagaatc cgctcgtgtg ttcgcagatt gccaagtcgc gttgtgaatt ggacagcgcg   2160
cgcttgttga cgctccaggc tgcacatcag atggacaagc acggcaacaa ggtggcgcaa   2220
caggccatcg ctatgatcaa gatcgtggcg cctaacatgg cactggacgt ctgcgaccga   2280
gccatccaga tccacggcgc ttctggcgtg agtcaggact ttgtcctgtc ttacttgtac   2340
gccgccctgc gcacgctacg tatcgccgac ggaccggatg aagtgcacat gcggaccatc   2400
gcaaaactcg agctgagcca ctcgaagttg taagagaaat gtaaggcaaa agcaagcgtg   2460
aa                                                                  2462
```

<210> SEQ ID NO 44
<211> LENGTH: 20
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 44

atcccactat ccttcgcaag                                               20


<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

ttgatatcgc ggaaggcgag agacatcg                                      28


<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

ctaagggttt cttatatgct caac                                          24


<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

cgctcgaggc tggatctcgc gctgaggt                                      28


<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

gtggagaggc tattcggta                                                19


<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49

ccaccatgat attcggcaag                                               20
```

TRANSGENIC PLANT OF THE SPECIES *SOLANUM TUBEROSUM* WITH RESISTANCE TO *PHYTOPHTHORA*

CROSS REFERENCE TO RELATED APPLICATIONS

This application is a Divisional application of U.S. patent application Ser. No. 14/420,106, filed Feb. 6, 2015, which is a U.S. National Phase application under 35 U.S.C. § 371 of International Patent Application No. PCT/DE2013/000446, filed Aug. 6, 2013, which claims priority to German Patent Application No. 10 2012 016 009.7, filed Aug. 8, 2012. The International Application was published on Feb. 13, 2014 as International Publication No. WO 2014/023285 under PCT Article 21(2). The entire contents of these applications are hereby incorporated by reference.

SEQUENCE LISTING

The instant application contains a Sequence Listing which has been submitted electronically in ASCII format and is hereby incorporated by reference in its entirety. Said ASCII copy, created on Jul. 5, 2018, is named 245761.000009_SL.txt and is 100,249 bytes in size.

BACKGROUND OF THE INVENTION

The present invention relates to a transgenic plant of the species *Solanum tuberosum* with a resistance to an oomycete of the genus *Phytophthora*, to transgenic parts a plant of this type, to a method for its manufacture and to a means for external application to plants.

Even now, potato late blight caused by *Phytophthora infestans* is still the most prevalent and most economically important potato disease.

Throughout the globe, the pathogen results in loss of earnings, with harvest losses of more than 20 percent. This means that expensive chemical plant protection means have to be used, because the natural defence mechanisms of the potato with the help of which *P. infestans* is combatted or with which propagation can be slowed down and restricted is not sufficient or not permanent.

Natural plant defence mechanisms, such as the hypersensitive reaction at the infection site, lignification of the cell wall, the production of PR (pathogenesis-related) proteins and the synthesis of phytoalexins are indeed known to contribute to augmenting resistance, but they are always accompanied by an energy loss and thus a loss of earnings for affected plants.

Natural defence mechanisms in plants also include the expression of so-called resistance genes (R genes), the gene products of which interact with microbial avirulence genes (Avr genes) (gene for gene hypothesis) and thus induce a specific defence reaction. This resistance can, however, be interrupted if a pathogen such as *P. infestans* can dispense with the synthesis of the Avr gene and recognition of the pathogen and thus the subsequent specific defence reaction in the plant host does not occur.

Fire et al. (1998) have already demonstrated that double stranded RNA (dsRNA) can result in the sequence-specific degradation of homologous RNA. Starting from these results, transgenic plants have been developed in the meantime which, with the aid of RNA interference (RNAi) by means of host plant-induced silencing of conserved and essential genes, for example from nematodes or *Lepidoptera*- and *Coleroptera* species, can exhibit resistance to these pests in vitro as well as in vivo. In addition, the host plant-phytopathogenic fungus interaction can constitute an application of the concept of host-induced gene silencing (HIGS) to induce resistance (EP 1 716 238).

Van West et al. (1999) initially used the gene silencing method in *Phytophthora*, in order to carry out functional analyses of these oomycete-specific genes.

In WO 2006/070227, the use of RNA interference to control fungal pathogens based on contact of dsRNA with fungal cells outside the fungal cell was described for the first time. It proposes a method for the manufacture of a pathogen-resistant plant. In this manner, the RNA interference can be directed against one or more genes of a pathogen as well as several pathogens. *Phytophthora infestans* is mentioned as a possible fungal pathogen and potato as a possible host plant.

Previous studies have given rise to the hypothesis that host plant-induced gene silencing does not work for every gene and choice of the target gene is essential for functional silencing. Thus, for example, the plasma membrane H+-ATPase PnMA1 in *Phytophthora parasitica* could not be reduced sufficiently by host plant-induced gene silencing to deliver efficient protection against a pathogen (Zhang et al. 2011). According to this, selection of the target genes is also decisive for effective pathogen defence (Yin et al. 2011).

Recently, a screening system was proposed which was supposed to facilitate the selection of suitable parasitic genes for silencing constructs for the production of pathogen-resistant plants (US 2010/0257634). The identification of appropriate test constructs to induce phytoresistance in potato was also proposed by the authors. In this regard, target genes were defined based on bioinformatic analyses of genome sequences or based on sequence homologies to essential genes or virulence factors from known model organisms. That document does not contain any indications of the genes disclosed in the present invention for the generation of a resistance against an oomycete of the genus *Phytophthora*.

A method for producing a broad spectrum resistance in transgenic plants against multiple fungi is described in WO 2009/112270. In one implementation of the method of that invention, the broad spectrum resistance is directed against *Uncinula necator, Plasmopora viticola, Uromyces* spec., *Phakopsora pachyrhizi, Erysiphe* sp. and also *P. infestans.*

Furthermore, the development of *Phytophthora infestans*-resistant potato plants through RNAi-induced silencing is disclosed in WO 2006/047495. On the one hand, plants were generated which carry gene sequences of the rRNA gene from *Phytophthora infestans* for RNA interference. The silencing construct described in WO 2006/047495 directed against the rRNA gene of *Phytophthora infestans* comprises base pairs 1-600 of Accession number AJ854293 and with it 32 bp of the coding region of the 18S rRNA as well as the complete coding region of the 5.8 S rRNA gene of the blight pathogen. When selecting the target genes for HIGS strategies, with a view to applicability, it is vital that it has as short as possible or preferably no homologies extending over more than 17 sequential base pairs to the gene sequences of non-target organisms, as if there were, gene expression of the non-target organisms in the case of consumption of the transgenic plant or its harvest product could be destroyed ("off-target" effect). However, the sequence described in WO 2006/047495 comprises 32 bp of the *P. infestans* 18S rRNA, which has 100% identity with the homologous sequence of the 18S rRNA gene from man (*Homo sapiens*), pigs (*Sus scrofa*) and cattle (*Bos taurus*). Human potato consumption in Asia in 2005 was 26 kg, in North America it was 58 kg and in Europe it was 96 kg per person (FAOSTAT). In the light of the high human and animal consumption of potatoes, the rRNA sequences from *Phytophthora infestans* described in WO 2006/047495 as HIGS target genes are unsuitable for consumers on safety grounds.

On the other hand, in WO 2006/047495, plants were produced that carry gene sequences for the cathepsin B gene from *Myzus persicae* and the elicitin gene INF1 from *P. infestans* for RNA interference and thus exhibit resistance to two plant pathogens. The target gene INF1 used therein codes for an elicitor. A resistance based on an elicitor as a pathogenicity factor is a disadvantage because the elicitin gene INF1 is not always necessary for an infection of potatoes by *Phytophthora infestans* (Kamoun et al. 1998).

BRIEF SUMMARY OF THE INVENTION

The aim of the present invention is thus to provide a transgenic plant of the species *Solanum tuberosum* which is pathogen-resistant to an oomycete of the genus *Phytophthora* and in particular is suitable for consumption.

In accordance with the invention, this aim is accomplished by the fact that a double-stranded first and second DNA are stably integrated into the transgenic plant, wherein the first DNA comprises (a) a nucleotide sequence in accordance with SEQ ID NOS: 1-43, or (b) a fragment of at least 15 successive nucleotides of a nucleotide sequence in accordance with SEQ ID NOS: 1-43, or (c) a nucleotide sequence which is complementary to one of the nucleotide sequences of (a) or (b), or (d) a nucleotide sequence which hybridizes with one of the nucleotide sequences of (a), (b) or (c) under stringent conditions.

Surprisingly, it has been found that a first DNA of this type is particularly suitable for conferring a pathogen resistance in potato plants via a host-induced gene silencing strategy.

The first and the second DNA are integrated in a stable manner into the genome of a transgenic plant of the species *Solanum tuberosum*. Preferably, the DNAs are integrated in a stable manner into a chromosome of the plant. However, they can also be integrated into an extra-chromosomal element. The advantage of stable integration is that the DNA can be passed on to subsequent generations of the transgenic plant.

The double-stranded DNA is composed of a coding and a non-coding strand.

Furthermore, the nucleotide sequence of the coding strand of the second DNA is the reverse complement of the nucleotide sequence of the coding strand of the first DNA.

The term "reverse complement" with respect to a nucleotide sequence in the 5'-3' direction should be understood to mean a nucleotide sequence in the 3'-5' direction wherein, in accordance with the base pairing rules, the bases correspond to the bases of the first DNA and are in a reverse/mirrored sequence. If the nucleotide sequence of the coding strand of the first DNA is atggttc, for example, then the reverse complementary nucleotide sequence of the coding strand of the second DNA is gaaccat. This is also known as sense and corresponding antisense (reverse complementary) orientation of the nucleotide sequences. In particular, the nucleotide sequence of the coding strand of the second DNA can be the reverse complement of the nucleotide sequence of the coding strand of the first DNA over the whole length of the sequence. However, it can also be only partially reverse complementary, i.e. reverse complementary over a limited length. The nucleotide sequence of the coding strand of the second DNA can also be reverse complementary in more than one region, for example in two or three regions of its nucleotide sequence to the nucleotide sequence of the coding strand of the first DNA.

Starting from the completely or partially reverse complementary nucleotide sequences for the coding strand of the first and second DNA, a double-stranded RNA is produced. The double-stranded structure of the RNA arises by the formation of bridging hydrogen bonds between complementary nucleotides. Double-stranded RNA regions may be formed over a single nucleic acid strand which is partially complementary to itself, or over two different, discontinuous complementary nucleic acid strands. The bridging hydrogen bond formation may thus be intramolecular as well as intermolecular. In accordance with the invention, the first DNA comprises a nucleotide sequence in accordance with SEQ ID NOS: 1-43, wherein these sequences are nucleotide sequences from selected target genes from *Phytophthora infestans*. The group formed by these target genes comprises essential genes for primary metabolism as well as for amino acid synthesis, in particular the biosynthesis of aliphatic amino acids (valine, leucine, isoleucine) as well as for glutamate biosynthesis, genes for cell regulation and signal transduction as well as redox regulation, calcium signalling, G-protein signalling, MAP-kinase signalling and transcription factors, as well as genes for translation components, gene with RNA processing functions, genes which code for developmental and differentiation proteins such as, for example, with cell wall formation functions, as well as genes which code for transporters, channelling and membrane proteins. A summary of these target genes from *Phytophthora* which are used for designing the host-induced gene silencing is set out in Table 1.

TABLE 1

| ID | Target gene_ID | Function | Category | identification |
|---|---|---|---|---|
| 1 | PITG_03410 | Acetolactate synthase | Amino acid biosynthesis | A |
| 2 | PITG_00375 | Haustorium-specific membrane protein (Pihmp1) | Development/differentiation | D |
| 3 | PITG_13490 | Urokanase | Glutamate biosynthesis | C |
| 4 | PITG_00146 | Glucose-6-P-dehydrogenase | Primary metabolism | C |
| 5 | PITG_00561 | Ubiquinone-biosynthesis protein COQ9 | Primary metabolism | B |
| 6 | PITG_06732 | Acyl-CoA-dehydrogenase | Primary metabolism | B |
| 7 | PITG_07405 | Pyruvate kinase | Primary metabolism | B |
| 8 | PITG_12228 | NADH-cytochrome B5 reductase | Primary metabolism | B |
| 9 | PITG_15476 | Malate dehydrogenase | Primary metabolism | B |
| 10 | PITG_18076 | Phosphoglycerate mutase | Primary metabolism | B |
| 11 | PITG_19736 | Alcohol dehydrogenase | Primary metabolism | B |
| 12 | PITG_20129/ | Acyl-CoA-dehydrogenase | Primary metabolism | B |

TABLE 1-continued

| ID | Target gene_ID | Function | Category | identification |
|---|---|---|---|---|
| 13 | PITG_00221 | Tryptophan synthase | Amino acid biosynthesis | A |
| 14 | PITG_05318 | N-(5'-phosphoribosyl)anthranilate-isomerase | Amino acid biosynthesis | C |
| 15 | PITG_13139 | Threonine synthase | Amino acid biosynthesis | C |
| 16 | PITG_00578 | Imidazolone propionase | Glutamate biosynthesis | C |
| 17 | PITG_15100 | Histidine ammonium lyase | Glutamate biosynthesis | A |
| 18 | PITG_11044 | Protein phosphatase | Signal transduction | B |
| 19 | PITG_21987 | Protein phosphatase 2C | Signal transduction | B |
| 20 | PITG_01957 | Calcineurin-like catalytic subunit A | Calcium signalling | C |
| 21 | PITG_02011 | Calcineurin-subunit B | Calcium signalling | C |
| 22 | PITG_16326 | Calcineurin-like catalytic subunit A | Calcium signalling | C |
| 23 | PITG_00708 | Thioredoxin | Redox regulation | C |
| 24 | PITG_00715 | Thioredoxin | Redox regulation | C |
| 25 | PITG_00716 | Thioredoxin | Redox regulation | C |
| 26 | PITG_09348 | Glutaredoxin | Redox regulation | C |
| 27 | PITG_08393 | PsGPR11 G-protein coupled receptor | G-Protein signalling | D |
| 28 | PITG_10447 | SAPK homologue | MAP Kinase signalling | D |
| 29 | PITG_06748 | Myb-like DNA-binding protein | Transcription factor | A |
| 30 | PITG_19177 | C2H2-transcription factor (PsCZF1-homologue) | Transcription factor | D |
| 31 | PITG_06873 | Aspartyl-tRNA-synthetase | Translation | B |
| 32 | PITG_09442 | 40S Ribosomal protein S21 | Translation | B |
| 33 | PITG_16015 | Ribonuclease | RNA-processing | B |
| 34 | PITG_09306 | PnMas2-homologue | Development/differentiation | D |
| 35 | PITG_03335 | Callose synthase (Fks1/2-homologue) | Cell wall formation | D |
| 36 | PITG_05079 | Glycosyl transferase (Fks1/2-Homologue) | Cell wall formation | D |
| 37 | PITG_18356 | Beta-glucane synthesis-associated protein (KRE6-homologue) | Cell wall formation | D |
| 38 | PITG_09193 | Aquaporin | Channel | B |
| 39 | PITG_00562 | Mitochondrial tricarboxylate carrier | Transporter | B |
| 40 | PITG_08314 | ABC superfamily protein | Transporter | B |
| 41 | PITG_12289 | ATPase H- or Na-translocating F-type | Transporter | B |
| 42 | PITG_12999 | MFS superfamily transporter | Transporter | B |
| 43 | PITG_16478 | Acyl-CoA-dehydrogenase | Primary metabolism | B |

DETAILED DESCRIPTION OF THE INVENTION

The term “gene silencing” or silencing describes processes for switching genes off. Silencing can, for example, be transcriptional or post-transcriptional. Gene silencing also includes antisense technology, RNAi, or dsRNA.

The expression of a nucleotide sequence of a target gene in *Phytophthora infestans* is selectively inhibited by gene silencing. A target nucleotide sequence can in this case also be a non-processed RNA molecule, an mRNA or a ribosomal RNA sequence.

The target genes were identified by (i) publically available expression studies such as microarray data regarding oomycete differentiation or infection processes, for example, and publically available data on the investigation of metabolic processes during oomycete differentiation or infection (Grenville-Briggs et al. 2005, Judelson et al. 2009a, Judelson et al. 2009b) (A), (ii) comparative bioinformatic studies coupled with pedantic analysis (BioMax Bioinformatic Framework) (B), (iii) analyses of metabolic pathways coupled with pedantic analysis (C) as well as (iv) evaluations of publically available data regarding the characterization of homologous genes in eukaryotic organisms (Roemer et al. 1994, Inoue et al. 1995, Mazur et al. 1995, Lesage et al. 2004, Avrova et al. 2008, Wang et al. 2009, Li et al. 2010, Wang et al. 2010) (D).

When selecting the target genes, care was taken that the nucleotide sequence of these genes was specific for *P. infestans* in order to exclude unwanted silencing of plant and human genes. To this end, the selected target genes were compared as regards their proteins (BlastX) with the proteome of *Solanum tuberosum* and *Solanum lycopersicum*. At the same time, the target gene sequences were compared as regards their nucleotides (BlastN) with the genome of *Solanum tuberosum, Solanum lycopersicum* and a general BlastN (criteria: BlastN; database: human genomic+transcript; optimize for: somewhat similar sequences (blastn)). Target genes were considered to be highly suitable when they exhibited no nucleotide homologies with *Solanum tuberosum* and *Solanum lycopersicum* and no or only partial homologies in general BlastN in only short sequence regions (<17 nts), so that an interaction with endogenous plant nucleotide sequences was inhibited or did not occur.

In accordance with the invention, the nucleotide sequences used may have different lengths. Thus, the nucleotide sequences of one of SEQ ID NOS: 1-43 may, for example, have a length of between 501 and 735 nucleotides.

The nucleotide sequences used may also be one or more fragments of one or more nucleotide sequences of SEQ ID NOS: 1-43. In this regard, the fragments comprise at least 15, 16, 17, 18, 19, 20, 21, 22, 23, 24, 25, 30, 40, 50, 60, 70, 80, 90, 100, 150, 200, 250, 300, 350, 400, 450, 500, 550, 600, 650, 700, 750, 800, 850, 900, 950, 1000, 1100, 1200 or 1300, 1400, 1500, 1600, 1700, 1800, 1900, 2000, 2100, 2200, 2300, 2400 or 2500 successive nucleotides of one or more of the nucleotide sequences of SEQ ID NOS: 1-43. A particularly suitable fragment is a fragment of the nucleotide sequence of SEQ ID NO: 1 with 290 nucleotides.

In a preferred embodiment of the invention, combinations of two, three, four, five, six, seven, eight, nine, ten or more fragments of the same nucleotide sequence as that of SEQ ID NO: 1 or different nucleotide sequences such as those of SEQ ID NOS: 1, 2, 3, 4, 5, 6, 7, 8, 9, 10, 1, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 or 43 are used. A preferred combination comprises fragments of the nucleotide sequences of SEQ ID NOS: 4, 23, 27 and 28, the genes of which are involved with signal transduction. A further preferred combination comprises fragments of nucleotide sequences of SEQ ID NOS: 3, 16 and 17; these are genes for glutamate biosynthesis from *P. infestans*. Further advantageous combinations comprise nucleotide sequences or fragments of nucleotide sequences from genes for cell wall formation (SEQ ID NOS: 25, 36, 37), calcium signalling (SEQ ID NOS: 20, 21, 22), primary metabolism genes (SEQ ID NOS: 5, 6, 7), redox regulation genes (SEQ ID NOS: 24, 25, 26), or comprise several nucleotide sequences or fragments of nucleotide sequences from transporter genes in accordance with SEQ ID NOS: 39, 40, 41, 42. Further preferred combinations comprise nucleotide sequences or fragments of nucleotide sequences of different target gene groups such as, for example, genes for G-protein signalling, MAP kinase signalling, primary metabolism and redox regulation (SEQ ID NOS: 27, 28, 4, 23).

Combining several target genes means that the possibility that the resistance of the transgenic plant could be disrupted by a natural mutation in the oomycete is avoided.

The double-stranded first DNA introduced into the potato plant of the invention may comprise a nucleotide sequence which hybridizes under stringent conditions with one of the following nucleotide sequences: (a) a nucleotide sequence in accordance with SEQ ID NOS: 1-43, or (b) a fragment of at least 15 successive nucleotides of a nucleotide sequence in accordance with SEQ ID NOS: 1-43, or (c) a nucleotide sequence which is complementary to one of the nucleotide sequences of (a) or (b), or (c). Examples of stringent conditions are: hybridizing in 4×SSC at 65° C. and then washing several times in 0.1×SSC at 65° C. for approximately 1 hour in total. The term "stringent hybridization conditions" as used here can also mean: hybridization at 68° C. in 0.25 M sodium phosphate, pH 7.2 7% SDS, 1 mM EDTA and 1% BSA for 16 hours and subsequently washing twice with 2×SSC and 0.1% SDS at 68° C.

The present invention also in particular encompasses such fragments of nucleotide sequences which have a few, for example 1 or 2 nucleotides, which are not complementary to the target gene sequence from *Phytophthora infestans*. Sequence variations which, for example, occur in oomycetes, which are based on a genetic mutation, for example by addition, deletion or substitution or a polymorphism in a *Phytophthora infestans* strain and which result in wrong pairing over a region of 1, 2 or more nucleotides, can be tolerated as long as the RNA formed by the transgenic potato plant can still interfere with the target gene RNA formed by the oomycete.

In accordance with the invention, the transgenic plant of the species *Solanum tuberosum* confers a pathogen resistance to an oomycete of the genus *Phytophthora*. To determine the resistance, the transgenic potato plant is compared with a control plant which ideally has the identical genotype to the transgenic plant and has been grown under identical conditions, but which does not contain the DNA which has been introduced into the transgenic plant. The resistance can be determined using an optical score, wherein scores of 0 (not susceptible) to 100 (very susceptible) are awarded. Preferably, the transgenic plants of the invention confer a resistance which, compared with a control plant, results in a reduced propagation of infection over the plant surface of at least 10, 15, 20, 25, 30, 35, 40, 45, 50, 55, 60, 65, 70, 75, 80, 85, 90, 95, 100 percent (see the conditions under "measuring the resistance in transgenic potato plants under outdoor conditions).

The genus *Phytophthora* comprises various species, for example the species *alni, cactorum, capsici, cinnamomi, citrophthora, clandestina, fragariae, hedraiandra, idaei, infestans, ipomoeae, iranica, kernoviae, mirabilis, megakarya, nicotianae, palmivora, parasitica, phaseoli, ramorum, pseuodotsugae, quercina, sojae* or *tentaculata*.

In a preferred embodiment of the invention, the transgenic potato plant exhibits a resistance to *Phytophthora infestans*.

Already the inhibition of the biosynthesis of the aliphatic amino acids valine, leucine and isoleucine by a construct directed against acetolactate synthase from *P. infestans* results in a substantial reduction in blight infestation and a drastic increase in leaf resistance under laboratory and field conditions. By combining several target genes such as, for example, genes from G protein signalling, MAP kinase signalling, primary metabolism, amino acid biosynthesis and redox regulation in one construct, the resistance effect can be increased still further, since the pathogen is inhibited by the multiple action of the combination construct on the use of alternative signalling and metabolic pathways.

Surprisingly, the defensive power of the potato plants of the invention against isolates of *P. infestans* of varying aggressivity is changed in a manner such that a resistance is obtained which protects the plants efficiently and permanently against this most important of pathogens.

It was also surprisingly discovered that the resistance has no great energetic disadvantages or negative changes in the agronomic properties of the potato plant. The cultivation trials under near-field conditions did not have any deleterious effects on the quality of the plants. Careful selection of the target genes of *P. infestans* which excludes any homology extending over 17 successive base pairs with genes from non-target organisms (potato, human, pig, cattle) means that there are no restrictions on using the plants as a feed or foodstuff and no restrictions as regards sowing, cultivation, harvesting or processing the crop. The plants can freely be used as agricultural, food or feed plants.

In accordance with a preferred embodiment, the double-stranded RNA is miRNA or siRNA. MiRNA describes small interfering RNA and includes naturally produced miRNAs and synthetic miRNAs which, for example, can be produced by recombinant or chemical synthesis or by processing primary miRNA.

SiRNA describes small interfering RNA and includes naturally produced siRNAs and synthetic siRNAs which, for example, can be produced by recombinant or chemical synthesis or by processing dsRNAs.

The transgenic plant produces dsRNA from the introduced double-stranded DNA which is processed by endogenous RNAi or silencing mechanisms to form siRNAs and miRNAs.

In order to obtain dsRNA, a double-stranded first DNA with a nucleotide sequence in accordance with one of SEQ ID NOS: 1-43 or a fragment thereof in the sense orientation and a double-stranded second DNA in the antisense orientation can be used which are separated by an intron which has no similarity with the target genes in question. As an example, the DNA may be orientated with a nucleotide sequence of SEQ ID NO: 1 against the acetolactate synthase gene from *Phytophthora infestans*. Upon expression in a plant cell, an RNA transcript is formed which, because of the homology between the sense and antisense sequence regions, can coalesce to form a dsRNA. Because the missing base pairs in the region of the intron, the dsRNA forms a hairpin structure. A dsRNA with a hairpin structure can also be prepared by means of one double-stranded DNA with a nucleotide sequence in accordance with one of SEQ ID NOS: 1-43 in the sense orientation and a second in the antisense orientation with a different length. In this respect, the nucleotide sequence in the sense orientation may be about 190 nucleotides longer than the nucleotide sequence in the antisense orientation, or vice versa.

Defined sequence regions for the selected nucleotide sequences of the target genes are amplified by PCR and cloned both in the sense and in the antisense direction into a vector which is suitable for the synthesis of hairpin structures. In this regard, several fragments with sequence regions of different target genes can be cloned into a vector in order to construct a combination hairpin construct. The vectors can be introduced into a plant cell using transformation methods which are known in plant biotechnology. The skilled person will be aware that, for example, a selected nucleotide sequence of a target gene can also be cloned into one vector in the sense orientation and the nucleotide sequence of the target gene can be cloned into a second vector in the antisense orientation and then introduced into a plant cell by co-transformation, for example.

The silencing mechanism arises from dsRNA such as, for example, hairpin RNA structures or gene duplexes. The dsRNA will produce small dsRNAs by means of a dsRNA-specific endonuclease (dicer), which are processed by means of longer nucleotide sequences into small dsRNAs preferably of 21-25 base pairs, a process which is similar for both "stem-loop" (primary miRNA) and also for long complementary dsRNA precursors. Argonaut proteins, as central components of the RNA-induced silencing complexes (RISC), bind and unwind siRNA and miRNA so that the lead strand of the duplex binds specifically by base pairing to the mRNA and leads to its degradation. By means of miRNA, RNAi behaves in a comparatively similar process, with the difference that the miRNA produced also comprises partial regions which are not identical to the target genes.

After infestation of a host plant with *Phytophthora infestans*, an exchange of RNA formed in the plant which is directed against one or more *Phytophthora*-specific target sequences can occur between the host plant and the oomycetes. In the oomycetes, these RNAs can lead to sequence-specific gene silencing of one or more target genes. Proteins and protein complexes such as dicers, RISC (RNA-induced silencing complex) as well as RNA-dependent RNA polymerase (RdRP), can participate in this process.

The siRNA effect is known to be continued in plants when the RdRP synthesises new siRNAs from the degraded mRNA fragments. This secondary or transitive RNAi can reinforce silencing and also result in silencing of different transcripts when they share these highly conserved sequences.

In a preferred embodiment, the first DNA and the second DNA are operatively linked with at least one promoter.

A "promoter" is a non-translated DNA sequence, typically upstream of a coding region which contains the binding site for the RNA polymerase and initiates transcription of the DNA. A promoter contains special elements which function as regulators for gene expression (for example cis-regulatory elements). The term "operatively linked" means that the DNA which comprises the integrated nucleotide sequence is linked to a promoter in a manner such that it allows expression of this nucleotide sequence. The integrated nucleotide sequence may be linked with a terminator signal downstream as a further component.

The promoter can be of plant, animal or microbial origin, or it may be of synthetic origin and can, for example, be selected from one of the following groups of promoters: constitutive, inducible, development-specific, cell type-specific, tissue-specific or organospecific. While constitutive promoters are active under most conditions, inducible promoters exhibit expression as a result of an inducing signal which, for example, may be issued by biotic stressors such as pathogens or abiotic stressors such as cold or dryness or chemicals.

Examples of promoters are the constitutive CaMV 35S promoter (Benfey et al., 1990) as well as the C1 promoter which is active in green tissue (Stahl et al., 2004).

The first and second DNA may also, however, be operatively linked to a double promoter such as, for example, the bidirectionally active TR1' and TR2' promoter (Saito et al., 1991).

Furthermore, the first and the second DNA may each be operatively linked to a promoter.

The use of two promoters, which each flank the 3' end and the 5' end of the nucleic acid molecule, enables expression of the respective individual DNA strand, wherein two complementary RNAs are formed which hybridize and form a dsRNA. In addition, the two promoters can be deployed such that one promoter is directed towards the transcription of a selected nucleotide sequence and the second promoter is directed towards the transcription of a nucleotide sequence which is complementary to the first nucleotide sequence. As long as both nucleotide sequences are transcribed, a dsRNA is formed.

Further, a bidirectional promoter can be deployed which allows the expression of two nucleotide sequences in two directions, wherein one nucleotide sequence is read off in the 3' direction and a second nucleotide sequence is read off in the 5' direction. As long as both nucleotide sequences are complementary to each other, a dsRNA can be formed.

The present invention also concerns parts of a transgenic plant of the species *Solanum tuberosum*.

In the context of this application, the term "parts" of the transgenic plant in particular means seeds, roots, leaves, flowers as well as cells of the plant of the invention. In this regard, the term "cells" should be understood to mean, for example, isolated cells with a cell wall or aggregates thereof, or protoplasts. "Transgenic parts" of the transgenic plant also means those which can be harvested, such as potato tubers, for example.

Furthermore, the present invention concerns a method for the manufacture of a transgenic plant of the species *Solanum tuberosum* which exhibits a resistance against an oomycete of the genus *Phytophthora*.

Suitable methods for the transformation of plant cells are known in plant biotechnology. Each of these methods can be used to insert a selected nucleic acid, preferably in a vector, into a plant cell in order to obtain a transgenic plant in accordance with the present invention. Transformation methods can include direct or indirect methods for transformation and can be used for dicotyledenous plants and primarily also for monocotyledenous plants. Suitable direct transformation methods include PEG-induced DNA uptake, liposome-induced transformation, biolistic methods by means of particle bombardment, electroporation or microinjection. Examples of indirect methods are *agrobacterium*-induced transformation techniques or viral infection by means of viral vectors.

A preferred method which is employed is *agrobacterium*-induced DNA transfer using binary vectors. After transformation of the plant cells, the cells are selected on one or more markers which were transformed in the plant with the DNA of the invention and comprise genes which preferably induce antibiotic resistance such as, for example, the neomycin phosphotransferase II gene NPTII, which induces kanamycin resistance, or the hygromycin phosphotransferase II gene HPTII, which induces hygromycin resistance.

Next, the transformed cells are regenerated into complete plants. After DNA transfer and regeneration, the plants obtained may, for example, be examined by quantitative PCR for the presence of the DNA of the invention. Resistance tests on these plants against *Phytophthora infestans* in vitro and in the greenhouse are next. Routine further phenotypic investigations can be carried out by appropriately trained personnel in the greenhouse or outdoors. These transformed plants under investigation can be cultivated directly.

The method of the invention for the manufacture of a transgenic plant of the species *Solanum tuberosum* which exhibit a resistance against an oomycete of the genus *Phytophthora* comprises the following steps:
(i) producing a transformed first parent plant containing a double-stranded first DNA which is stably integrated into the genome of the parent plant and which comprises (a) a nucleotide sequence in accordance with SEQ ID NOS: 1-43, or (b) a fragment of at least 15 successive nucleotides of a nucleotide sequence in accordance with SEQ ID NOS: 1-43, or (c) a nucleotide sequence which is complementary to one of the nucleotide sequences of (a) or (b), or (d) a nucleotide sequence which hybridizes with one of the nucleotide sequences of (a), (b) or (c) under stringent conditions; (ii) producing a transformed second parent plant containing a double-stranded second DNA which is stably integrated into the genome of the parent plant, wherein the nucleotide sequences for the coding strand of the first and second DNA are partially or completely reverse complementary with respect to each other;
(iii) crossing the first parent plant with the second parent plant;
(iv) selecting a plant in the genome of which a double-stranded first DNA and a double-stranded second DNA has been stably integrated in order to confer a pathogen resistance against an oomycete of the genus *Phytophthora* so that a double-stranded RNA can be produced therefrom.

In accordance with the invention, it is a nucleotide sequence or a fragment of a nucleotide sequence in accordance with SEQ ID NOS: 1-43 from *Phytophthora infestans*.

In a preferred embodiment of the invention, the double-stranded RNA can be miRNA or siRNA.

The invention also concerns a composition for external application to plants.

This composition is prepared for external application to plants. It contains double-stranded RNA, wherein one strand of this RNA corresponds to the transcript of a double-stranded DNA comprising (a) a nucleotide sequence in accordance with SEQ ID NOS: 1-43, or (b) a fragment of at least 15 successive nucleotides of a nucleotide sequence in accordance with SEQ ID NOS: 1-43, or (c) a nucleotide sequence which is complementary to one of the nucleotide sequences of (a) or (b), or (d) a nucleotide sequence which hybridizes with one of the nucleotide sequences of (a), (b) or (c) under stringent conditions.

Double-stranded RNA for the manufacture of the composition in accordance with the invention can be produced in vitro using methods known to the skilled person. As an example, the double-stranded RNA can be synthesized by forming the RNA directly in vitro. The double-stranded RNA can also be synthesized from a double-stranded DNA by formation of an mRNA transcript which then forms a hairpin structure, for example.

The composition in accordance with the invention can be used as a fungicide for a plant or its seed. In this regard, the composition is used to control the growth of the pathogen, for containing the propagation of the pathogen or for the treatment of infected plants. As an example, the composition can be used as a fungicide for spraying in the form of a spray, or other routine ways which are familiar to the skilled person for external application to the plant tissue or by spraying or mixing with the cultivation substrate before or after the plants have sprouted.

In a further application, the composition in accordance with the invention is used as a pre-treatment for seed. In this regard, the composition is initially mixed with a carrier substrate and applied to the seeds in a combination which comprises the double-stranded RNA and the carrier substrate, whereby the carrier substrate has an RNA-stabilizing effect, for example. Thus, the RNA stability and thus its action on the selected target genes of *Phytophthora infestans* can be increased, for example by chemical modifications such as the exchange of ribose for a hexose. Liposomes which encapsulate the RNA molecules can also be used as RNA stabilizers.

Ideally, the plants treated with the composisiton are those of the species *Solanum tuberosum*.

The discussion above regarding the plant of the invention and the method of the invention also apply to this composition.

The present invention will now be described with reference to the figures and sequences:

Detection of sense fragment (370 bp) (primer S334 5'-ATCCCACTATCCTTCGCAAG-3' (SEQ ID NO: 44)×S1259 5'-TTGATATCGCGGAAGGCGAGAGACATCG-3' (SEQ ID NO: 45)) and antisense fragment (450 bp) (S 329 5'-CTAAGGGTTTCTTATATGCTCAAC-3' (SEQ ID NO: 46)×S1259 5'-TTGATATCGCGGAAGGCGAGAGA-CATCG-3' (SEQ ID NO: 45)). Mix: PCR-MasterMix, PCR monitoring. Marker: TrackIt™ 1 Kb DNA Ladder.

FIG. 13A: Detection of siRNAs in transgenic potato plants after transformation with the binary vector pGBTV/EcoRI_kan_PITG_03410. Detection was carried out by hybridization of the Northern Blot with the radioactively labelled probe dsRNA_. Multiple applications of various samples from the lines PR-H4_T007 and T011.

Figure 13:
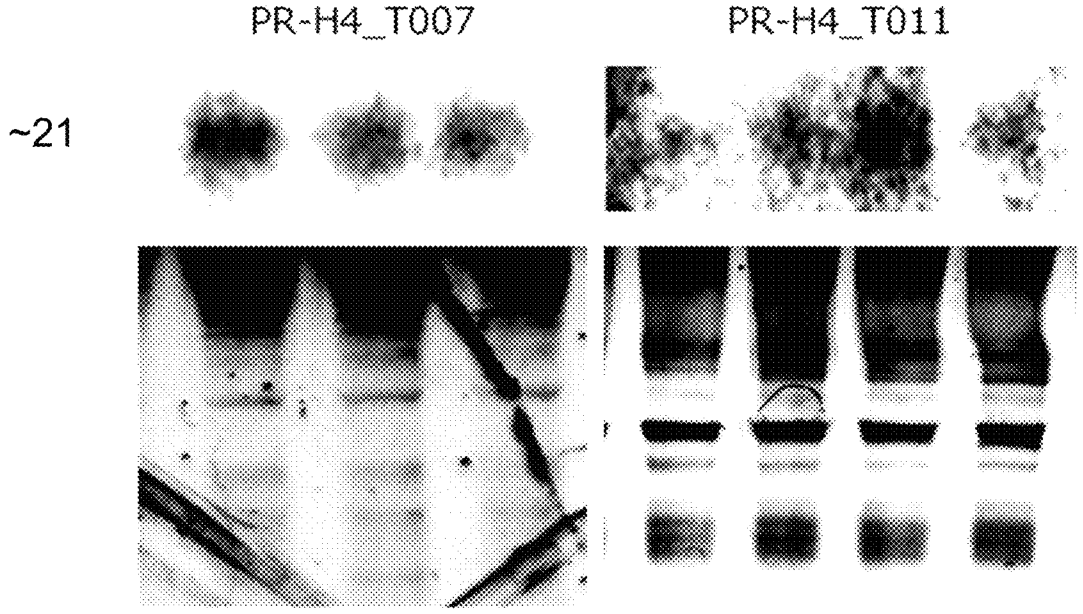
Figure 13:
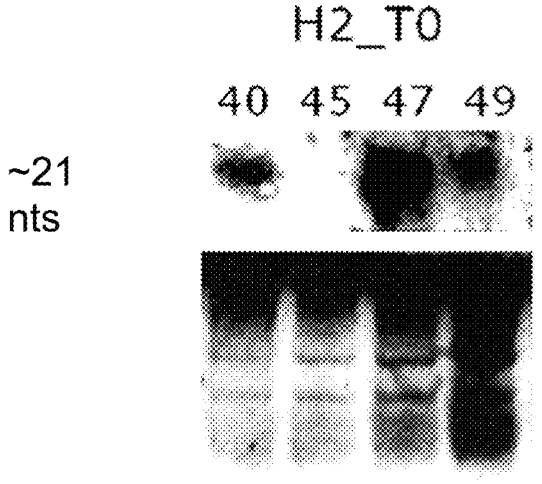

FIG. 13 B: Detection of siRNAs in transgenic potato plants after transformation with the binary vector p95N HIGS_PITG_00375. Detection was carried out by hybridization of the Northern Blot with the radioactively labelled probe dsRNA_PITG_00375. Single application of the samples from the lines PR-H2_T040, T045, T047 and T049.

Figure 14:
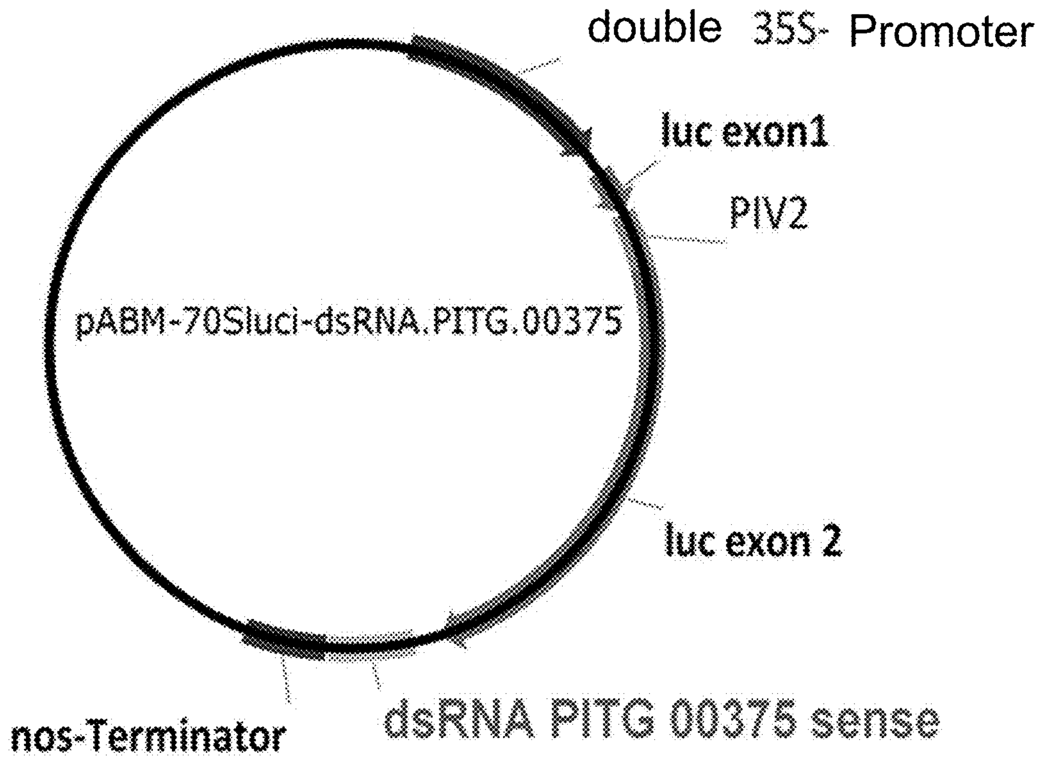
Figure 14:
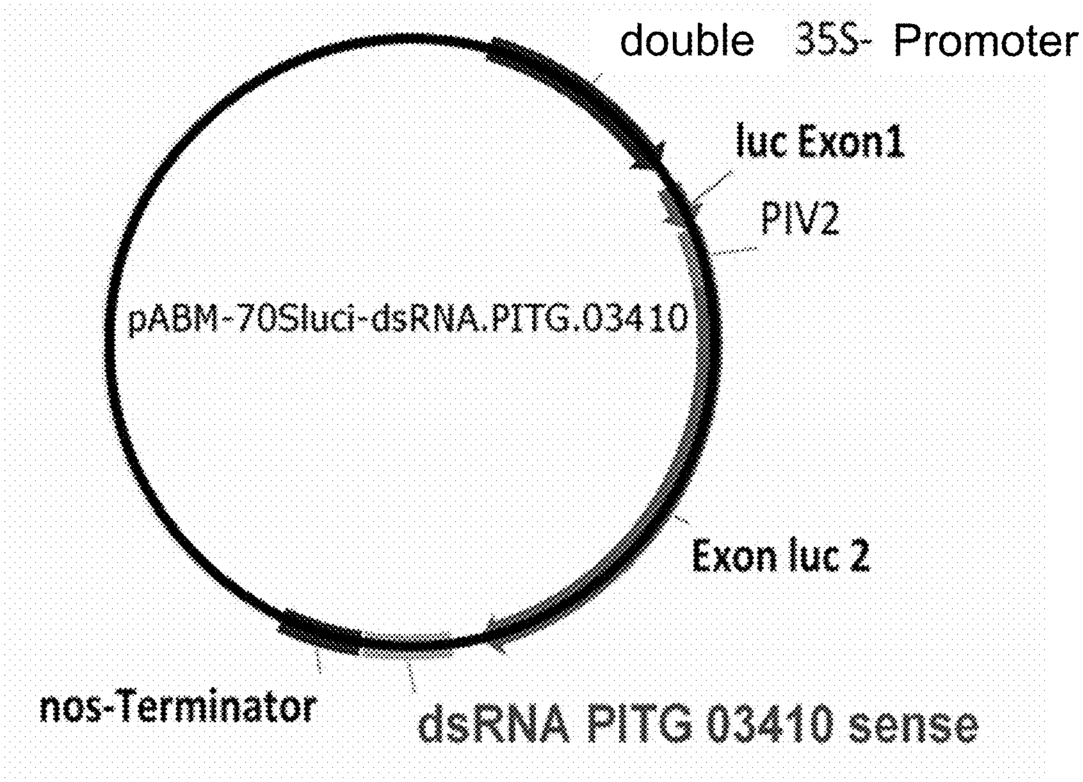

FIG. 14 A: Plasmid pABM-70Sluci_dsRNA.PITG 00375 as an exemplary representation of a vector which contains a fusion construct consisting of the luciferase reporter gene and the test HIGS target fragment PITG 00375. The vector additionally contains a double CaMV 35S promoter, a multiple cloning site, the coding sequence for the luc gene from *Photinus pyralis*, which codes for a luciferase, separated from a modified intron PIV2 from the potato gene St-LS1 (Eckes et al. 1986, Vancanneyt et al. 1990), a further multiple cloning site as well as a Nos terminator from the nopalin synthase gene from *Agrobacterium tumefaciens*.

FIG. 14 B: Plasmid pABM-70Sluci_dsRNA.PITG_03410 as an exemplary representation of a vector which contains a fusion construct consisting of a luciferase reporter gene and the test HIGS target gene fragment PITG_03410.

Figure 15:
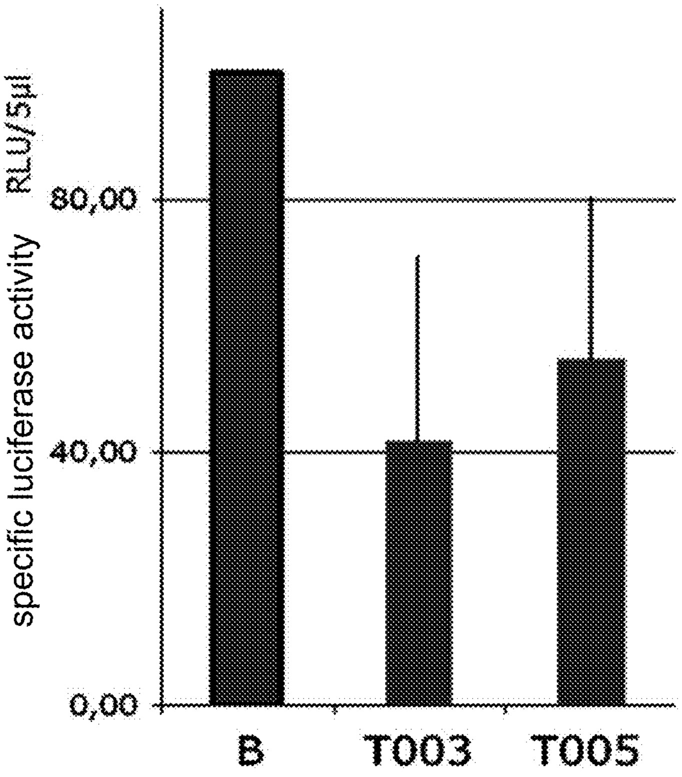
Figure 15:
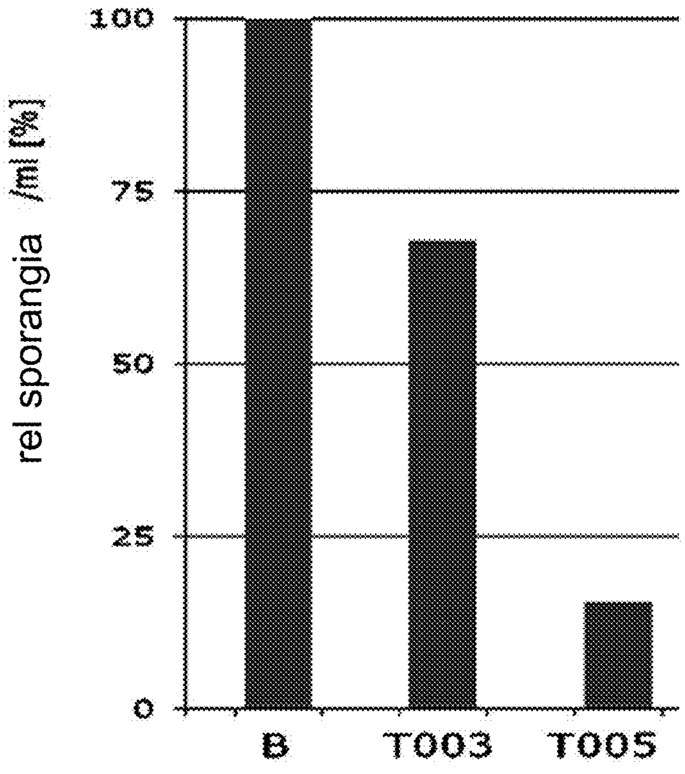

FIG. 15 A: Relative luciferase activity in transgenic potato lines of the genotype Baltica with stable integration of the HIGS_RNAi construct against the PITG_03410 gene from *P. infestans* after bombardment with the vector pABM-70Sluci_dsRNA.PITG_03410. B: Baltica (non-transgenic control), T003, T005 transgenic HIGS potato lines.

FIG. 15 B: Relative sporangia production from *P. infestans* on transgenic HIGS lines. The potato lines of the variety Baltica were transformed with an RNAi construct in order to form dsRNA against the *P. infestans* gene PITG_03410. After infection with *P. infestans* in the detached leaf assay, these lines exhibited a reduced sporangia production compared with the non-transgenic variety Baltica (mean of 4 biological repetitions). B: Baltica (non-transgenic control), T003, T005: transgenic RIGS potato lines.

Figure 16:
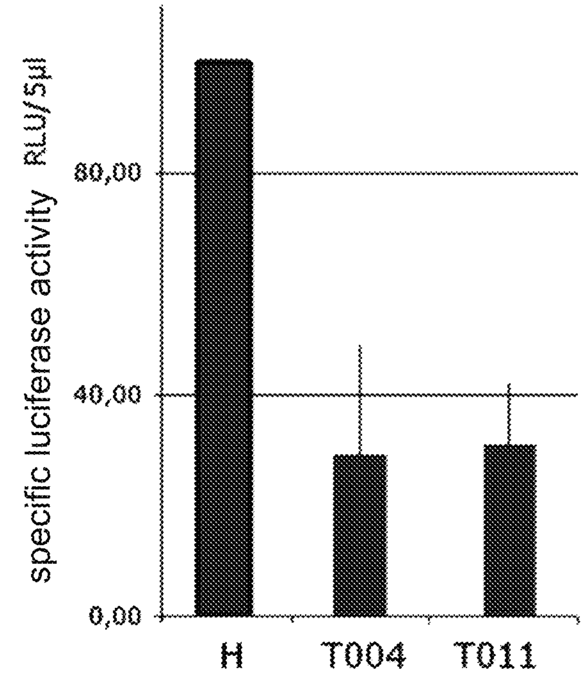
Figure 16:
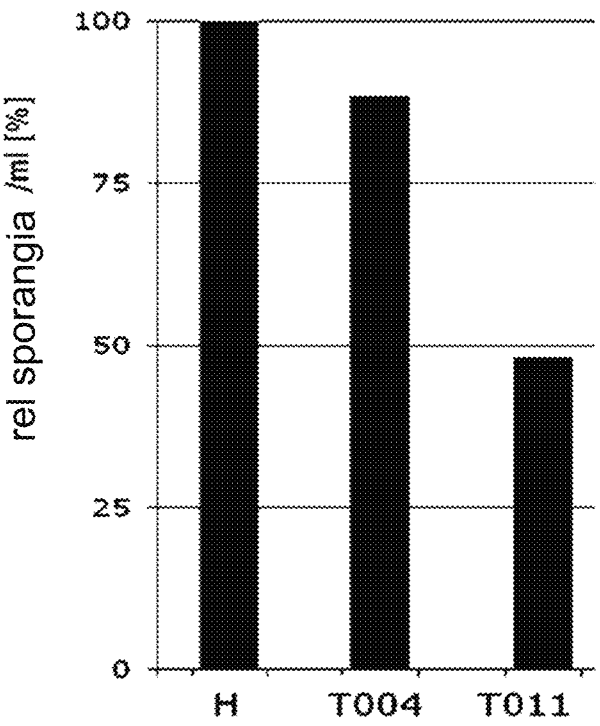

FIG. 16 A: Relative Luciferase activity in transgenic potato lines of the genotype Hermes with stable integration of the HIGS_RNAi construct against the PITG_03410 gene from *P. infestans* after bombardment with the vector pABM-70Sluci_dsRNA.PITG_03410. H: Hermes (non-transgenic control), T004, T011: transgenic HIGS potato lines.

FIG. 16 B: Relative sporangia production of *P. infestans* on transgenic RIGS lines. The potato lines of the variety Hermes were transformed with an RNAi construct in order to form dsRNA against the *P. infestans* gene PITG_03410. After infection with *P. infestans* in the detached leaf assay, these lines exhibited a reduced sporangia production compared with the non-transgenic variety Baltica (mean of 4 biological repetitions). H: Hermes (non-transgenic control), T004, T011: transgenic HIGS potato lines.

Figure 17:
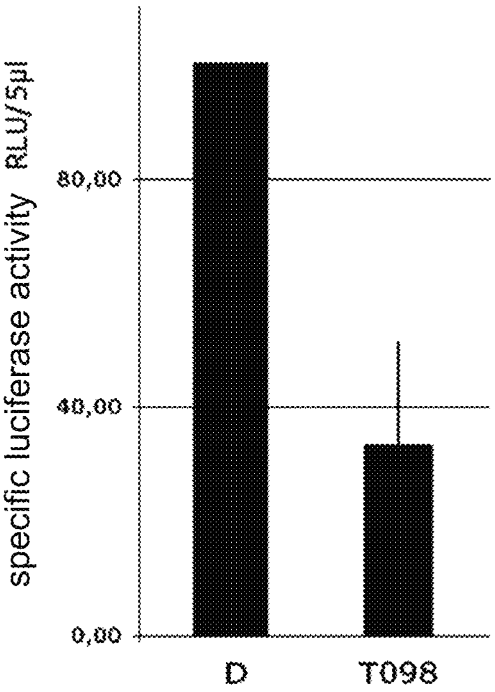
Figure 17:
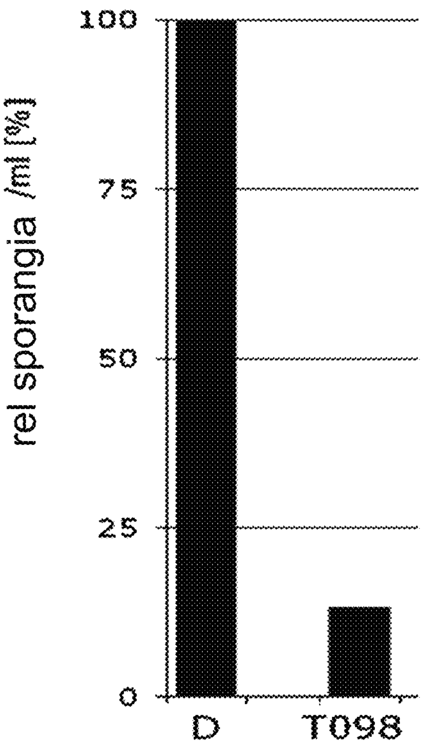

FIG. 17 A: Relative luciferase activity in transgenic potato lines of the genotype Desiree with stable integration of the HIGS_RNAi construct against the PITG_03410 gene from *P. infestans* after bombardment with the vector pABM-70Sluci_dsRNA.PITG_03410. D: Desiree (non-transgenic control), T098: transgenic HIGS potato line.

FIG. 17 B: Relative sporangia production of *P. infestans* on transgenic RIGS lines. The potato lines of the variety Desiree were transformed with an RNAi construct in order to form dsRNA against the *P. infestans* gene PITG_03410. After infection with *P. infestans* in the detached leaf assay, these lines exhibited a reduced sporangia production compared with the non-transgenic variety Baltica (mean of 4 biological repetitions). D: Desiree, (non-transgenic control), T098: transgenic HIGS potato line.

Figure 18:
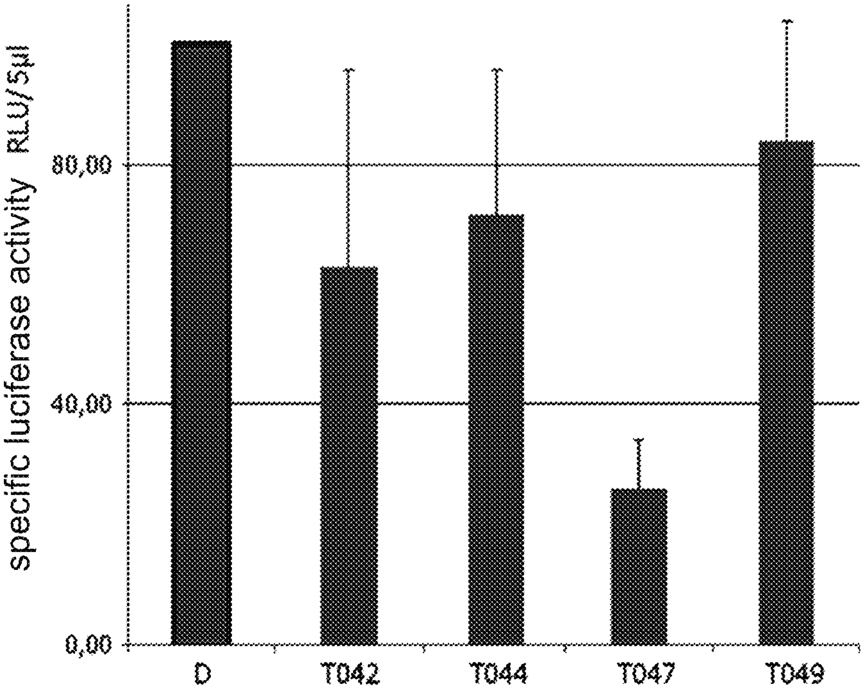
Figure 18:
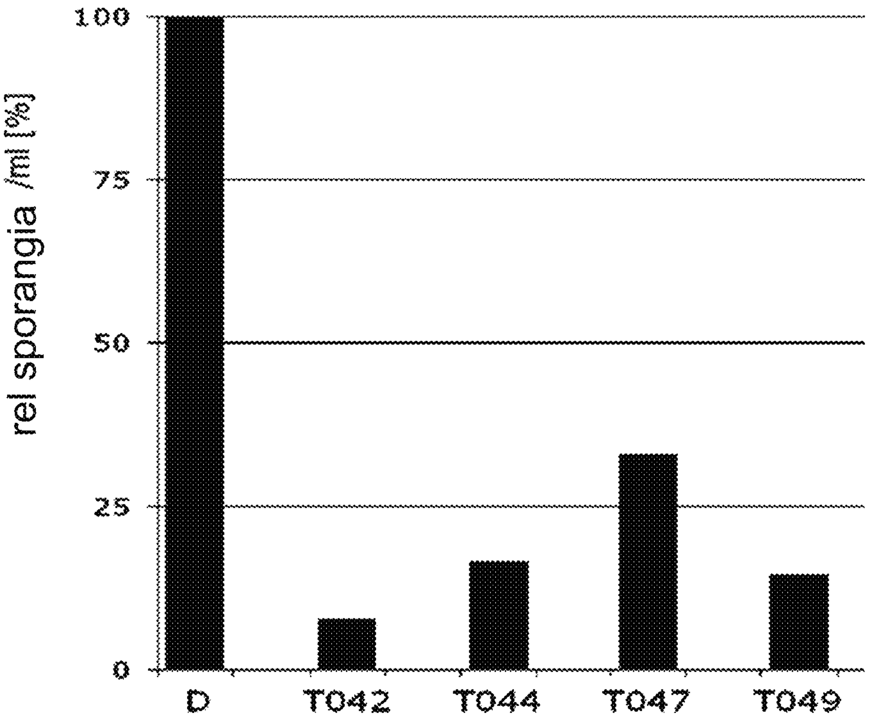

FIG. 18 A: Relative Luciferase activity in transgenic potato lines of the genotype Desiree with stable integration of the HIGS_RNAi construct against the PITG_00375 gene from *P. infestans* after bombardment with the vector pABM-70Sluci_dsRNA.PITG_00375. D: Desiree, (non-transgenic control), T042, T044 T047, T049: transgenic HIGS potato lines.

FIG. 18 B: Relative sporangia production of *P. infestans* on transgenic RIGS lines. The potato lines of the variety Desiree were transformed with a RNAi construct in order to form dsRNA against the *P. infestans* gene PITG_00375. After infection with *P. infestans* in the detached leaf assay, these lines exhibited a reduced sporangia production compared with the non-transgenic variety Baltica (mean of 4 biological repetitions). D: Desiree, (non-transgenic control), T042, T044 T047, T049: transgenic RIGS potato lines.

Figure 19A:
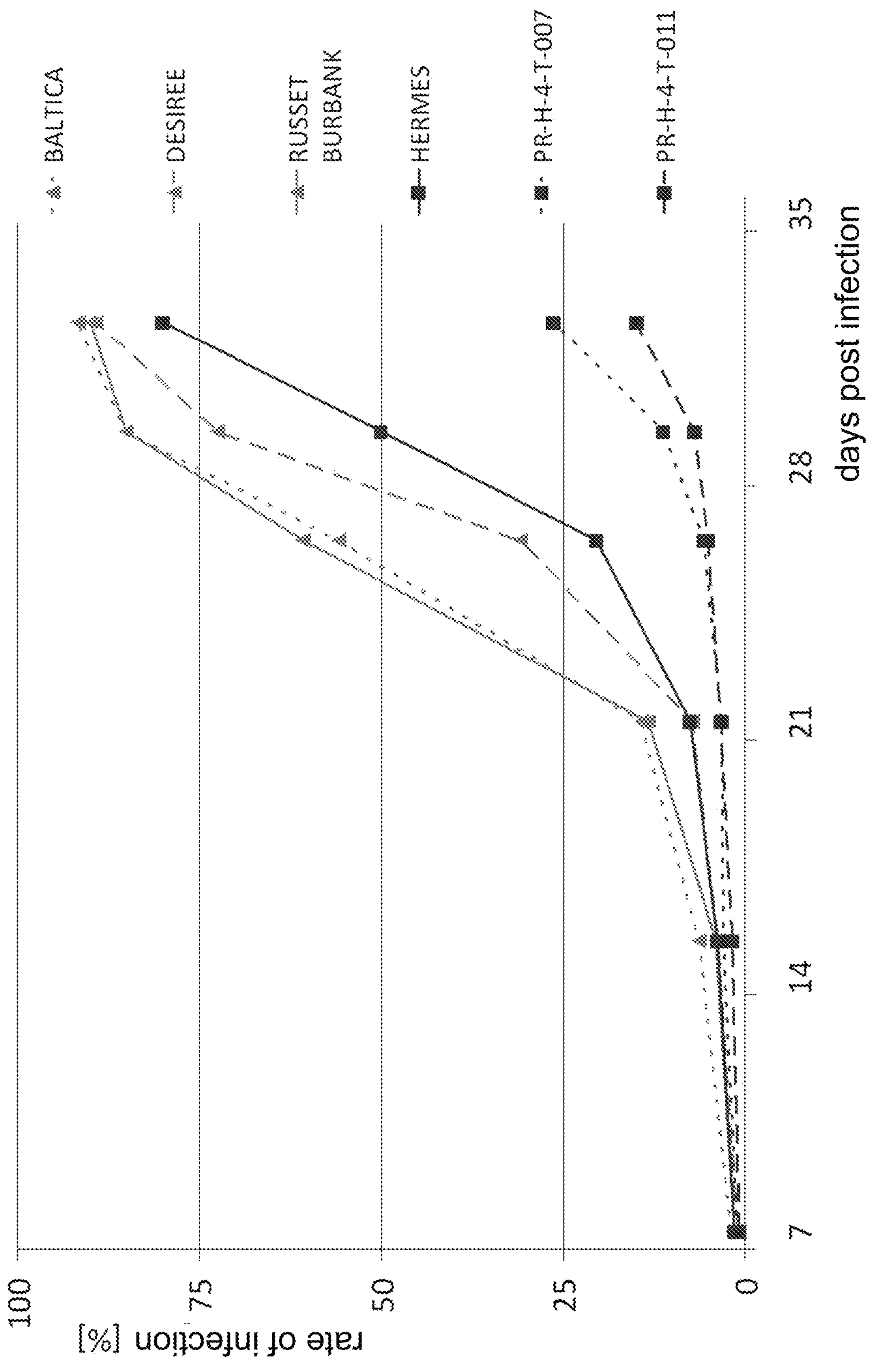
Figure 19:
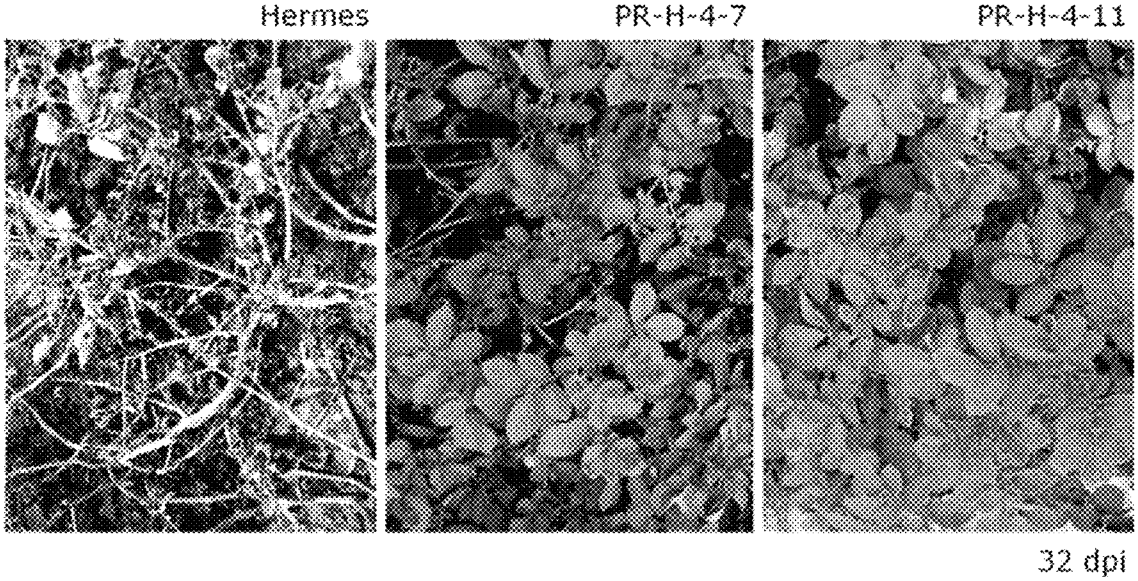

FIG. 19 A: Level of infection in transgenic potato lines of the genotype Hermes with stable integration of the HIGS_RNAi construct against the PITG_03410 gene from *P. infestans* after infection of the plants under outdoor-like conditions with *P. infestans*. Grey lines with triangle: Baltica, Desiree, and Russet Burbank (non-transgenic controls), Black lines with square: plants of the genotype Hermes: solid line: Hermes (non-transgenic control), dashed line: PR-H-4-7 & dotted line: PR-H-4-11: transgenic HIGS potato lines.

FIG. 19 B: Photographic documentation of the degree of infection of the transgenic potato lines PR-H-4-7 and PR-H-4-11 of the genotype Hermes with stable integration of the HIGS_RNAi construct against the PITG_03410 gene from *P. infestans* after infection of the plants under outdoor-like conditions with *P. infestans* compared with the non-transgenic control Hermes. Photographs taken 32 days post-infection.

Figure 20:
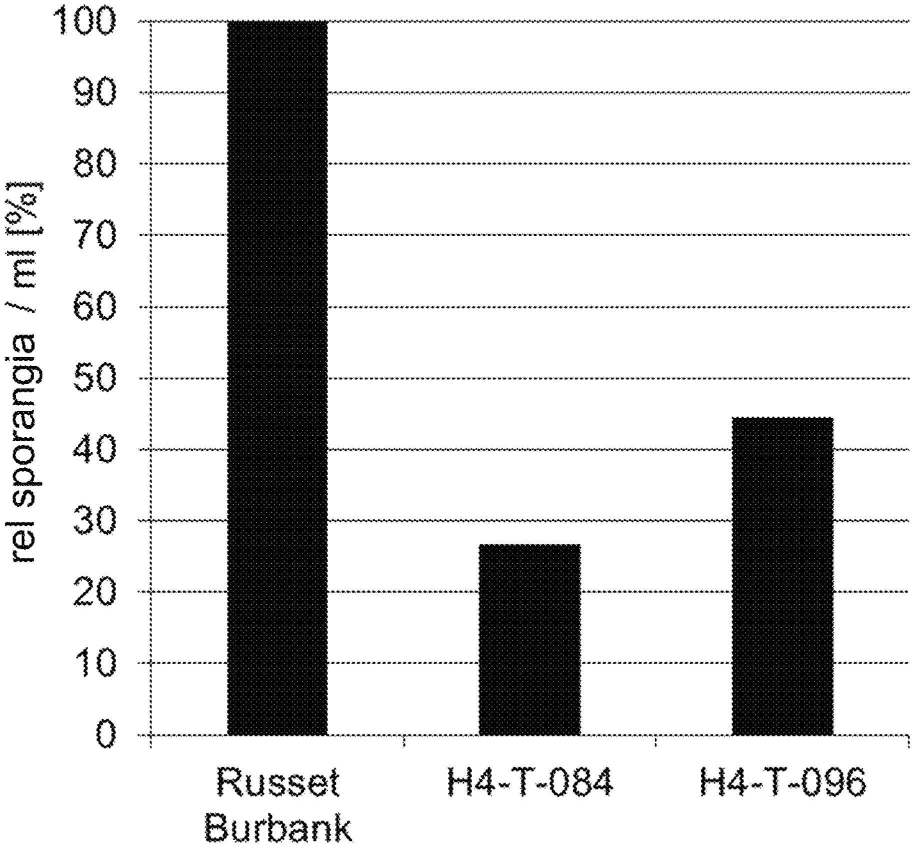

FIG. 20: Relative sporangia production of *P. infestans* on transgenic HIGS lines. The potato lines of the variety Russet Burbank were transformed with a RNAi construct in order to form dsRNA against the *P. infestans* gene PITG_03410. After infection with *P. infestans* in the detached leaf assay, these lines exhibited a reduced sporangia production compared with the non-transgenic variety Russet Burbank (mean of 3 biological repetitions). Russet Burbank (non-transgenic control); H-4-T084, H-4-T096: transgenic HIGS potato lines.

Figure 21:
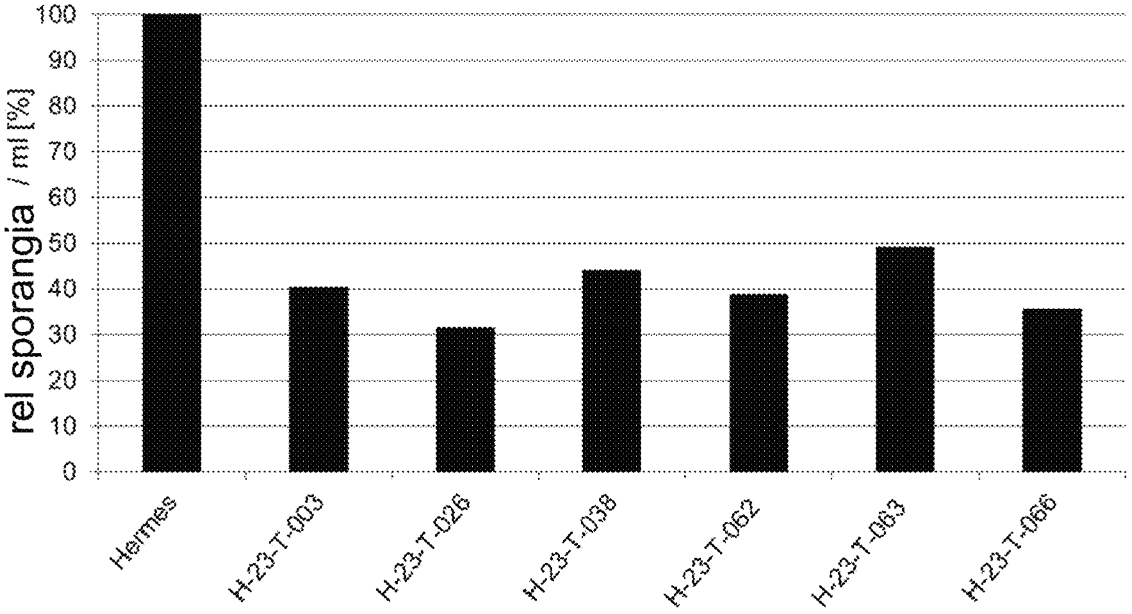

FIG. 21: Relative sporangia production of *P. infestans* on transgenic HIGS lines. The potato lines of the variety Hermes were transformed with a RNAi construct in order to form dsRNA by means of a double promoter construct HIGS_dPRNAi_PITG_03410 against the *P. infestans* gene PITG_03410. After infection with *P. infestans* in the detached leaf assay, these lines exhibited a reduced sporangia production compared with the non-transgenic variety Hermes (mean of 3 biological repetitions). Hermes (non-transgenic control); H-23-T0003, H-23-T026, H-23-T038, H-23-T062, H-23-T063, H-23-T066: transgenic HIGS potato lines.

Figure 22:
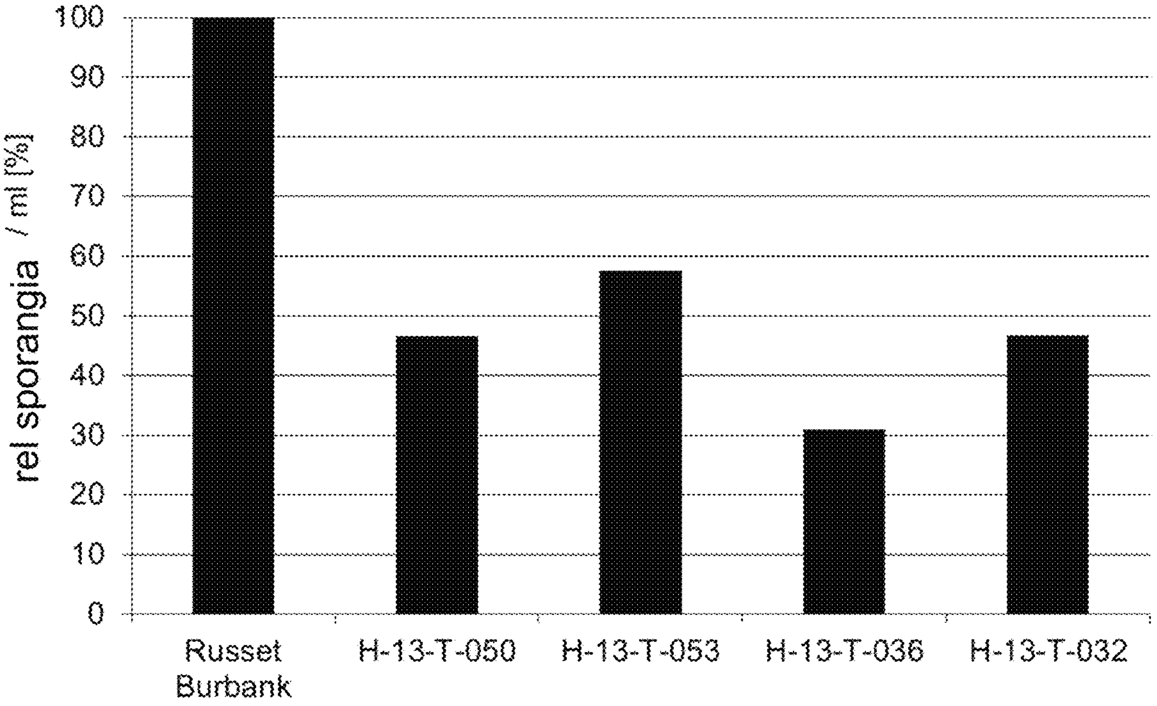

FIG. 22: Relative sporangia production of *P. infestans* on transgenic HIGS lines. The potato lines of the variety Russet Burbank were transformed with an RNAi construct HIGS_CoA in order to form dsRNA against the genes PITG_00146, PITG_08393, PITG_10447 and PITG_00708 from *P. infestans*. After infection with *P. infestans* in the detached leaf assay, these lines exhibited a reduced sporangia production compared with the non-transgenic variety Russet Burbank (mean of 3 biological repetitions). Russet Burbank (non-transgenic control); H-13-T050, H-13-T053, H-13-T036, H-13-T032: transgenic HIGS potato lines.

Figure 23:
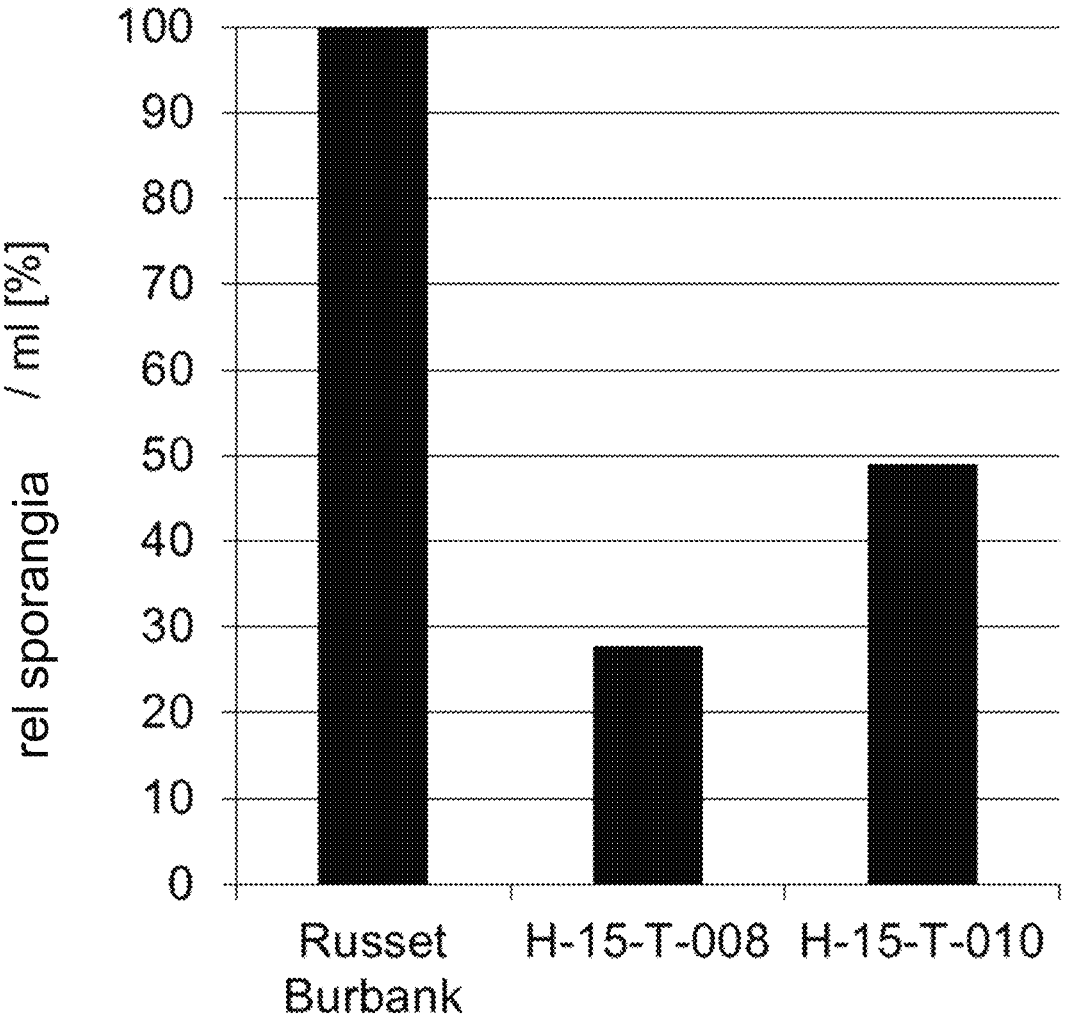

FIG. 23: Relative sporangia production of *P. infestans* on transgenic HIGS lines. The potato lines of the variety Russet Burbank were transformed with a RNAi construct in order to form dsRNA against the *P. infestans* gene PITG_06748. After infection with *P. infestans* in the detached leaf assay, these lines exhibited a reduced sporangia production compared with the non-transgenic variety Russet Burbank (mean of 3 biological repetitions). Russet Burbank (non-transgenic control); H-15-T008, H-15-T010: transgenic HIGS potato lines.

Figure 24:
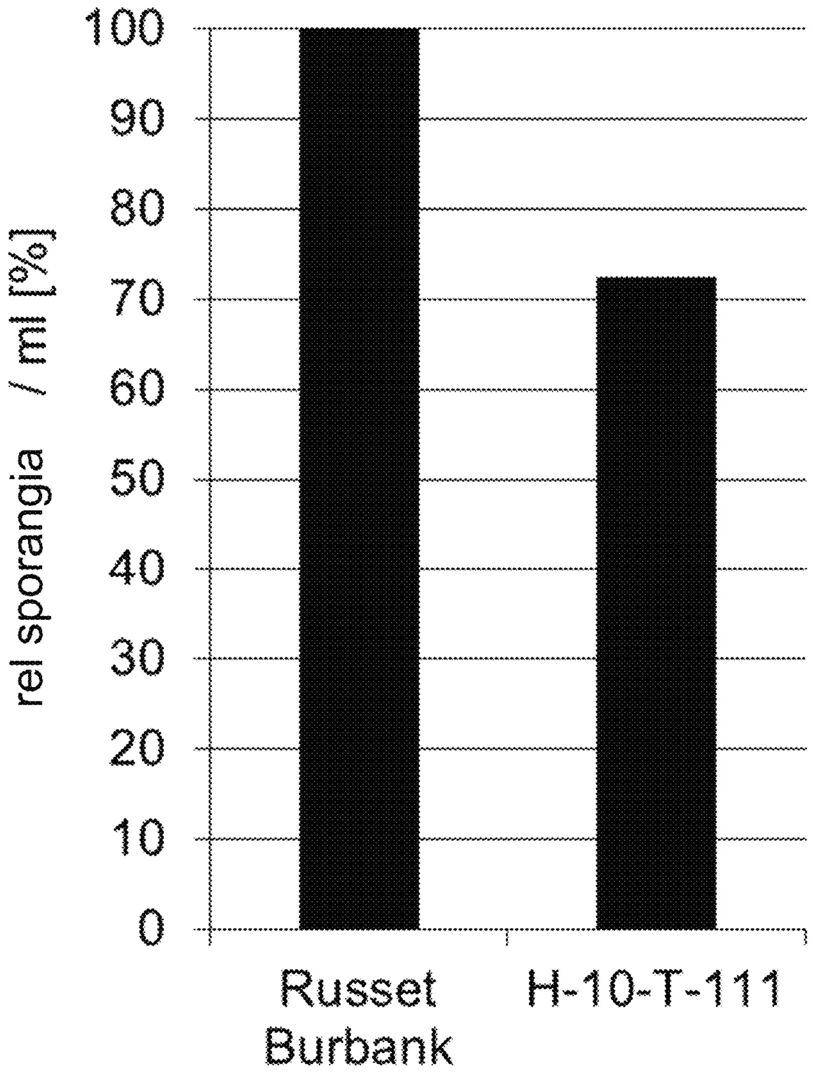

FIG. 24: Relative sporangia production of *P. infestans* on transgenic HIGS line. The potato line of the variety Russet Burbank were transformed with an RNAi construct in order to form dsRNA against the *P. infestans* gene PITG_09306. After infection with *P. infestans* in the detached leaf assay, these lines exhibited a reduced sporangia production compared with the non-transgenic variety Russet Burbank (mean of 3 biological repetitions). Russet Burbank (non-transgenic control); H-10-T111: transgenic HIGS potato line.

Figure 25:
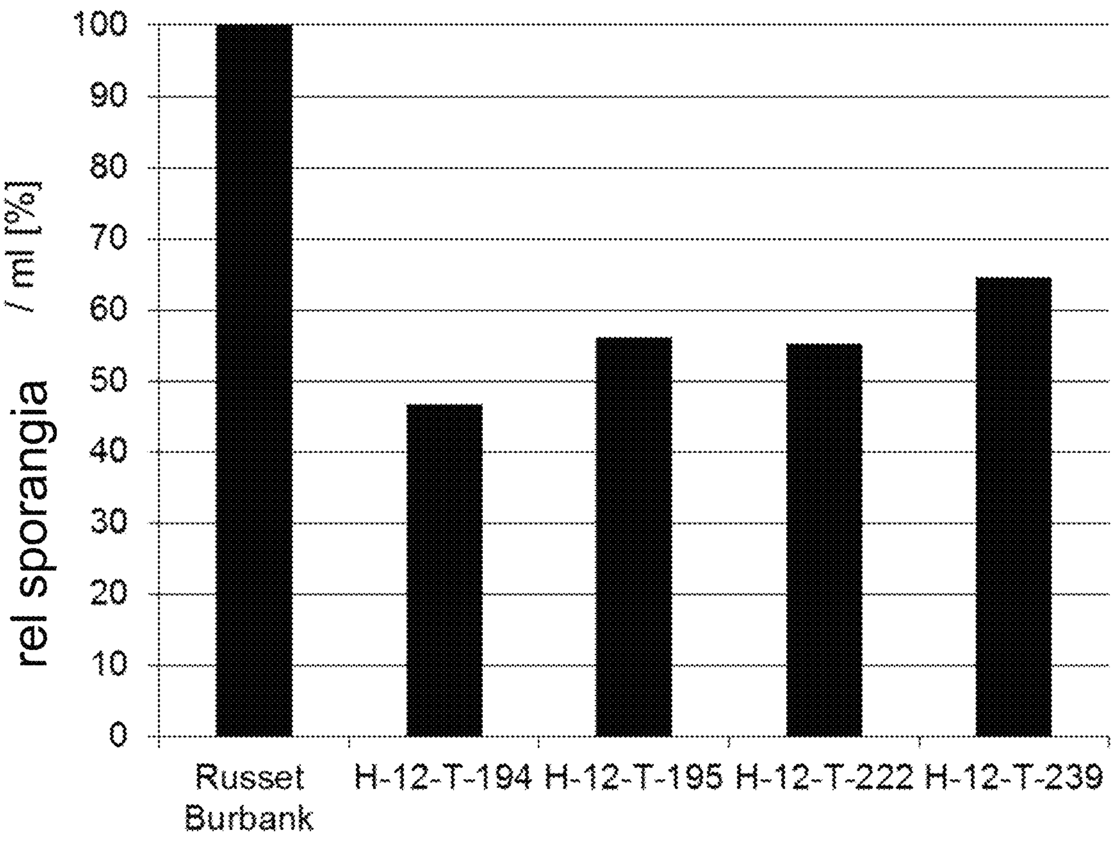

FIG. 25: Relative sporangia production of *P. infestans* on transgenic HIGS lines. The potato lines of the variety Russet Burbank were transformed with an RNAi construct in order to form dsRNA against the *P. infestans* gene PITG_09193. After infection with *P. infestans*, in the detached leaf assay, these lines exhibited a reduced sporangia production compared with the non-transgenic variety Russet Burbank (mean of 3 biological repetitions). Russet Burbank (non-transgenic control); H-12-T194, H-12-T195, H-12-T222, H-12-T239: transgenic HIGS potato lines.

Figure 26:
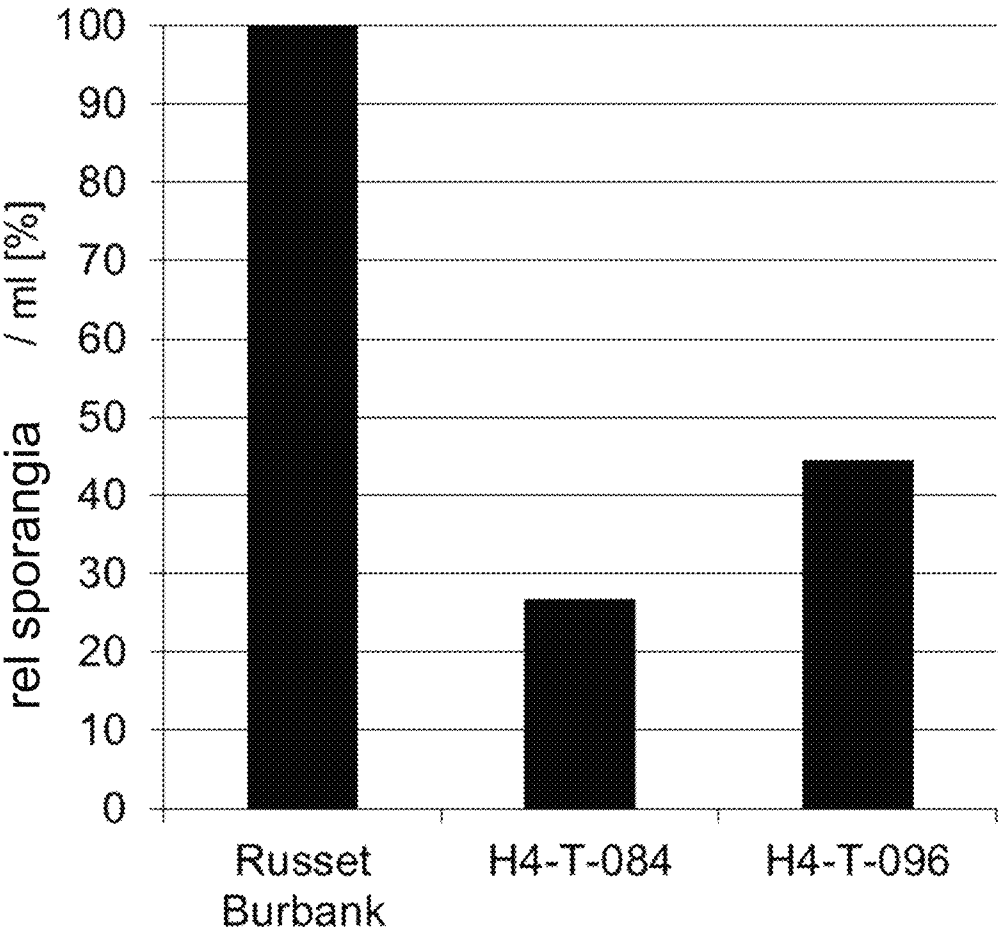

FIG. 26: Relative sporangia production of *P. infestans* on transgenic HIGS lines. The potato lines of the variety Desiree were transformed with an RNAi construct in order to form dsRNA against the *P. infestans* gene PITG_09193. After infection with *P. infestans*, in the detached leaf assay, these lines exhibited a reduced sporangia production compared with the non-transgenic variety Desiree (mean of 3 biological repetitions). Desiree (non-transgenic control); H-12-T187, H-12-T216, H-12-T237, H-12-T245: transgenic HIGS potato lines.

Figure 27:
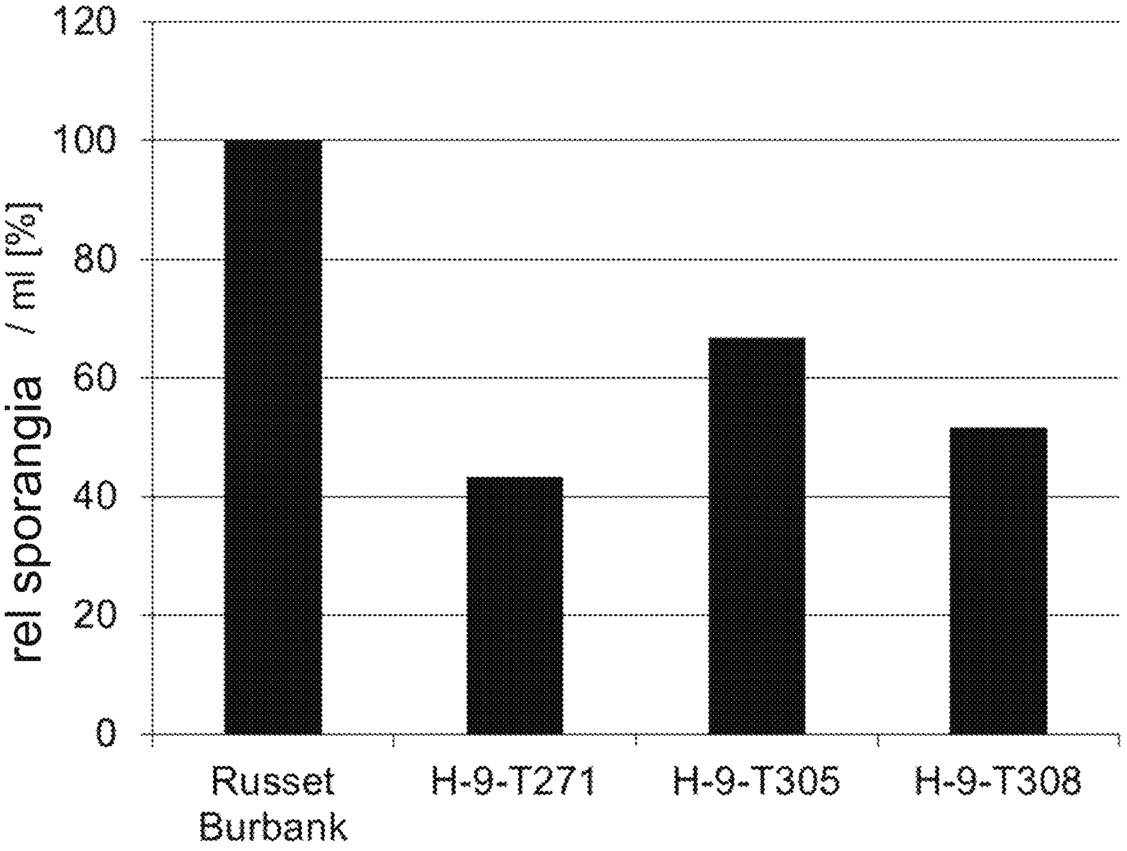

FIG. 27: Relative sporangia production of *P. infestans* on transgenic HIGS lines. The potato lines of the variety Russet Burbank were transformed with an RNAi construct in order to form dsRNA against the *P. infestans* gene PITG_19177. After infection with *P. infestans*, in the detached leaf assay, these lines exhibited a reduced sporangia production compared with the non-transgenic variety Russet Burbank (mean of 3 biological repetitions). Russet Burbank (non-transgenic control); H-9-T271, H-9-T305, H-9-T308: transgenic HIGS potato lines.

Figure 28:
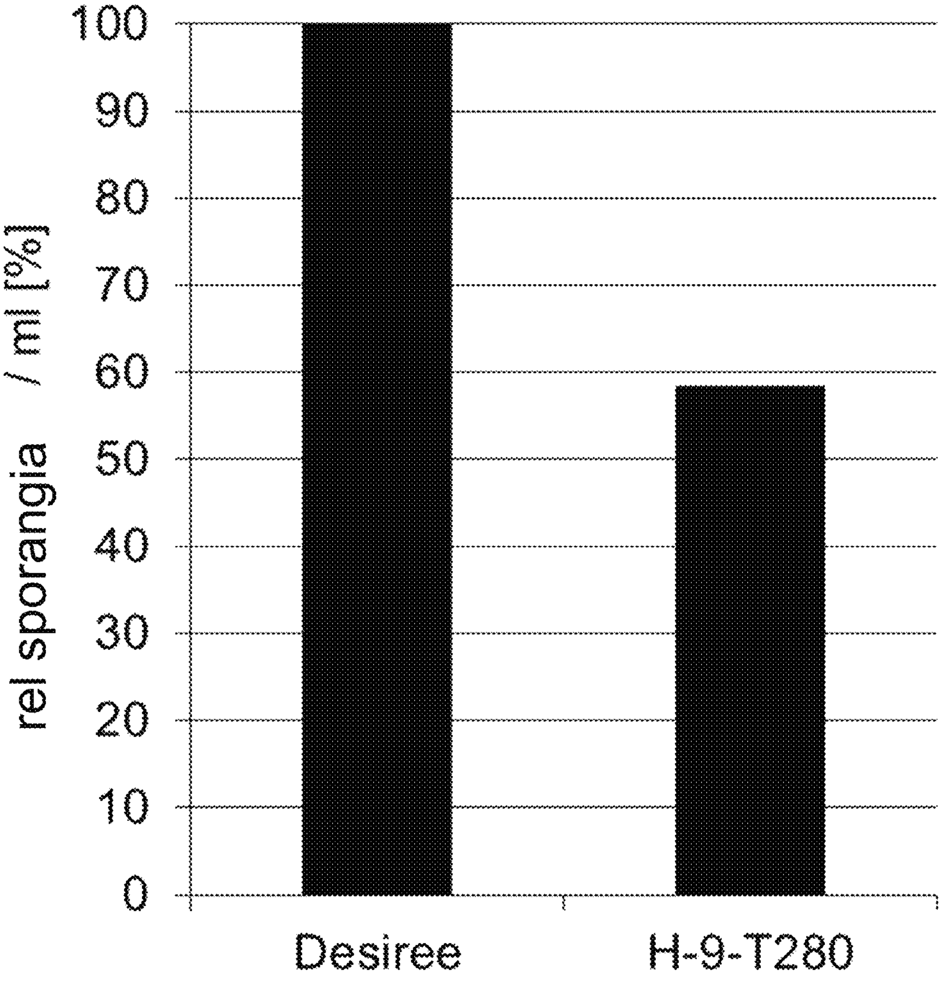

FIG. 28: Relative sporangia production of *P. infestans* on transgenic HIGS line. The potato line of the variety Desirée were transformed with an RNAi construct in order to form dsRNA against the *P. infestans* gene PITG_19177. After infection with *P. infestans* in the detached leaf assay, these lines exhibited a reduced sporangia production compared with the non-transgenic variety Desirée (mean of 3 biological repetitions). Desiree (non-transgenic control); H-9-T280: transgenic HIGS potato line.

Figure 29:
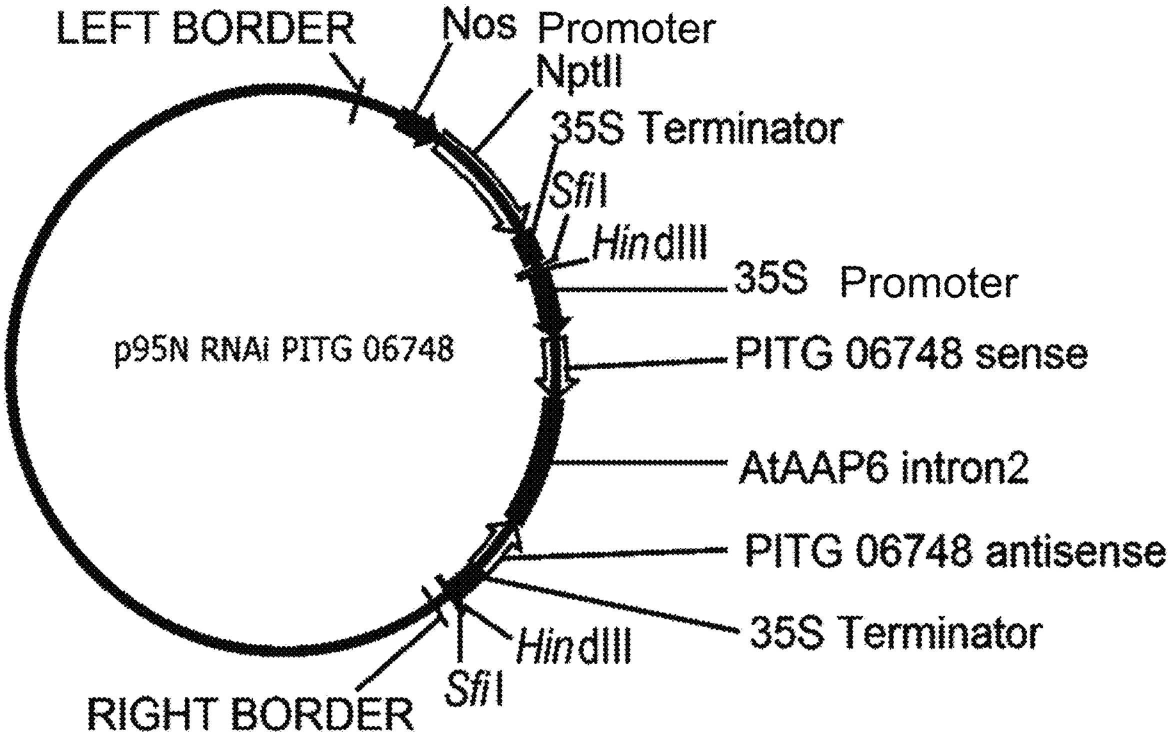

FIG. 29: Plasmid p95N_RNAi PITG_06748 as an exemplary representation of a vector which contains a sense-intron-antisense fragment in order to form dsRNA against a target gene (here PITG_06748). This vector additionally contains a CaMV 35S promoter, a multiple cloning site, an intron from the gene AtAAP6 which codes for an amino acid permease in *Arabidopsis thaliana*, a further multiple cloning site as well as a CaMV 35S terminator.

Figure 30:
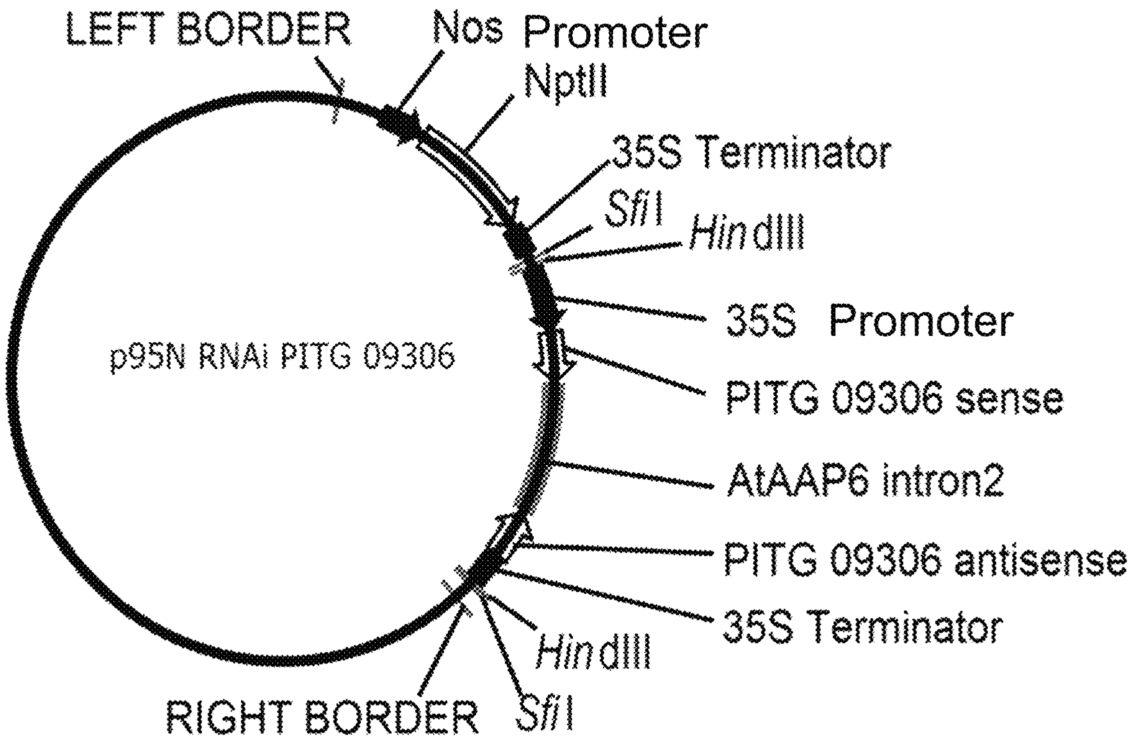

FIG. 30: Plasmid p95N_RNAi_PITG_09306 as an exemplary representation of a vector which contains a sense-intron-antisense fragment in order to form dsRNA against a target gene (here PITG_09306). This vector additionally contains a CaMV 35S promoter, a multiple cloning site, an intron from the gene AtAAP6 which codes for an amino acid permease in *Arabidopsis thaliana*, a further multiple cloning site as well as a CaMV 35S terminator.

Figure 31:
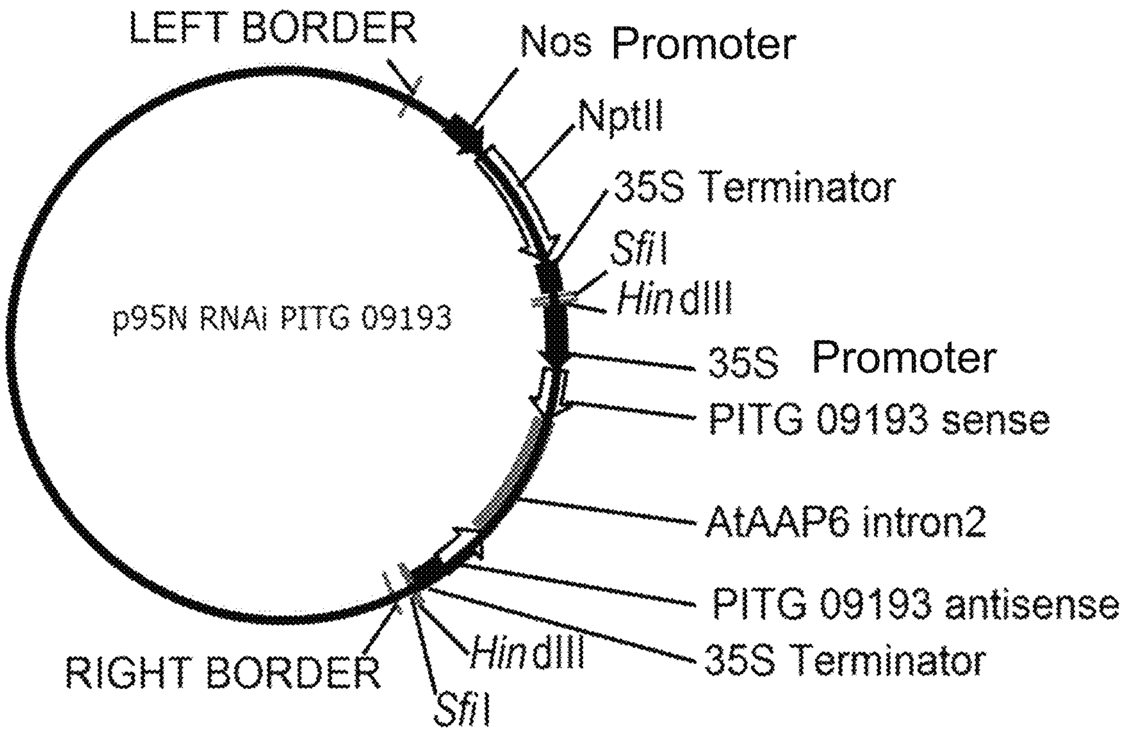

FIG. 31: Plasmid p95N_RNAi_PITG_09193 as an exemplary representation of a vector which contains a sense-intron-antisense fragment in order to form dsRNA against a target gene (here PITG_09193). This vector additionally contains a CaMV 35S promoter, a multiple cloning site, an intron from the gene AtAAP6 which codes for an amino acid permease in *Arabidopsis thaliana*, a further multiple cloning site as well as a CaMV 35S terminator.

Figure 32:
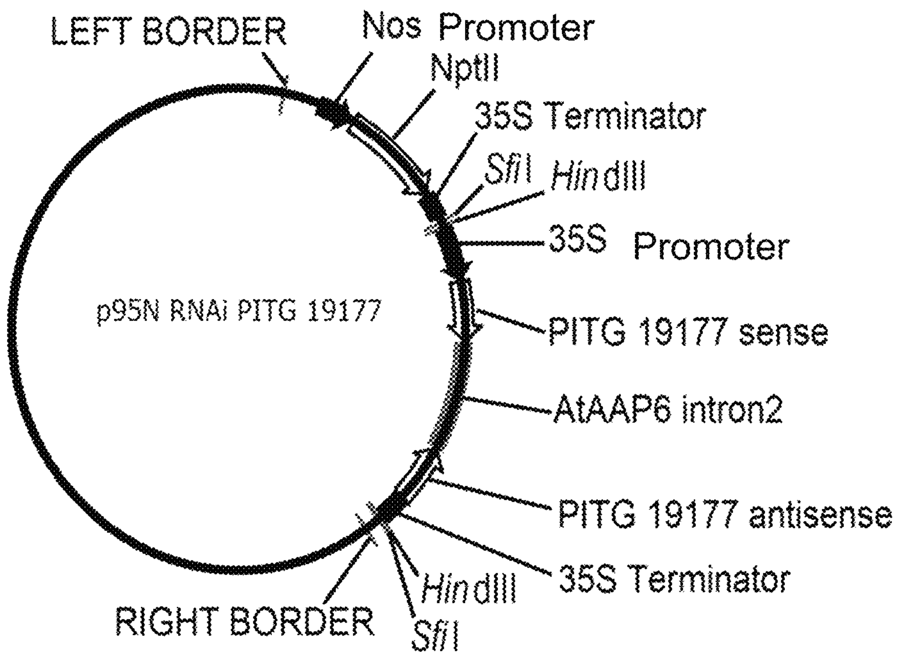

FIG. 32: Plasmid p95N_RNAi_PITG_19177 as an exemplary representation of a vector which contains a sense-intron-antisense fragment in order to form dsRNA against a target gene (here PITG_19177). This vector additionally contains a CaMV 35S promoter, a multiple cloning site, an intron from the gene AtAAP6 which codes for an amino acid permease in *Arabidopsis thaliana*, a further multiple cloning site as well as a CaMV 35S terminator.

EXEMPLARY EMBODIMENTS

Preparation of Constructs

Figure 1:
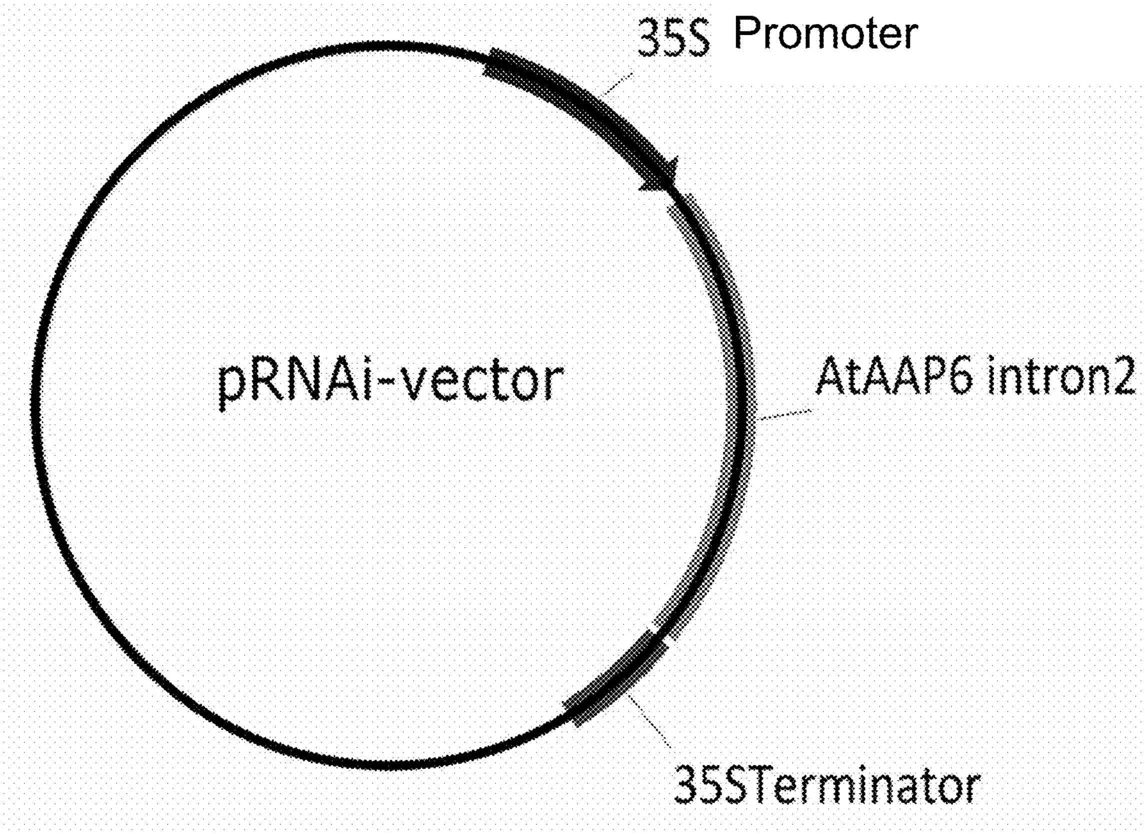
FIG. 1: Plasmid pRNAi as an exemplary representation of a vector which can be used for the formation of hairpin constructs against a target gene. This vector contains a CaMV 35S promoter, a multiple cloning site, an intron from the gene AtAAP6 which codes for an amino acid permease in *Arabidopsis thaliana*, a further multiple cloning site as well as a CaMV 35S terminator.
Figure 2:
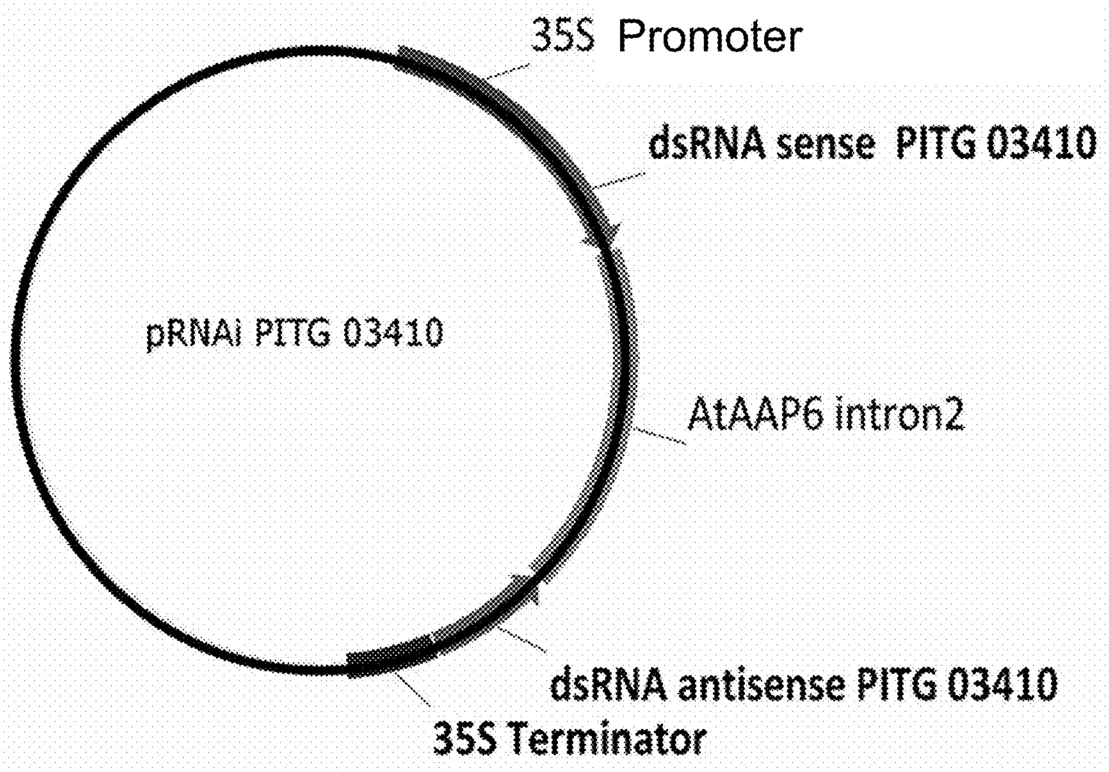
FIG. 2: Plasmid pRNAi_PITG_03410 as an exemplary representation of a vector which contains a sense-intron-antisense fragment for the formation of dsRNA against a target gene (here PITG_03410). This vector additionally contains a CaMV 35S promoter, a multiple cloning site, an intron from the gene AtAAP6 which codes for an amino acid permease in *Arabidopsis thaliana*, a further multiple cloning site as well as a CaMV 35S terminator.
Figure 3:
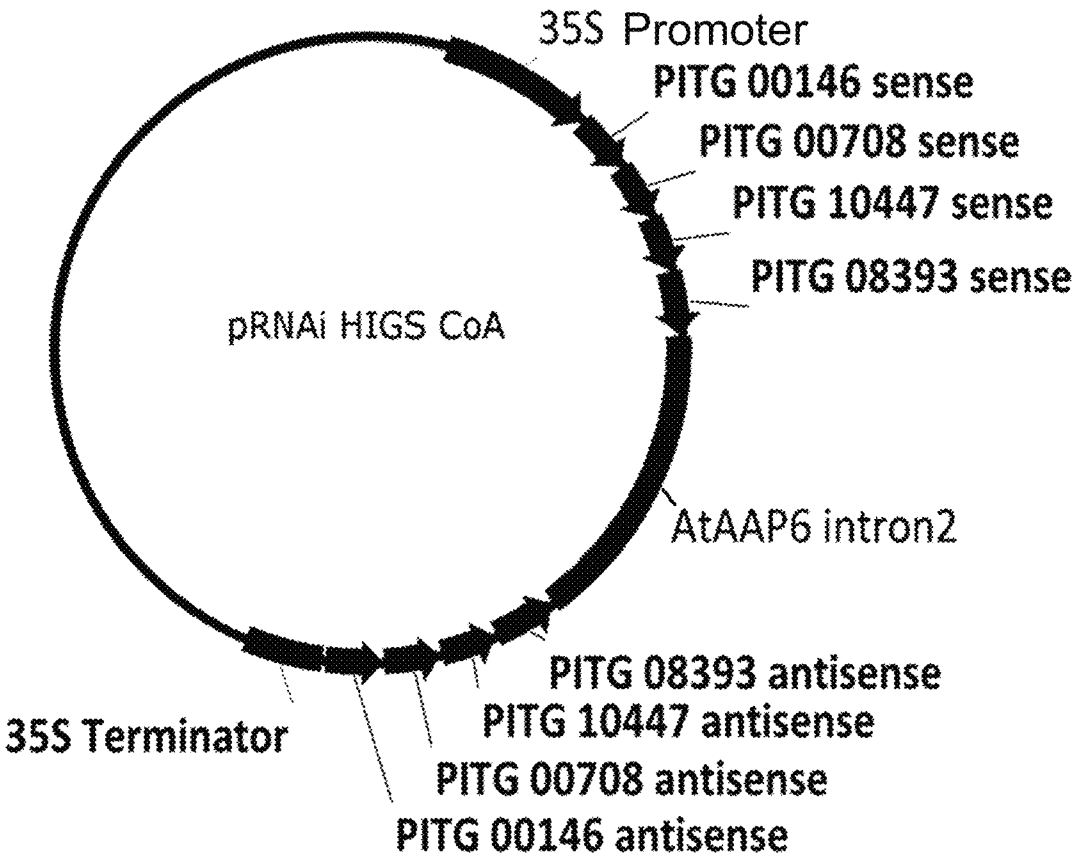
FIG. 3: Plasmid pRNAi_HIGS_CoA as an exemplary representation of a vector which contains various defined sequences in the sense-intron-antisense fragment, which should lead to the formation of dsRNA against various target genes. This vector additionally contains a CaMV 35S promoter, a multiple cloning site, an intron from the gene AtAAP6 which codes for an amino acid permease in *Arabidopsis thaliana*, a further multiple cloning site as well as a CaMV 35S terminator.
Figure 4:
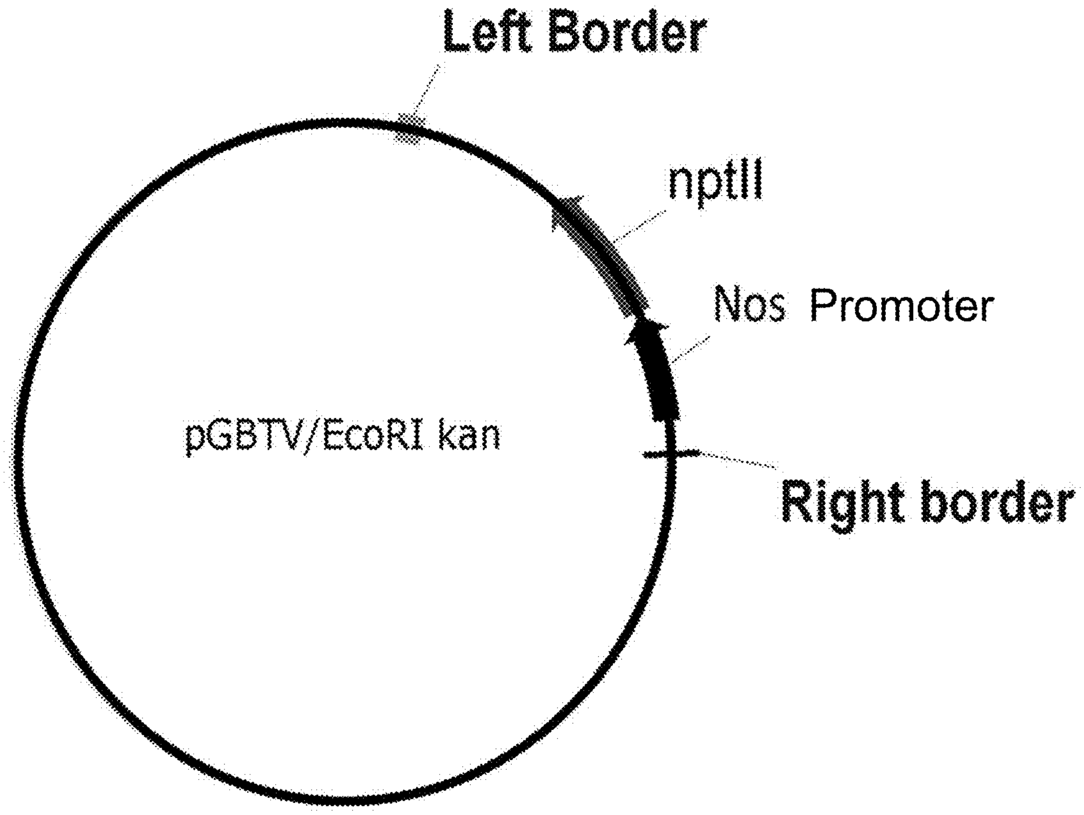
FIG. 4: Plasmid pGBTV/EcoRI_kan. Binary Ti plasmid which was used as a cloning vector.
Figure 5:
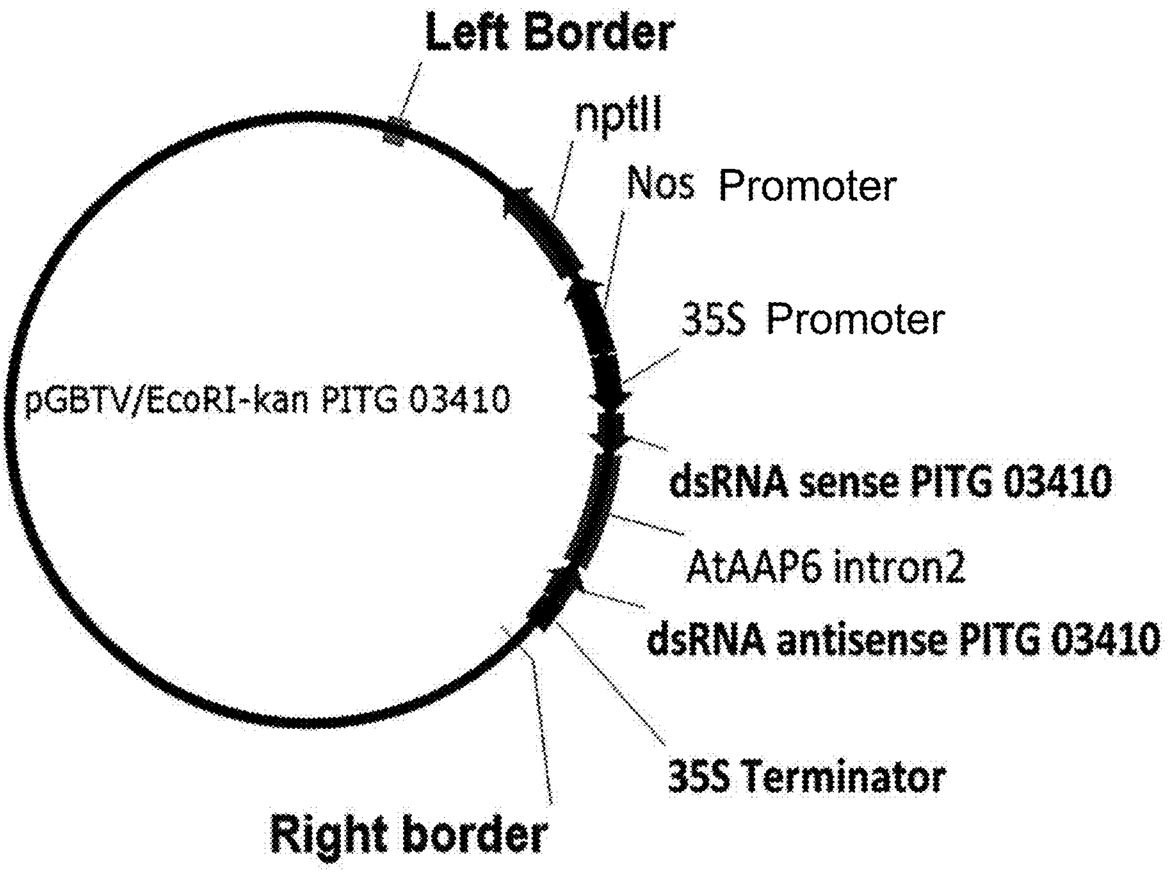
FIG. 5: Plasmid pGBTV/EcoRI_kan_PITG_03410. Binary Ti plasmid which was used for *agrobacterium*-induced transformation.
Figure 6:
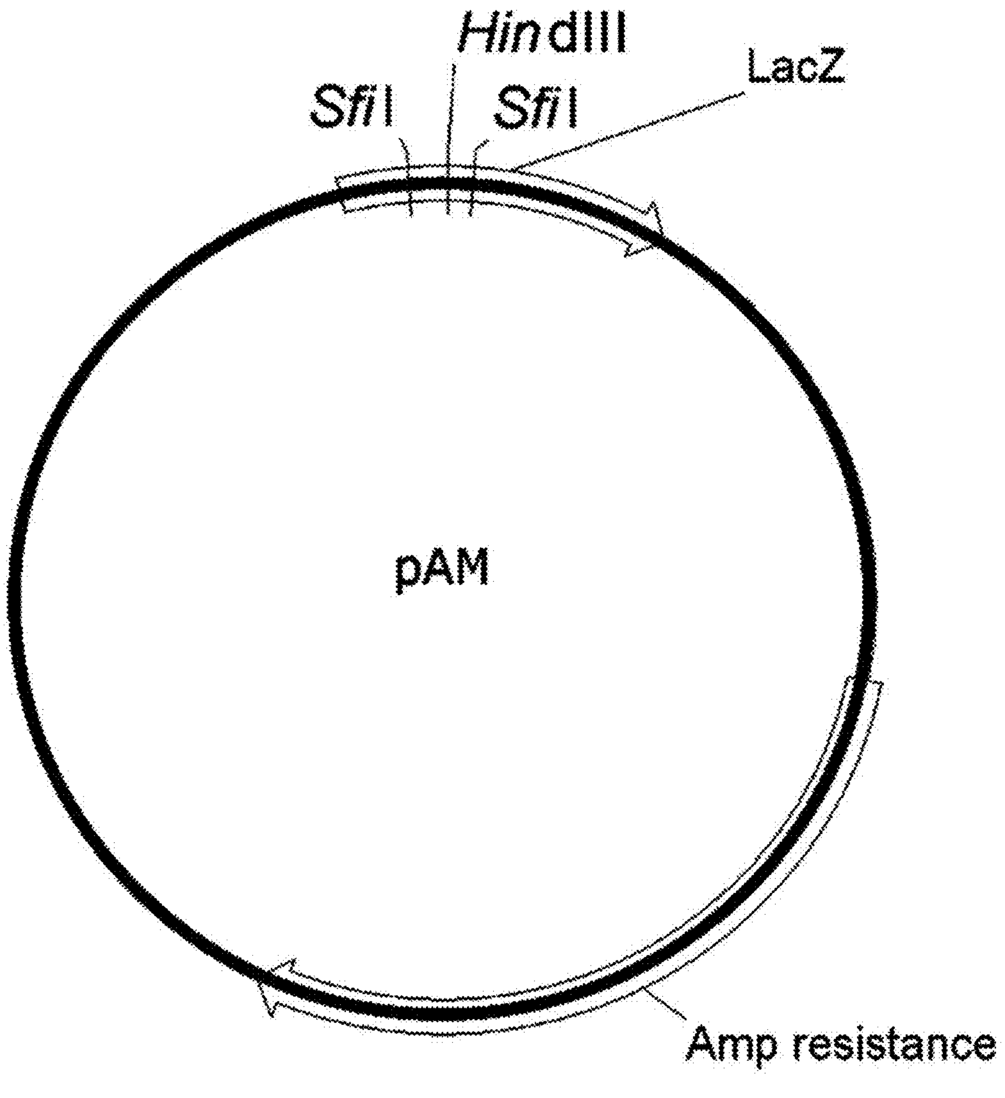
FIG. 6: Plasmid pAM, which was used as a cloning vector.
Figure 7:
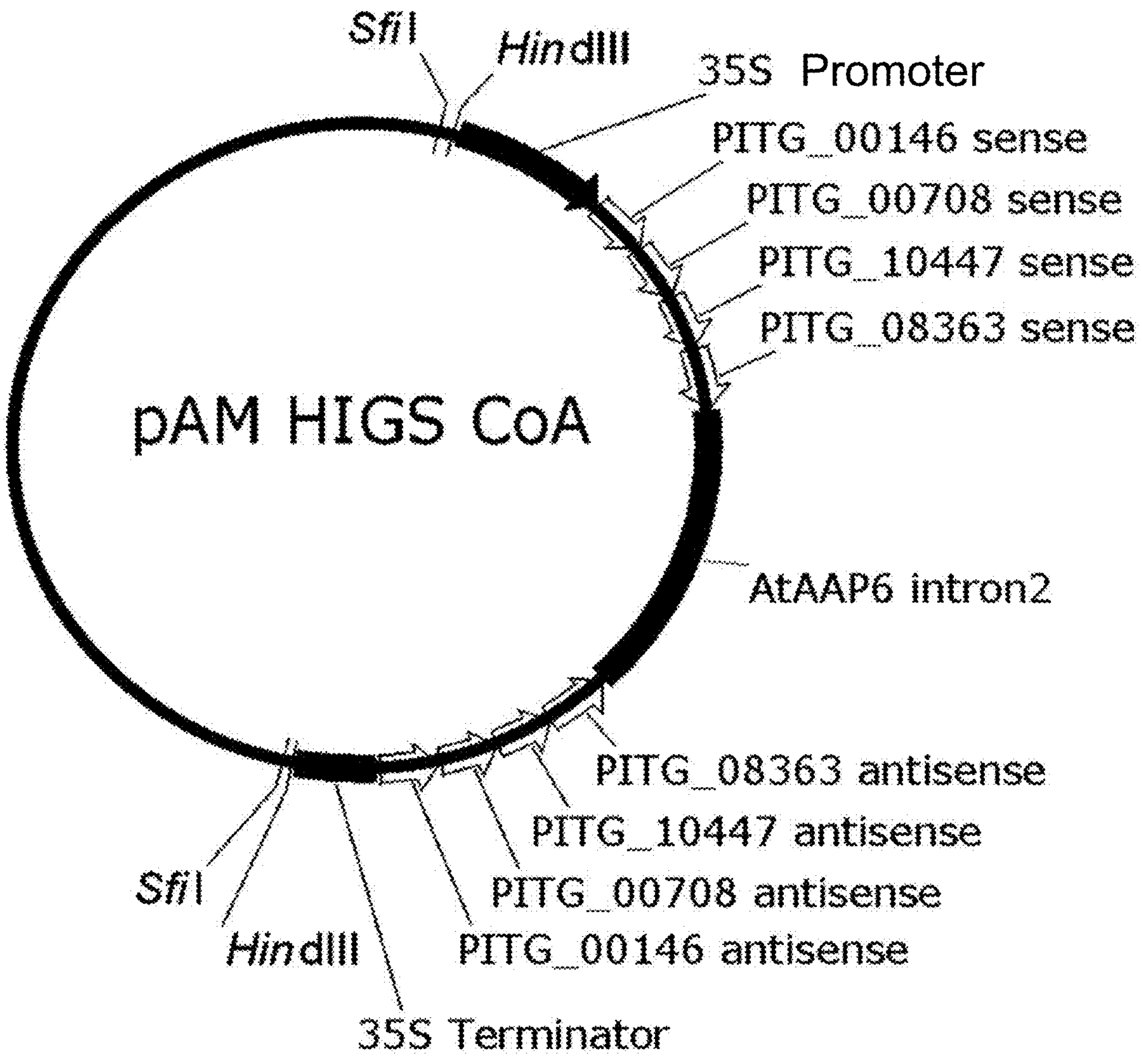
FIG. 7: Plasmid pAM_HIGS_CoA, as an example of a plasmid which was used as a cloning vector.
Figure 8:
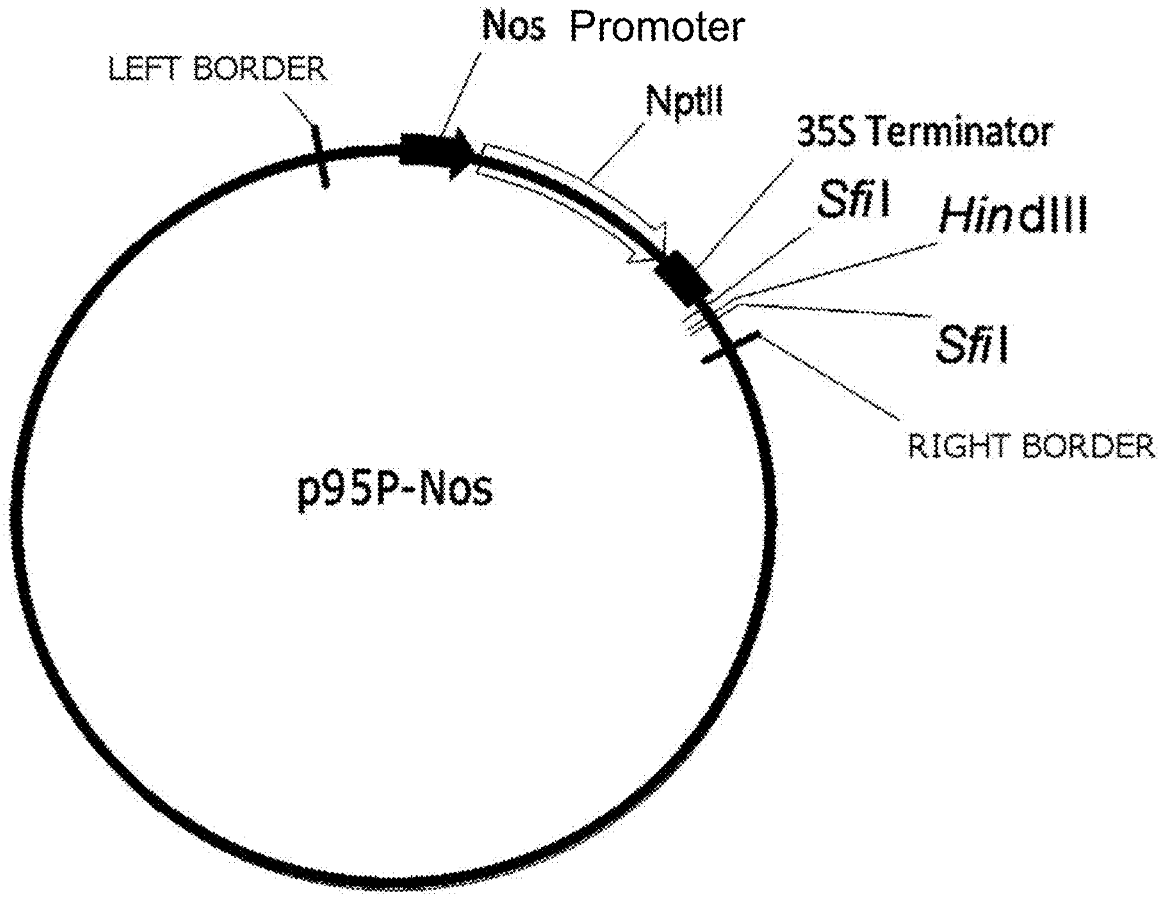
FIG. 8: Plasmid p95P-Nos. Binary Ti plasmid which was used as a cloning vector.
Figure 9:
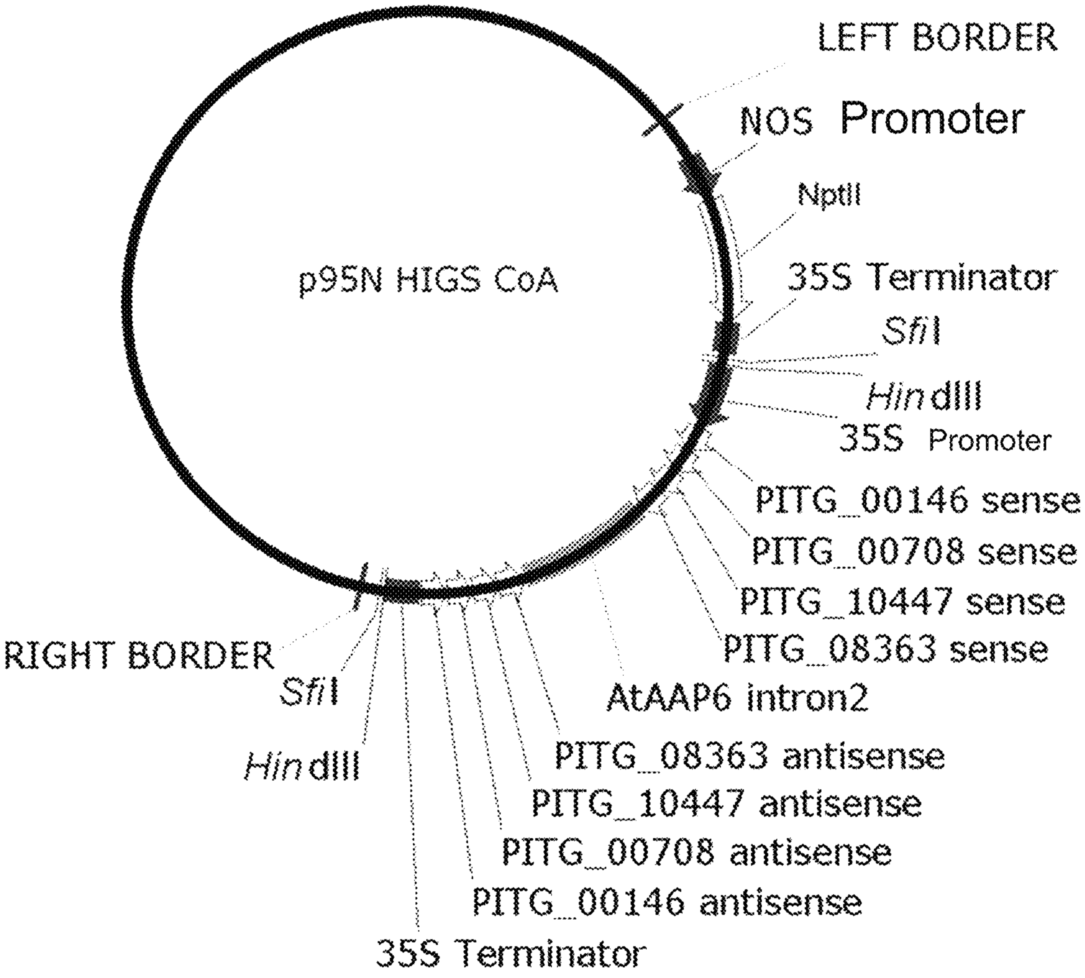
FIG. 9: Plasmid p95_N_HIGS_CoA. Binary Ti plasmid which was used for *agrobacterium*-induced transformation.

Defined sequence regions of the selected target genes were amplified using PCR and cloned in both the sense and the antisense direction into a pRNAi vector which is suitable for the system of hairpin structures (FIG. 2). In this manner, several fragments with sequence regions from various target genes can be cloned into a vector in order to generate a combination hairpin construct (FIG. 3). Starting from genomic DNA from *Phytophthora infestans*, a sequence region of 290 bp from the coding region of the gene PITG_03410 was amplified using PCR, cleaved via the restriction enzyme cleaving sites XhoI and SmaI inserted via the primer sequences and cloned into the pRNAi vector (primer 1: cgctcgaggctggatctcgcgctgaggt (SEQ ID NO: 47), primer 2: ttgatatcgcggaaggcgagagacatcg (SEQ ID NO: 45)). This vector contains a CaMV 35S promoter, a multiple cloning site, an intron from the gene AtAAP6 which codes for an amino acid permease in *Arabidopsis thaliana*, a further multiple cloning site as well as a CaMV 35S terminator. This was cleaved with XhoI and Ec1136II and the 4.098 kb vector fraction was separated using agarose gel electrophoresis and then isolated. The ligation solution was transformed in *E. coli* strain XL1-blue (Stratagene, LaJolla, Calif.). The same PITG_03410 fragment was then cloned into the plasmid pRNAi_PITG_03410_sense in the antisense direction. To this end, the fragment was again amplified from genomic DNA from *Phytophthora infestans* using PCR, cleaved via the restriction enzyme cleaving sites XhoI and SmaI inserted via the primer sequences and then ligated into the vector pRNAi_PITG_03410_sense which had been cleaved with SmaI-SalI and then linearized (FIG. 1). The sense-intron-antisense (RNAi-PITG_03410) gene fragment was cleaved out of the pRNAi vector and cloned into the vector pGBTV/EcoRI_kan (FIG. 4). To this end, both pGBTV/EcoRI_kan and pRNAi_PITG_03410 were cleaved with HindIII and ligated so that the plasmid pGBTV/EcoRI_kan_PITG_03410 was generated (FIG. 5). Alternatively, HIGS-RNAi constructs such as HIGS-CoA were initially cloned into the vector pAM (DNA Cloning Service e.K., Hamburg) (FIG. 6). To this end, both pAM and pRNAi_PITG_03410 were cleaved with HindIII and ligated, so that the plasmid pAM_HIGS_CoA was generated (FIG. 7). From the vector pAM, the HIGS_CoA fragment was integrated into the vector p95P-Nos (DNA Cloning Service e.K., Hamburg) by SfiI digestion and ligation (FIG. 8), so that the plasmid p95N_HIGS_CoA was generated (FIG. 9), which was used for potato transformation.

Figure 10:
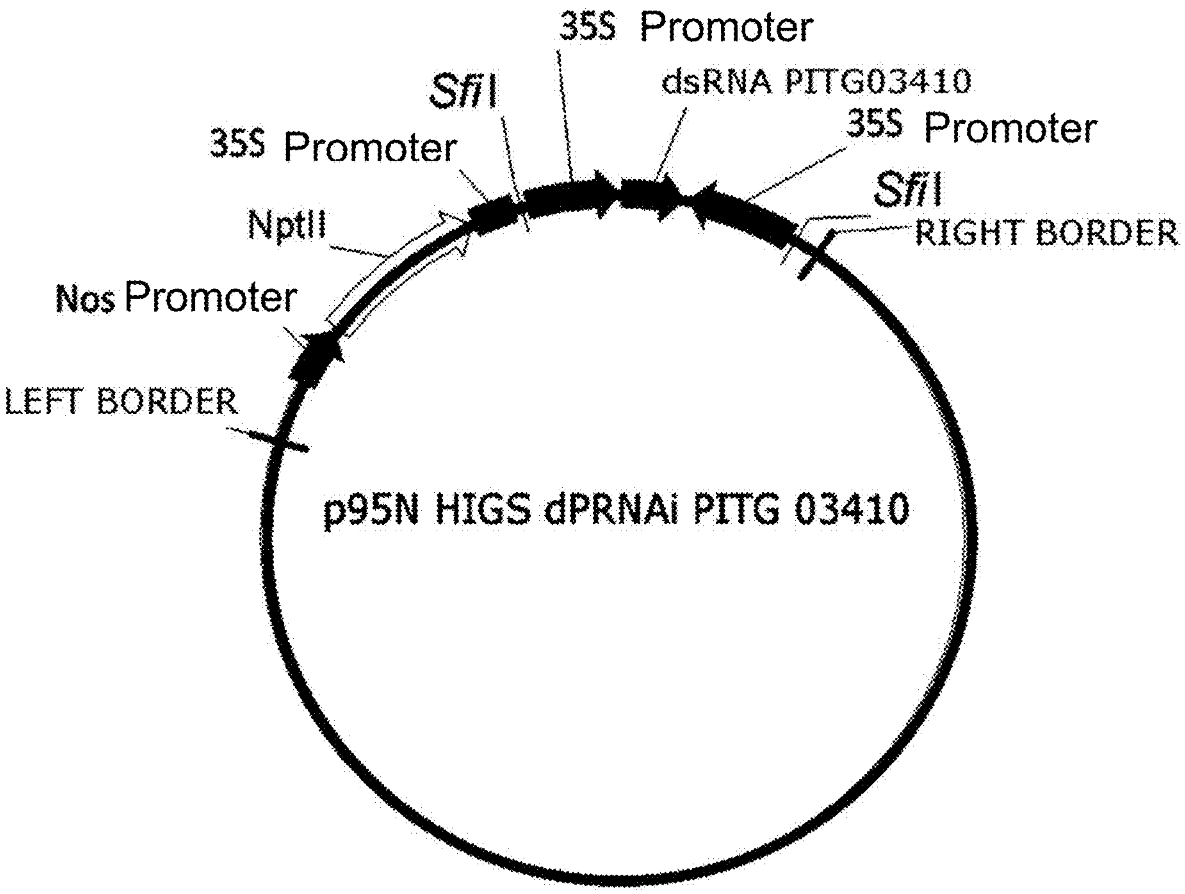
FIG. 10: Plasmid p95N_HIGS_dPRNAi_PITG_03410 as an exemplary representation of a binary vector for the formation of dsRNA against a target gene (here PITG_03410) using two CaMV 35S promoters which each flank the 3'- and the 5' end of the nucleic acid molecule.

Alternatively to a vector as described above which is suitable for the synthesis of hairpin structures, a section of the coding target gene region in the potato plant can be caused to carry out expression with the aid of two oppositely (reverse) orientated promoters (FIG. 10). In addition, gene silencing can also be envisaged by means of artificial microRNA constructs (amiRNA) using the Web microRNA Designers (WMD3) protocol. Artificial miRNAs are 21-mer single stranded RNAs which can be synthesised in order to specifically negatively regulate desired genes in plants. Regulation happens—like with siRNAs—via mRNA cleavage. These RNAi constructs are then cloned into a binary vector and transformed by *Agrobacterium tumefaciens*—induced transformation in potatoes.

Transformation and Regeneration

Figure 11:
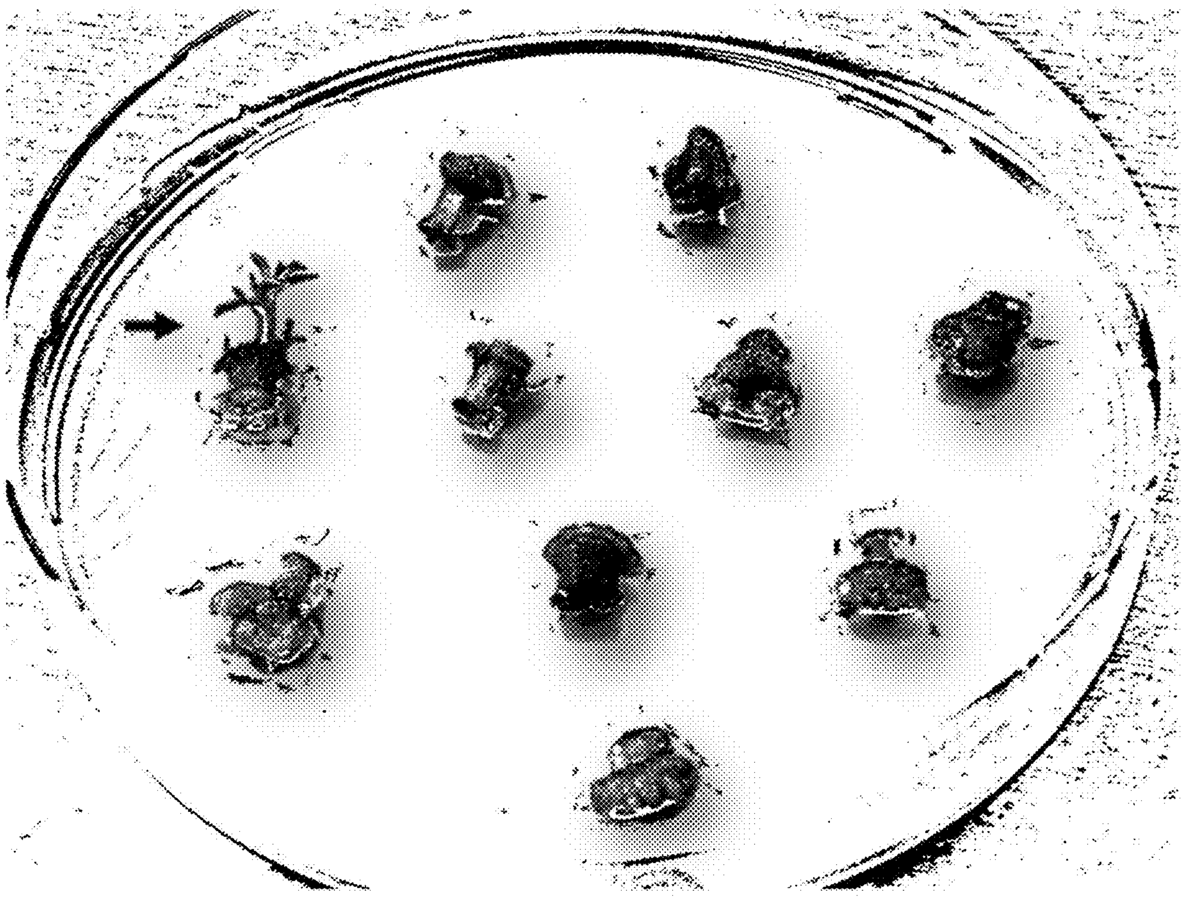
FIG. 11: Transgenic potato shoot on selection medium after transformation in the regeneration stage.
Figure 12:
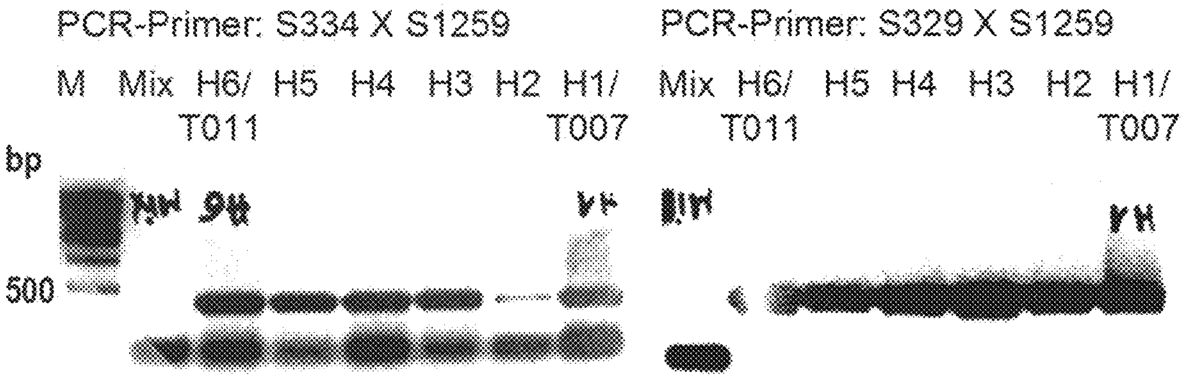
FIG. 12: Diagnostic PCR for testing the transgenicity of potatoes (PR-H4) after transformation with the binary vector pGBTV/EcoRI_kan_PITG_03410.

Transformation of the potatoes was carried out in accordance with the modified protocol by Pel et al (2009) using the antibiotic kanamycin. The donor material was cultivated in 80 mL MS(D) (25° C.; 16 h day/8 h night; 2000 lux) for 3-4 weeks. For transformation (C1), the internodes were cut out of the donor material in approximately 0.5 cm explants. These were cultivated in petri dishes with 10 mL MS(D) (15-20 Explants/dish) with 70 µl of an *Agrobacterium tumefaciens* culture which had been cultivated overnight at 28° C., which had earlier been transformed with the HIGS-RNAi construct as part of a binary vector such as, for example, p95N, incubated at 25° C. for 2 days in the dark. Next, the explants were dried on filter paper and placed in petri dishes on MSW-Medium with selection antibiotic (400 mg/L timentin+75 kanamycin mg/L) which were hermetically sealed and cultivated for 2 weeks (25° C.; 16 h day/8 h night; 2000 lux) (C2). This selection step was repeated every 2 weeks until the shoots had regenerated (from C3). Regenerated shoots (FIG. 11) were incubated on MS (30 g/L saccharose) with selection antibiotic (250 timentin mg/L+100 kanamycin mg/L) to cause rooting and tested by PCR for integration of the construct to be transformed and thus for the presence of the nucleic acids of the invention. The use of the primers Bo2299 (5'-GTGGAGAGGCTATTCG-GTA-3' (SEQ ID NO: 48)) and Bo2300 (5'-CCACCATGA-TATTCGGCAAG-3' (SEQ ID NO: 49)) led to the amplification of a 553 bp DNA fragment from the bacterial NPTII gene, which codes for neomycin phosphotransferase. Furthermore, the sense and the antisense fragment were detected using PCR, in order to ensure that the construct was complete (FIG. 12). The PCR was carried out using 10 ng of genomic DNA, a primer concentration of 0.2 µM at an annealing temperature of 55° C. in Multicycler PTC-200 (MJ Research, Watertown, USA). Propagation of the shoots which tested positive in the PCR was carried out on MS+30 g/L saccharose+400 mg/L ampicillin.

Detection of Processed Double-Stranded RNA and siRNAs

In the transformed plants, the expressed hairpin or double-stranded RNAs were processed over the natural plant RNAi mechanisms in a manner such that these RNA molecules were degraded into small single stranded RNAs. These siRNAs are deposited on the mRNA of the corresponding target gene in oomycetes and thus effect silencing of this gene. The plants are thus placed in the position of protecting themselves against attacking pathogens. By means of this concept, transgenic potato plants can be produced which have an increased resistance to *P. infestans*.

The transformation of potato plants with constructs for the expression of hairpin or double-stranded RNAs should result in the fact that the resulting dsRNAs are processed to siRNAs in preference to the natural plant RNAi mechanisms. In order to measure the fragmentation of the dsRNA, whole RNA was isolated from the transgenic plants using the trizol method (Chomczynski and Sacchi, 1987). 15 µg of whole RNA/sample was supplemented with formamide, denatured and separated electrophoretically in a 1% agarose gel with 10% formaldehyde in 1×MOPS buffer (0.2 M MOPS (sodium salt), 0.05 M NaOAc, 0.01 M EDTA in DEPC $dH_2O$. pH 7.0 with NaOH). The separated RNA was transferred from the gel onto a nylon membrane (positively charged) using the Northern Blot method into 20×SSC buffer (saline-sodium citrate buffer). This was hybridized with a radioactively labelled probe which was complementary to the sequence of the target gene fragment which was present in the sense or in the antisense direction in the construct transformed into the plants. In this manner, RNA fragments which are complementary to the sequence of the dsRNA fragment are labelled and detected by means of a phosphoimager.

The transformation of potato plants with constructs for the expression of hairpin or double-stranded RNAs should result in the fact that the resulting dsRNA are processed to siRNAs in preference to the natural plant RNAi mechanisms. In order to measure the fragmentation of the dsRNA into siRNAs, whole RNA was isolated from the transgenic plants using the trizol method (Chomczynski and Sacchi, 1987). 15 µg of whole RNA/sample was supplemented with formamide, denatured and separated electrophoretically in a polyacrylamide gel with 15% Tris/boric acid/EDTA (TBE) and uric acid in 0.5×TBE. The separated RNA was transferred onto a nylon membrane (neutral) from the gel using the Tank Blot method in 0.5×TBE. This was hybridized with a radioactively labelled probe which was complementary to the sequence of the target gene fragment which was present in the sense or in the antisense direction in the construct transformed in the plants. In this manner, siRNAs which are complementary to the sections of sequence of the dsRNA fragment are labelled and detected by means of a phosphoimager.

In various transgenic potato lines such as, for example, PR-H4 lines or PR-H2 lines, such siRNAs could be detected (FIG. 13 A, B). This shows that the constructs transformed in the plants are recognized and processed by plant RNAi mechanisms such that siRNAs against RIGS target genes from *P. infestans* can be formed which should carry out silencing of this gene in the pathogen.

Measurement of Resistance in Transgenic Potato Plants in the Detached Leaf Assay To test the resistance of the transgenic potato leaves, the transgenic plants were cultivated from in vitro plants in the greenhouse in 5 L pots. After 6-8 weeks, 2 pinnae per plant were cut off and placed in a sealed plastic box on a moist Grodan pad such that the leaf stem was in the moist Grodan material. This ensured that the humidity was high. The boxes were incubated at 18° C. using a day/night program (sunlight, February-September). The pinna leaflets were inoculated with drops of a zoospore suspension (10 µL; $10^4$ zoospores/mL) of *Phytophthora infestans*. After 24 hours, the lid of the boxes was opened somewhat in order to allow a gentle circulation of air in the boxes. The optical scoring and quantification of the zoospores was carried out after 6 days. The optical scoring evaluated the degree of infection and the destruction of the pinna leaf by *P. infestans*. Counting the sporangia led to quantification of the reproductive ability of the pathogen in the plant. In this regard, the previously infected leaves of a pinna were incubated in 5 mL of water in Falcon tubes on a shaker for 2 h, so that the sporangia were loosened from the leaf. The sporangia were then counted with the aid of a Thoma counting chamber under a microscope.

In various HIGS potato lines which were generated by transformation of various potato genotypes, a reduced sporangia count could be determined after infection with *P. infestans* (6 dpi) (FIG. 15B-18B). This indicates that the reproductive ability of the pathogen on the transgenic plants has been restricted.

The gene PITG_03410 was tested as a target gene for HIGS in the genetic background of the potato varieties Baltica, Hermes and Desiree as well as the variety Russet Burbank using a vector as shown in FIG. 5. The detached leaf assay applied to these transgenic plants of the variety Russet Burbank showed that the reproductive ability of the pathogen on the transgenic plants was restricted compared with non-transgenic control plants (FIG. 20).

As an alternative to vectors which are suitable for the synthesis of hairpin structures, a vector as shown in FIG. 10 with the target gene PITG_03410 was introduced into potato plants of the variety Hermes and the transgenic lines were investigated in the detached leaf assay (FIG. 21). Here again, it was shown that the reproductive ability of *P. infestans* was limited on the transgenic plants compared with non-transgenic control plants.

Potato plants of the variety Russet Burbank which had been transformed with a combination vector against the genes PITG_00146, PITG_00708, PITG_10447 and PITG_08363 of FIG. 3 were also tested in the detached leaf assay. It was observed that the reproductive ability of *P. infestans* on these transgenic plants was restricted compared with non-transgenic control plants (FIG. 22). Similarly, the detached leaf assay showed that the reproductive ability of *P. infestans* on transgenic plants of the variety Russet Burbank is restricted when transformed with a vector in accordance with FIG. 29, FIG. 30, FIG. 31 or FIG. 32 which is directed against the genes PITG_06748 (FIG. 23), PITG_09306 (FIG. 24), PITG_09193 (FIG. 25) or PITG_19177 (FIG. 27). Even on transgenic plants of the variety Desiree which were transformed with a vector as shown in FIG. 31 or FIG. 32 which is directed against the gene PITG_09193 (FIG. 25) or PITG_19177 (FIG. 27), the detached leaf assay showed that the reproductive ability of *P. infestans* was restricted compared to non-transgenic control plants.

Transient Test System for RNAi Vectors in Potato Leaves

A transient test system in accordance with Birch et al. (2010) was developed to investigate the functionality of the RNAi vectors against selected target gene sequences of *P. infestans*. By means of co-bombardment, a RNAi vector targeting a target gene was expressed transiently in potato leaves together with a fusion construct consisting of a luciferase reporter gene and the test target fragment. If the dsRNA construct is processed in the RNAi vector, then the formation of dsRNA and the resulting formation of siRNAs should be ensured. These siRNAs should not only carry out the degradation of the target gene fragment transcript, but also give rise to the fused reporter gene transcript, so that with a functional RNAi construct, a reduction in the luciferase activity can be observed. The plasmid pABM-70Sluci comprises a double CaMV 35S promoter, a multiple cloning site, the coding sequence for the luc gene from *Photinus pyralis*, which codes for a luciferase, separated from a modified intron PIV2 from the potato gene St-LS1 (Eckes et al. 1986, Vancanneyt et al. 1990), a further multiple cloning site as well as a Nos terminator from the nopalin synthase gene from *Agrobacterium tumefaciens*. The PCR-amplified fragment of the coding sequence region, for example of the PITG_03410 gene, was cloned into this plasmid pABM-70Sluci, which was also cloned into the pRNAi vector to produce the dsRNA construct (FIG. 14A).

This transient test system can not only be used for validation of the general functionality of the RNAi construct, but also be used in order to investigate different sequence regions of a gene as regards its silencing effect and finally can select the best sequence regions of a gene for optimal silencing. In addition, the bombardment of transgenic plants stably transformed with a RNAi construct can serve to determine the silencing efficiency of the individual transgenic HIGS potato lines which, for example, can differ substantially depending on the integration site for the construct. In various transgenic HIGS potato lines which are obtained by transformations in various potato genotypes, and which show a reduced sporangia count after infection with *P. infestans*, a reduction in the luciferase activity could also be measured (FIG. 15A-18A). This shows the functionality of the RIGS constructs processed to siRNAs in relation to a silencing of the target gene sequence in the transgenic plants.

When the coding gene sequences which are to be silenced by a combination construct such as pRNAi_HIGS-CoA, for example (target genes: PITG_08393, PITG_00146, PITG_10447, PITG_00708), each cloned into the vector pABM_70Sluci behind the coding sequence for the luc gene from *Photinus pyralis* (pABM_70Sluci_PITG_08393, pABM_70Sluci_PITG_00146, pABM_70Sluci_PITG_10447, pABM_70Sluci_PITG_00708) and together with the vector pRNAi_HIGS_CoA, are to be transiently expressed in potato leaves, the silencing efficiency of the combination construct can be analysed on the various target genes. This is also possible by the bombardment of transgenic plants stably transformed with the RNAi combination construct with the individual fusion constructs consisting of the luciferase reporter gene and the test coding sequences of the various target genes.

The luciferase activity determinations were carried out with the aid of Dual Luciferase® Reporter Assays (Promega, Mannheim) (Schmidt et al. 2004).

Measurement of Resistance in Transgenic Potato Plants Under Outdoor Conditions

For the resistance test for the transgenic potato plants under outdoor conditions, the transgenic plants were initially cultivated early in the year (March) from in vitro plants in the greenhouse for 3 weeks in multiport pads. Next, these plants were planted out into a greenhouse with a wire mesh roof in natural soil so that the plants were exposed to environmental conditions, for example temperature, sunlight, precipitation and humidity, which were comparable with field conditions. The plants were planted out in 3 plots each with 6 plants. After 8 weeks, one pinna from each of 2 plants in a plot was inoculated with *P. infestans* by spray inoculation (750 μL; $10^4$ zoospores/mL). Plastic bags were placed over these pinnae to ensure that the humidity would be high and to promote infection. After two days, these plastic bags were removed. Proliferation of the blight by *Phytophthora infestans* in the greenhouse was scored optically and documented photographically every week. The criteria for scoring the infection was initially only on the infected pinna leaf (0: no infection, 1: slight infection (½ number of infected pinna leaves infected), 2: infection on more than ½ leaves of a pinna, 3: infection on all leaves of the pinna) and then the spread of the infection to the plant and the whole plot (4: infection also extends to some other leaves of the plant, 6: infection also extends to other plants, 8: infection also extends substantially to other plants, 10: 10% of the plants infected/destroyed, 20: 20% of plants infected/destroyed, 100: 100% of the plants infected/destroyed).

In various transgenic HIGS potato lines (PR-H-4-7, PR-H-4-11) which were obtained by transformations in the potato genotype Hermes, a greatly reduced degree of infection of these plants during the course of infection with *Phytophthora infestans* was determined compared with the transformation genotype Hermes which had been cultivated, planted out and infected as the control exactly as with the transgenic plants. The reduced degree of infection was initially reflected by a greatly reduced infection capability of the pathogen on the inoculated pinnae (scores 21 days post-infection: PR-H-4-7: 3.3; PR-H-4-11: 3.2; Hermes 7.6) and at later times by a substantially reduced propagation ability of the pathogen to these plants (scores 32 days post-infection: PR-H-4-7: 26; PR-H-4-11: 15; Hermes: 80) (FIG. 19 A, B).

By means of the tests described, not only could processing of the HIGS construct in transgenic potato plants to siRNAs be demonstrated, but also the functionality of these constructs in respect of silencing of the target gene sequence in these transgenic plants, and an increased resistance of these plants to *P. infestans* could be quantified by a reduced sporangia production of the pathogen on these host plants. Since the identification of functional HIGS target genes is not possible without careful testing of their functionality, these analyses as described in detail here are particularly suitable for defining genes which are effective in the HIGS construct and for generating resistant HIGS plants.

REFERENCES

Avrova A O, Boevink P C, Young V, Grenville-Briggs L J, van West P, Birch P R, Whisson S C (2008) A novel *Phytophthora infestans* haustorium-specific membrane protein is required for infection of potato. Cell Microbiol. 10(11):2271-84.

Birch R G, Shen B, Sawyer B J, Huttner E, Tucker W Q, Betzner A S (2010) Evaluation and application of a luciferase fusion system for rapid in vivo analysis of RNAi targets and constructs in plants. Plant Biotechnol J. May 1; 8(4):465-75. Epub 2010 Jan. 19

Blackman L M, Arikawa M, Yamada S, Suzaki T, Hardham A R (2011) Identification of a mastigoneme protein from *Phytophthora nicotianae*. Protist. 162(1):100-14.

Benfey, P. N., Ren, L., and Chua, N.-H. (1990). Combinatorial and synergistic properties of CaMV 35S enhancer subdomains. EMBO J. (9), 1685-1696.

Chomczynski P, Sacchi N. (1987) Single-step method of RNA isolation by acid guanidinium thiocyanate-phenol-chloroform extraction. Anal Biochem. 162(1):156-9

Eckes P., Rosahl S., Schell J., Willmitzer L. (1986) Isolation and characterization of a light-inducible, organ-specific gene from potato and analysis of its expression after tagging and transfer into tobacco and potato shoots. Molecular and General Genetics 205 (1) 14-22, DOI: 10.1007/BF02428027

Fire A, Xu S, Montgomery M K, Kostas S A, Driver S E, Mello C C. (1998) Potent and specific genetic interference by double-stranded RNA in *Caenorhabditis elegans*. Nature February 19; 391(6669):806-11

Grenville-Briggs L J, Avrova A O, Bruce C R, Williams A, Whisson S C, Birch P R, van West P (2005) Elevated amino acid biosynthesis in *Phytophthora infestans* during appressorium formation and potato infection. Fungal Genet Biol. 42(3):244-56.

Inoue S B, Takewaki N, Takasuka T, Mio T, Adachi M, Fujii Y, Miyamoto C, Arisawa M, Furuichi Y, Watanabe T (1995) Characterization and gene cloning of 1,3-beta-D-glucan synthase from *Saccharomyces cerevisiae*. Eur J Biochem 231(3):845-54.

Judelson H S, Narayan R D, Ah-Fong A M, Kim K S (2009a) Gene expression changes during asexual sporulation by the late blight agent *Phytophthora infestans* occur in discrete temporal stages. Mol Genet Genomics. 281(2):193-206.

Judelson H S, Tani S, Narayan R D (2009b) Metabolic adaptation of *Phytophthora infestans* during growth on leaves, tubers and artificial media. Mol Plant Pathol. 10(6):843-55.

Kamoun S, van West P, Vleeshouwers V G, de Groot K E, Govers F. (1998). Resistance of *Nicotiana benthamiana* to *Phytophthora infestans* is mediated by the recognition of the elicitor protein INF1. Plant Cell. September; 10(9):1413-26.

Lesage G, Sdicu A M, Ménard P, Shapiro J, Hussein S, Bussey H (2004) Analysis of beta-1,3-glucan assembly in *Saccharomyces cerevisiae* using a synthetic interaction network and altered sensitivity to caspofungin. Genetics. May; 167(1):35-49

Li A, Wang Y, Tao K, Dong S, Huang Q, Dai T, Zheng X, Wang Y (2010) PsSAK1, a Stress-Activated MAP Kinase of *Phytophthora* sojae, Is Required for Zoospore Viability and Infection of Soybean. Mol Plant Microbe Interact. 23(8):1022-31.

Mazur P, Morin N, Baginsky W, el-Sherbeini M, Clemas J A, Nielsen J B, Foor F (1995) Differential expression and function of two homologous subunits of yeast 1,3-beta-D-glucan synthase. Mol Cell Biol. 15(10):5671-81.

Pel M A, Foster S J, Park T H, Rietman H, van Arkel G, Jones J D G, Van Eck H J, Jacobsen E, Visser R G F, Van der Vossen E A G (2009) Mapping and cloning of late blight resistance genes from *Solanum venturii* using an interspecific candidate gene approach. MPMI 22:601-615

Roemer T, Paravicini G, Payton M A, Bussey H (1994) Characterization of the yeast (1→6)-beta-glucan biosynthetic components, Kre6p and Skn1p, and genetic interactions between the PKC1 pathway and extracellular matrix assembly. J Cell Biol. 127(2):567-79.

Saito, K., Yamazaki, M., Kaneko, H., Murakoshi, I., Fukuda, Y., and van Montagu, M. (1991). Tissue-specific and stress-enhancing expression of the TR promoter for mannopine synthase in transgenic medicinal plants. Planta 184, 40-46.

Schmidt K., Heberle B., Kurrasch J., Nehls R., Stahl D. J. (2004) Suppression of phenylalanine ammonia lyase expression in sugar beet by the fungal pathogen *Cercospora beticola* is mediated at the core promoter of the gene. Plant Mol. Biol., 55: 835-852.

Stahl D. J., Kloos, D. U., and Hehl, R. (2004). A sugar beet chlorophyll a/b binding protein void of G-box like elements confer strong and leaf specific reporter gene expression in transgenic sugar beet. BMC Biotechnology 4; 31: 12

Vancanneyt G., Schmidt R., O'Connor-Sanchez A., Willmitzer L., Rocha-Sosa M. (1990) Construction of an intron-containing marker gene: splicing of the intron in transgenic plants and its use in monitoring early events in *Agrobacterium*-mediated plant transformation. Mol Gen Genet. 220(2):245-50

Van West P, Kamoun S, van't Klooster J W, Govers F (1999) Internuclear gene silencing in *Phytophthora infestans*. Mol Cell. March; 3(3):339-48.

Wang Y, Dou D, Wang X, Li A, Sheng Y, Hua C, Cheng B, Chen X, Zheng X, Wang Y (2009) The PsCZF1 gene encoding a C2H2 zinc finger protein is required for growth, development and pathogenesis in *Phytophthora* sojae. Microb Pathog. 47(2):78-86.

Wang Y, Li A, Wang X, Zhang X, Zhao W, Dou D, Zheng X, Wang Y (2010) GPR11, a putative seven-transmembrane G protein-coupled receptor, controls zoospore development and virulence of *Phytophthora sojae*. Eukaryot Cell 9(2):242-50.

Yin C, Jurgenson J E, Hulbert S H (2011) Development of a Host-Induced RNAi System in the Wheat Stripe Rust Fungus *Puccinia striiformis* f. sp. *Tritici*. MPMI 24(5): 554-561. doi:10.1094/MPMI-10-10-0229. © 2011 The American Phytopathological Society Zhang M, Wang Q, Xu K, Meng Y, Quan J, et al. (2011) Production of dsRNA Sequences in the Host Plant Is Not Sufficient to Initiate Gene Silencing in the Colonizing Oomyzete Pathogen *Phytophthora parasitica*. PLoS ONE 6(11): e28114.

EP 1716238 (Bayer S.A.S.) METHOD FOR MODIFYING GENE EXPRESSION OF A PHYTOPATHOGENIC FUNGUS WO 2006/070227 (Devgen N.V.) METHOD FOR DOWN-REGULATING GENE EXPRESSION IN FUNGI WO 2009/112270 (Leibniz-Institut für Pflanzengenetik and Kulturpflanzenforschung) METHOD FOR CREATING BROAD-SPECTRUM RESISTANCE TO FUNGI IN TRANSGENIC PLANTS US 2010/0257634 (Venganza Inc.) BIOASSAY FOR GENE SILENCING CONSTRUCTS WO 2006/047495 (Venganza Inc.) METHODS AND MATERIALS FOR CONFERRING RESISTANCE TO PESTS AND PATHOGENS OF PLANTS

The invention claimed is:

1. A transgenic plant of the species *Solanum tuberosum* or a part thereof comprising a stably integrated first double-stranded DNA and a stably integrated second double-stranded DNA, wherein the nucleotide sequences of the coding strands of the first and second DNA are reverse complements of each other, so that a transcript of the first DNA and a transcript of the second DNA are capable of hybridizing to form a double-stranded RNA and whereby the plant expressing said double-stranded RNA is resistant to an oomycete of the genus *Phytophthora*, wherein the coding strand of the first DNA comprises:

(a) at least 23 successive nucleotides of the nucleotide sequence of SEQ ID NO: 38, or (b) a nucleotide sequence which is complementary to at least 23 successive nucleotides of the nucleotide sequence of SEQ ID NO: 38.

2. The transgenic plant or the part thereof of claim 1, wherein the plant exhibits a resistance against *Phytophthora infestans*.

3. The transgenic plant or the part thereof of claim 1, wherein the double-stranded RNA is miRNA or siRNA.

4. The transgenic plant or the part thereof of claim 1, wherein the first DNA and the second DNA are operatively linked to at least one promoter.

5. The part of the transgenic plant of claim 1, wherein the part is a seed or a cell.

6. A method for producing a transgenic plant of the species *Solanum tuberosum* which plant exhibits a resistance to an oomycete of the genus *Phytophthora*, comprising the following steps:

(i) producing a transformed first parent plant comprising a first double-stranded DNA which is stably integrated into the genome of said first parent plant and which has a coding strand which comprises:

(a) at least 23 successive nucleotides of the nucleotide sequence of SEQ ID NO: 38, or (b) a nucleotide sequence which is complementary to at least 23 successive nucleotides of the nucleotide sequence of SEQ ID NO: 38;

(ii) producing a transformed second parent plant comprising a second double-stranded DNA which is stably integrated into the genome of said second parent plant, wherein the nucleotide sequences of the coding strands of the first and second DNA are reverse complements of each other, so that a transcript of the first DNA and a transcript of the second DNA are capable of hybridizing to form a double-stranded RNA and whereby the plant expressing said double-stranded RNA becomes resistant to an oomycete of the genus *Phytophthora;*

(iii) crossing the first parent plant with the second parent plant; and (iv) selecting a plant in the genome of which both the first double-stranded DNA and the second double-stranded DNA have been stably integrated.

7. The method of claim 6, wherein the resistance is resistance to *Phytophthora infestans*.

8. The method of claim 6, wherein the double-stranded RNA is miRNA or siRNA.

9. A composition for external application to plants comprising a double-stranded RNA, wherein a first strand of said double-stranded RNA corresponds to a transcript of a first double-stranded DNA [comprising a coding strand] which comprises:

(a) at least 23 successive nucleotides of the nucleotide sequence of SEQ ID NO:38 or (b) a nucleotide sequence which is complementary to at least 23 successive nucleotides of the nucleotide sequence of SEQ ID NO:38;

and wherein a second strand of said double-stranded RNA corresponds to a transcript of a second double-stranded DNA which is the reverse complement of the first double-stranded DNA.

10. A method for conferring resistance against an oomycete of the genus *Phytophthora* in a plant or a plant part, said method comprising administering to said plant or plant part the composition of claim 9.

11. The method of claim 10, wherein the oomycete of the genus *Phytophthora* is *Phytophthora infestans*.

12. An isolated nucleic acid sequence comprising a double-stranded first DNA and a double-stranded second DNA, wherein the nucleotide sequences of the coding strands of the first and second DNA are reverse complements of each other, so that a transcript of the first DNA and a transcript of the second DNA are capable of hybridizing to form a double-stranded RNA, wherein the first DNA comprises (a) at least 23 successive nucleotides of the nucleotide sequence of SEQ ID NO: 38, or (b) a nucleotide sequence which is complementary to at least 23 successive nucleotides of the nucleotide sequence of SEQ ID NO: 38.

13. A vector comprising the nucleic acid sequence of claim 12.

14. An *agrobacterium* comprising the nucleic acid sequence of claim 12.

* * * * *